United States Patent
Lindberg Møller et al.

(10) Patent No.: US 10,689,672 B2
(45) Date of Patent: Jun. 23, 2020

(54) VANILLIN SYNTHASE

(71) Applicants: Evolva SA, Reinach (CH); University of Copenhagen, Copenhagen (DK)

(72) Inventors: Birger Lindberg Møller, Brønshøj (DK); Esben Halkjaer Hansen, Frederiksberg (DK); Jørgen Hansen, Allschwil (CH); Nethaji Janeshawari Gallage, Frederiksberg (DK)

(73) Assignees: EVOLVA SA, Reinach (CH); UNIVERSITY OF COPENHAGEN, Copenhagen (DK)

( * ) Notice: Subject to any disclaimer, the term of this patent is extended or adjusted under 35 U.S.C. 154(b) by 34 days.

(21) Appl. No.: 14/438,200

(22) PCT Filed: Nov. 5, 2013

(86) PCT No.: PCT/DK2013/050357
§ 371 (c)(1),
(2) Date: Apr. 23, 2015

(87) PCT Pub. No.: WO2014/067534
PCT Pub. Date: May 8, 2014

(65) Prior Publication Data
US 2015/0267227 A1  Sep. 24, 2015

Related U.S. Application Data

(60) Provisional application No. 61/722,513, filed on Nov. 5, 2012.

(51) Int. Cl.
| | | |
|---|---|---|
| *C12N 9/10* | (2006.01) | |
| *C12P 7/24* | (2006.01) | |
| *C12N 9/88* | (2006.01) | |
| *C12N 15/82* | (2006.01) | |
| *A23L 27/24* | (2016.01) | |
| *C12N 9/04* | (2006.01) | |
| *C12P 7/22* | (2006.01) | |
| *C12P 19/46* | (2006.01) | |

(52) U.S. Cl.
CPC ............... *C12P 7/24* (2013.01); *A23L 27/24* (2016.08); *C12N 9/0006* (2013.01); *C12N 9/1051* (2013.01); *C12N 9/88* (2013.01); *C12N 15/8243* (2013.01); *C12N 15/8257* (2013.01); *C12P 7/22* (2013.01); *C12P 19/46* (2013.01); *C12Y 101/03038* (2013.01); *C12Y 204/01126* (2013.01); *C12Y 401/02041* (2013.01)

(58) Field of Classification Search
None
See application file for complete search history.

(56) References Cited

U.S. PATENT DOCUMENTS

| | | |
|---|---|---|
| 5,128,253 A | 7/1992 | Labuda et al. |
| 5,204,253 A | 4/1993 | Sanford et al. |
| 5,538,880 A | 7/1996 | Lundquist et al. |
| 6,013,863 A | 1/2000 | Lundquist et al. |
| 6,133,003 A | 10/2000 | Rabenhorst et al. |
| 6,235,507 B1 | 5/2001 | Muheim et al. |
| 6,329,571 B1 | 12/2001 | Hiei |
| 2003/0070188 A1* | 4/2003 | Havkin-Frenkel ..... A01H 4/001 800/278 |
| 2003/0092143 A1 | 5/2003 | Rabenhorst et al. |
| 2009/0186399 A1 | 7/2009 | Xu et al. |
| 2011/0065156 A1* | 3/2011 | Asaff Torres ............. C12P 7/24 435/147 |

FOREIGN PATENT DOCUMENTS

| | | |
|---|---|---|
| WO | 19941013614 | 6/1994 |
| WO | 20011040491 | 6/2001 |
| WO | WO 2003/071861 | 9/2003 |
| WO | WO 2008/049299 | 5/2008 |
| WO | 20131022881 | 2/2013 |

OTHER PUBLICATIONS

Brochado et al., 2010, Microbial Cell Factories 9: 84, pp. 1-15.*
Mukai et al., 2010, Journal of Bioscience and Bioengineering 109: 564-569.*
Sequence of vanillin synthase from Glechoma hederacea, GenBank accession No. AID23868.1, published Jun. 18, 2014.*
Baudin et al., "A simple and efficient method for direct gene deletion in Saccharomyces cerevisiae," Nucleic Acids Res. 21(14):3329-30 (Jul. 1993).
Boddeker et al., "Pervaporation at the vapor pressure limit: Vanillin," Journal of Membrane Science 137(1-2):155-8 (Dec. 1997).
Borges Da Silva, "An integrated process to produce vanillin and lignin-based polyurethanes from Kraft lignin," Chemical Engineering Research and Design 87(9):1276-92 (Sep. 2009).
Fan et al., "Expression of a senescence-associated cysteine protease gene related to peel pitting of navel orange (*Citrus sinensis* L. Osbeck)," Plant Cell Tissue and Organ Culture 98(3):281-9 (Sep. 2009).
Gasson et al., "Metabolism of ferulic acid to vanillin. A bacterial gene of the enoyl-SCoA hydratase/isomerase superfamily encodes an enzyme for the hydration and cleavage of a hydroxycinnamic acid SCoA thioester," J Biol Chem. 273(7):4163-70 (Feb. 1998).
Grote et al., "JCat: a novel tool to adapt codon usage of a target gene to its potential expression host," Nucleic Acids Res. 33(Web Server Issue):W526-31 (Jul. 2005).
Hansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (May 2009).

(Continued)

Primary Examiner — Bratislav Stankovic
(74) Attorney, Agent, or Firm — McDonnell Boehnen Hulbert & Berghoff LLP

(57) ABSTRACT

The invention relates to methods for producing vanillin and related compounds. The methods involve use of a vanillin synthase capable of catalyzing side chain cleavage of ferulic acid to form vanillin. The invention also relates to host organisms expressing such vanillin synthases useful in the methods.

23 Claims, 12 Drawing Sheets
Specification includes a Sequence Listing.

(56) References Cited

OTHER PUBLICATIONS

Hebelstrup et al., "UCE: A uracil excision (USER (TM))-based toolbox for transformation of cereals," Plant Methods 6:15 (Jun. 2010).
Holme et al., "Cisgenic barley with improved phytase activity," Plant Biotechnol J. 10(2):237-47 (Feb. 2012).
Lambert et al., "Production of ferulic acid and coniferyl alcohol by conversion of eugenol using a recombinant strain of *Saccharomyces cerevisiae*," Flavour and Fragrance Journal 29(1):14-21 (Jan. 2014).
Narbad & Gasson, "Metabolism of ferulic acid via vanillin using a novel CoA-dependent pathway in a newly-isolated strain of Pseudomonas fluorescens," Microbiology 144(Pt 5):1397-405 (May 1998).
Paquette et al., "On the origin of family 1 plant glycosyltransferases," Phytochemistry 62(3):399-413 (Feb. 2003).
Podstolski et al., "Unusual 4-hydroxybenzaldehyde synthase activity from tissue cultures of the vanilla orchid *Vanilla planifolia*," Phytochemistry 61(6):611-20 (Nov. 2002).
Puigbo et al., "HEG-DB: a database of predict highly expressed genes in prokaryotic complete genomes under translational selection," Nucleic Acids Res. 36(Database issue):D524-7 (Oct. 2008).
Puigbo et al., "Optimizer: A web server for optimizing the codon usage of DNA sequences" Nucleic Acids Res. 35 (Web Server issue):W126-31 (Apr. 2007).
Radulovic et al., "Volatile constituents of Glechoma hirsuta Waldst. & Kit. and G. hederacea L. (*Lamiaceae*)," Bulletin of the Chemical Society of Ethiopia 24(1):67-76 (2010).
Schoch et al., "The meta-hydroxylation step in the phenylpropanoid pathway: a new level of complexity in the pathway and its regulation," Environ Chem Lett. 4:127-36 (Jun. 2006).
Sciubba et al., "Membrane-based solvent extraction of vanillin in hollow fiber," Desalination 241:357-64 (May 2009).
Shin et al., "Production of resveratrol from tyrosine in metabolically engineered *Saccharomyces cerevisiae*," Enzyme Microb Technol. 51(4):211-6 (Sep. 2012).
Supek & Vlahovicek, "Comparison of codon usage measures and their applicability in prediction of microbial gene expressivity," BMC Bioinformatics 6:182 (Jul. 2005).
Thompson et al., "Clustal W: improving the sensitivity of progressive multiple sequence alignment through sequence weighting, position-specific gap penalties and weight matrix choice," Nucleic Acids Res. 22(22):4673-80 (Nov. 1994).
Vannelli et al., "Production of p-hydroxycinnamic acid from glucose in *Saccharomyces cerevisiae* and *Escherichia coli* by expression of heterologous genes from plants and fungi," Metab Eng. 9(2):142-51 (Nov. 2007).
Wen-Jun & Forde, "Efficient transformation of *Agrobacterium* spp. By high voltage electroporation," Nucleic Acids Res. 17(20):8385 (Oct. 1989).
Zabkova et al., "Recovery of vanillin from lignin/vanillin mixture by using tubular ceramic ultrafiltration membranes," Journal of Membrane Science 301(1-2)221-37 (Sep. 2007).
Zhang et al., "Recovery of vanillin from aqueous solutions using macroporous adsorption resins," European Food Research and Technology 226(3):377-83 (Jan. 2008).
Zucchi et al., "Could Organic Solvents Be Used for the Alteration of Flux of Hydrophobic Intermediates through a Metabolic Pathway in Microorganisms?," J Microbiol. Biotechnol. 8(6):719-22 (Dec. 1998).
International Search Report issued by the International Searching Authority for International Application No. PCT/DK2013/050357; dated Feb. 3, 2014 (pp. 1-5).
Written Opinion the International Searching Authority for International Application No. PCT/DK2013/050357; dated Feb. 3, 2014 (pp. 1-10).
International Preliminary Report on Patentability issued by the International Bureau for International Application No. PCT/DK2013/050357; dated May 5, 2015 (pp. 1-11).
GenBank Accession No. AAB18637 (pp. 1-2).
GenBank Accession No. AEC09893.1 (pp. 1-3).
GenBank Accession No. AEE35608.1 (pp. 1-2).
GenBank Accession No. AEE35607.1 (pp. 1-2).
GenBank Accession No. AF106088.1 (AAD47195.1) (pp. 1-2).
GenBank Accession No. CAA75722 (pp. 1-2).
GenBank Accession No. CAA91228 (pp. 1-2).
GenBank Accession No. CAJ40778.1 (1 page).
GenBank Accession No. Q8GSM7 (pp. 1-3).
GenBank Accession No. Q9C5D7 (pp. 1-5).
GenBank Accession No. U37235.1 (pp. 1-2).
GenBank Accession No. XP_002332068 (pp. 1-2).
GenBank Accession No. AC005496 (pp. 1-28), accessed Feb. 21, 2017.
GenBank Accession No. BK006938.2 (pp. 1-483), accessed Feb. 20, 2017.
GenBank Accession No. NM_116337 (pp. 1-3), accessed Feb. 20, 2017.
GenBank Accession No. NM_126067 (pp. 1-3), accessed Feb. 20, 2017.
Priefert et al., "Biotechnological production of vanillin," Appl. Microbiol. Biotechnol. 56:296-314 (2001).
Overhage et al., "Biochemical and genetic analyses of ferulic acid catabolism in *Pseudomonas* sp. Strain HR199," Appl Environ Microbiol., 65(11):4837-47 (1999).
Overhage et al., "Highly efficient biotransformation of eugenol to ferulic acid and further conversion to vanillin in recombinant strains of *Escherichia coli*," Appl Environ Microbiol., 69(11):6569-76 (2003).

\* cited by examiner

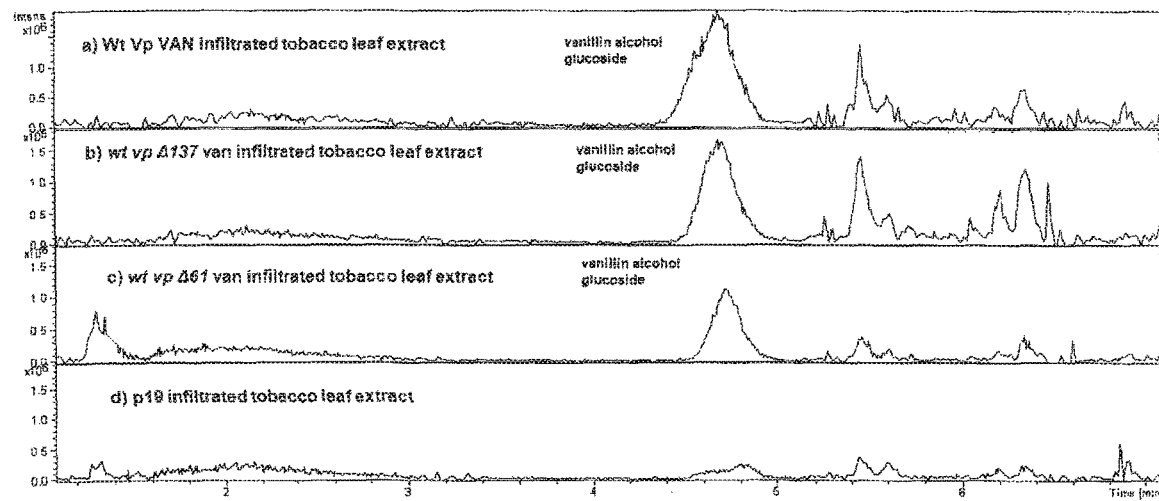
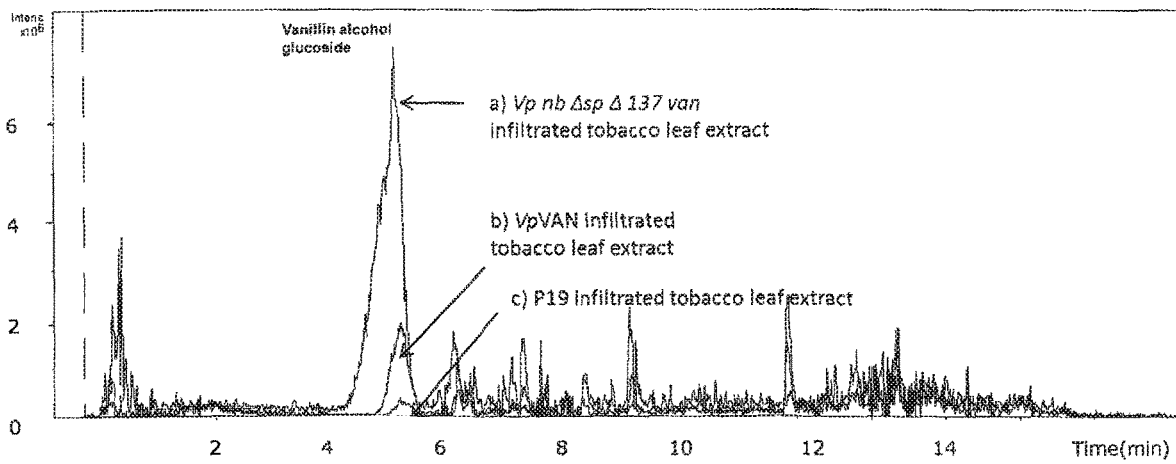
Fig. 7

```
                                                    20                          40
                                                     |                           |
Vanilla planifolia Vanillin synthase  MAAKLLFFLL  FLVSAL-SVA  LAG---FEED  NPIRSVTQRP  -DSIEPAILG  45
Nicotiana tabacum Cysteine protease   MSRFSLLLAL  VVAGGLFASA  LAGPATFADE  NPIRQVVSDG  LHELENAILQ  50
                          Consensus   M**L*L  ***LFA  LAGPATF***  NPIR*V**  L*E*AIL*
                                                    60                          80                         100
                                                     |                           |                           |
Vanilla planifolia Vanillin synthase  VLGSCRHAFH  FARFARRYGK  SYGSEEEIKK  RFGIFVENLA  FIRSTNRKDL  95
Nicotiana tabacum Cysteine protease   VVGKTRHALS  FARFAHRYGK  RYESVEEIKQ  RFEVFLDNLK  MIRSHNKKGL  100
                          Consensus   V*GRHA  FARFA*RYGK  *Y*S*EEIK*  RFFNL*  *IRS*N*K*L
                                                    120                         140
                                                     |                           |
Vanilla planifolia Vanillin synthase  SYTLGINQFA  DLTWEEFRTN  RLGAAQNCSA  TAHGNHRFVD  GVLPVTRDWR  145
Nicotiana tabacum Cysteine protease   SYKLGVNEFT  DLTWDEFRRD  RLGAAQNCSA  TTKGNLKVTN  VVLPETKDWR  150
                          Consensus   SY*LG*N*F*  DLTW*EFR  RLGAAQNCSA  TGN*****  *VLP*T*DWR
                                                    160                         180                         200
                                                     |                           |                           |
Vanilla planifolia Vanillin synthase  EQGIVSPVKD  QGSCGSCWTF  STTGALEAAY  TQLTGKSTSL  SEQQLVDCAS  195
Nicotiana tabacum Cysteine protease   EAGIVSPVKN  QGKCGSCWTF  STTGALEAAY  SQAFGKGISL  SEQQLVDCAG  200
                          Consensus   E*GIVSPVK*  QG*CGSCWTF  STTGALEAAY  *QGKSL  SEQQLVDCA*
                                                    220                         240
                                                     |                           |
Vanilla planifolia Vanillin synthase  AFNNFGCNGG  LPSQAFEYVK  YNGGIDTEQT  YPYLGVNGIC  NFKQENVGVK  245
Nicotiana tabacum Cysteine protease   AFNNFGCNGG  LPSQAFEYIK  SNGGLDTEEA  YPYTGKNGLC  KFSSENVGVK  250
                          Consensus   AFNNFGCNGG  LPSQAFEY*K  *NGG*DTE**  YPY*G*NG*C  *F**ENVGVK
                                                    260                         280                         300
                                                     |                           |                           |
Vanilla planifolia Vanillin synthase  VIDSINITLG  AEDELKHAVG  LVRPVSVAFE  VVKGFNLYKK  GVYSSDTCGR  295
Nicotiana tabacum Cysteine protease   VIDSVNITLG  AEDELKYAVA  LVRPVSIAFE  VIKGFKQYKS  GVYTSTECGN  300
                          Consensus   VIDS*NITLG  AEDELK*AV*  LVRPVS*AFE  V*KGF**YK*  GVY*S**CG*
                                                    320                         340
                                                     |                           |
Vanilla planifolia Vanillin synthase  DPMDVNHAVL  AVGYGVEDGI  PYWLIKNSWG  TNWGDNGYFK  MELGKNMCGV  345
Nicotiana tabacum Cysteine protease   TPMDVNHAVL  AVGYGVENGV  PYWLIKNSWG  ADWGDNGYFK  MEMGKNMCGI  350
                          Consensus   *PMDVNHAVL  AVGYGVE*G*  PYWLIKNSWG  **WGDNGYFK  ME*GKNMCG*
                                                    360
                                                     |
Vanilla planifolia Vanillin synthase  ATCASYPIVA  V*  357
Nicotiana tabacum Cysteine protease   ATCASYPVVA  --  360
                          Consensus   ATCASYP*VA  V*
```

Fig. 10

| | | | | 20 | | 40 | |
|---|---|---|---|---|---|---|---|
| Glechoma hederacea Vanillin synthase | MARLLLLLVG | VLIACAAGAR | AGSEFLAEDN | PIRQVVDGMH | ELESSILKAV | 50 |
| Vanilla planifolia Vanillin synthase | MAAKLLFFLL | FLVSALSVAL | AGFE---EDN | PIRSVTQRPD | SIEPAILGVL | 47 |
| Consensus | MALL** | *L******A* | AG*EFLAEDN | PIR*V**** | EIL*** | |

| | 60 | | 80 | | 100 | |
|---|---|---|---|---|---|---|
| Glechoma hederacea Vanillin synthase | GNSRRAFSFA | RFAHRYGKSY | ESSEEIQKRF | QVYSENLRMI | RSHNKKGLSY | 100 |
| Vanilla planifolia Vanillin synthase | GSCRHAFHFA | RFARRYGKSY | GSEEEIKKRF | GIFVENLAFI | RSTNRKDLSY | 97 |
| Consensus | G**R*AF*FA | RFA*RYGKSY | *S*EEI*KRF | **ENLI | RS*N*K*LSY | |

| | | 120 | | 140 | | |
|---|---|---|---|---|---|---|
| Glechoma hederacea Vanillin synthase | SMGVNEFSDL | TWDEFKKHRL | GAAQNCSATR | RGNHKLTSAI | LPDSKDWRES | 150 |
| Vanilla planifolia Vanillin synthase | TLGINQFADL | TWEEFRTNRL | GAAQNCSATA | HGNHRFVDGV | LPVTRDWREQ | 147 |
| Consensus | **G*N*F*DL | TW*EF***RL | GAAQNCSAT* | *GNH****** | LP***DWRE* | |

| | 160 | | 180 | | 200 | |
|---|---|---|---|---|---|---|
| Glechoma hederacea Vanillin synthase | GIVSPVKSQG | SCGSCWTFSS | TGALEAAYAQ | AFGKGISLSE | QQLVDCAGAF | 200 |
| Vanilla planifolia Vanillin synthase | GIVSPVKDQG | SCGSCWTFST | TGALEAAYTQ | LTGKSTSLSE | QQLVDCASAF | 197 |
| Consensus | GIVSPVK*QG | SCGSCWTFS* | TGALEAAY*Q | GKSLSE | QQLVDCA*AF | |

| | | 220 | | 240 | | |
|---|---|---|---|---|---|---|
| Glechoma hederacea Vanillin synthase | NNFGCNGGLP | SQAFEYIKYN | GGLMTEEAYP | YTGHDGECKY | SSENAAVQVL | 250 |
| Vanilla planifolia Vanillin synthase | NNFGCNGGLP | SQAFEYVKYN | GGIDTEQTYP | YLGVNGICNF | KQENVGVKVI | 247 |
| Consensus | NNFGCNGGLP | SQAFEY*KYN | GGTEYP | Y*G**G*C | EN**V*V* | |

| | 260 | | 280 | | 300 | |
|---|---|---|---|---|---|---|
| Glechoma hederacea Vanillin synthase | DSVNITLGAE | DELKHAVALV | RPVSVAFEVV | DGFRSYNGGV | YTSTTCGSDP | 300 |
| Vanilla planifolia Vanillin synthase | DSINITLGAE | DELKHAVGLV | RPVSVAFEVV | KGFNLYKKGV | YSSDTCGRDP | 297 |
| Consensus | DS*NITLGAE | DELKHAV*LV | RPVSVAFEVV | *GFYGV | Y*S*TCG*DP | |

| | | 320 | | 340 | | |
|---|---|---|---|---|---|---|
| Glechoma hederacea Vanillin synthase | MDVNHAVLAV | GYGVEGGVPY | WLIKNSWGAD | WGDQGYFKME | MGKNMCGVAT | 350 |
| Vanilla planifolia Vanillin synthase | MDVNHAVLAV | GYGVEDGIPY | WLIKNSWGTN | WGDNGYFKME | LGKNMCGVAT | 347 |
| Consensus | MDVNHAVLAV | GYGVE*G*PY | WLIKNSWG** | WGD*GYFKME | *GKNMCGVAT | |

| | 360 | |
|---|---|---|
| Glechoma hederacea Vanillin synthase | CASYPVVA*- | 359 |
| Vanilla planifolia Vanillin synthase | CASYPIVAV* | 357 |
| Consensus | CASYP*VAV* | |

Fig. 11

VANILLIN SYNTHASE

CROSS REFERENCE TO RELATED APPLICATIONS

This application is a U.S. National Phase of International Application No. PCT/DK2013/050357 filed Nov. 5, 2013, which claims priority from U.S. Provisional Application Ser. No. 1 61/722,513 filed Nov. 5, 2012. The entire disclosure contents of these applications are hereby incorporated by reference into the present application.

FIELD OF INVENTION

The present invention relates to methods for production of vanillin as well as to host organisms, such as microbial organisms or plants useful for such production.

BACKGROUND OF INVENTION

Vanilla is the world's most popular flavor compound and used in numerous commercial products including many foods. Natural vanilla is obtained from the pods of the epiphytic climbing orchids *Vanilla planifolia* Andrews and *Vanilla tahitensis* belonging to the genus *Vanilla* included in the order Orchidales within the monocotyledonous plants. Vanillin (3-methoxy-4-hydroxybenzaldehyde) is the main flavor compound in the vanilla extract obtained from fermented vanilla pods. In high concentrations, vanillin is toxic to living cells. In the pod it accumulates as the non-toxic phytoanticipin vanillin glucoside, which upon tissue damage is converted into the active defense compound. During fermentation and curing of the vanilla pods for use as flavor ingredient, a major part of the vanillin glucoside is hydrolyzed to provide free vanillin. The estimated total world market for vanillin is 10500 tons per annum. Production of natural vanillin from the vanilla pods is a laborious, slow and costly process. Production of 1 kilogram of vanillin requires approximately 500 kilograms of vanilla pods, corresponding to the pollination of approximately 40,000 flowers. Nowadays, only 3% of the global vanillin production is derived from vanilla pods. The vast majority is produced synthetically from different fossil hydrocarbons like eugenol or by acid hydrolysis of lignin. Biotechnological production of vanillin in microorganisms using heterologous expression of the genes encoding the pathway in vanilla orchids has not been achieved because none of the genes have been identified. Instead, vanillin has been produced in yeast, fungi, bacteria and in in vitro cell cultures by expressing genes from other organisms which encode enzymes that in combination would form vanillin from exogenously added substrates structurally related to vanillin.

Phenylalanine-derived volatiles are categorized as $C_6$-$C_1$, $C_6$-$C_2$, $C_6$-$C_3$ compounds based on their carbon skeleton. Both vanillin glucoside and p-hydroxybenzaldehyde glucoside, the two most abundant compounds found in mature vanilla pods, are $C_6$-$C_1$ compounds.

The two major aroma compounds in natural vanilla are p-hydroxybenzaldehyde and vanillin. Because p-hydroxybenzaldehyde contains some of the same structural elements of vanillin, it has been thought of as a precursor for vanillin. The pathway from vanillin has been postulated to constitute a metabolic grid of metabolites all derived from phenylalanine. US2003/0070188 describes methods for possible p-hydroxybenzaldehyde production in embryogenic cell cultures from *Vanilla planifolia*. One method described in US2003/0070188 takes advantage of a 4-hydroxy-benzaldehyde synthase (4-HBS), which is described as being capable of catalyzing chain shortening of p-coumaric acid to yield p-hydroxybenzaldehyde. The document further describes expression of 4-HBS in creeping bentgrass, however no information regarding the outcome of such expression is provided. It is also described that no 4-hydroxybenzaldehyde could be detected in yeast expressing 4-HBS.

Podstolski et al., 2002 describes that 4-hydroxy-benzaldehyde synthase (4-HBS) converts 4-coumaric acid non-oxidatively to 4-hydroxybenzaldehyde in the presence of a thiol reagent but with no co-factor requirement.

SUMMARY OF INVENTION

Accordingly, there is a need for methods for production of vanillin, and in particular for methods of producing vanillin in plants or microbial organisms.

The present invention provides an enzyme (herein designated vanillin synthase), which is capable of converting ferulic acid or a ferulic acid derivative to vanillin. This enzyme may be employed in the production of vanillin in a number of different host organisms as well as in vitro.

Thus, it is one aspect of the present invention to provide methods of producing vanillin from ferulic acid, wherein the methods involve use of a host organism expressing vanillin synthase, and wherein the ferulic acid may be added to said host organism or said host organism is capable of producing ferulic acid.

Accordingly, the invention provides methods of producing vanillin, said methods comprising
a) providing a microbial organism, wherein said microbial organism
  i. is capable of producing ferulic acid; and
  ii. comprises a heterologous nucleic acid encoding vanillin synthase (VpVAN) of SEQ ID NO:1 or a functional homologue thereof sharing at least 80% sequence identity therewith; and
b) cultivating said microbial organism in culture medium supporting growth of said microbial organism
c) Isolating vanillin and/or vanillin glucoside from the microbial organism and/or from the culture medium.

The invention also provides methods of producing vanillin, vanillyl alcohol, vanillin glucoside and/or vanillyl alcohol glucoside, said methods comprising
a) providing a microbial organism, wherein said microbial organism
  i. is capable of producing ferulic acid and/or a ferulic acid derivative; and
  ii. comprises a heterologous nucleic acid encoding a vanillin synthase, wherein said vanillin synthase is an enzyme capable of catalyzing side chain cleavage of ferulic acid to form vanillin; and
b) cultivating said microbial organism in culture medium supporting growth of said microbial organism
c) Isolating vanillin and/or vanillin glucoside from the microbial organism and/or from the culture medium.

It is also an aspect of the invention to provide microbial organisms, wherein said microbial organism
  i. is capable of producing ferulic acid; and
  ii. comprises a heterologous nucleic acid encoding vanillin synthase, wherein said vanillin synthase is an enzyme capable of catalyzing side chain cleavage of ferulic acid to form vanillin, e.g. VpVAN of SEQ ID NO:1 or a functional homologue thereof sharing at least 70%, such as at least 80% sequence identity therewith.

It is also an aspect of the invention to provide methods of producing vanillin said method comprising the steps of a) providing a microbial organism, wherein said microbial organism comprises a heterologous nucleic acid encoding vanillin synthase (VpVAN) of SEQ ID NO:1 or a functional homologue thereof sharing at least 80% sequence identity therewith; and
b) cultivating said microbial organism in the presence of ferulic acid and/or a ferulic acid derivative in culture medium supporting growth of said microbial organism; and
c) Isolating vanillin and/or vanillin glucoside from the microbial organism and/or from the culture medium.

It is also an aspect of the invention to provide methods of producing vanillin, vanillyl alcohol, vanillin glucoside and/or vanillyl alcohol glucoside, said method comprising the steps of
a) providing a microbial organism, wherein said microbial organism comprises a heterologous nucleic acid encoding vanillin synthase, wherein said vanillin synthase is an enzyme capable of catalyzing side chain cleavage of ferulic acid to form vanillin; and
b) cultivating said microbial organism in the presence of ferulic acid and/or a ferulic acid derivative in culture medium supporting growth of said microbial organism; and
c) Isolating vanillin, vanillyl alcohol, vanillyl alcohol glucoside and/or vanillin glucoside from the microbial organism and/or from the culture medium.

It is furthermore an aspect of the invention to provide methods for producing vanillin, said methods comprising
a) providing ferulic acid and/or a ferulic acid derivative
b) contacting said ferulic acid and/or ferulic acid derivative with a vanillin synthase, wherein said vanillin synthase is an enzyme capable of catalyzing side chain cleavage of ferulic acid to form vanillin, e.g.
(VpVAN) of SEQ ID NO:1 or a functional homologue thereof sharing at least 80% sequence identity therewith thereby producing vanillin.

It is also an aspect of the present invention to provide methods of producing vanillin, said methods comprising
a) Providing a plant comprising a heterologous nucleic acid encoding VpVAN of SEQ ID NO:1 or a functional homologue thereof sharing at least 80% sequence identity therewith; and
b) cultivating said plant; and
c) Isolating vanillin from the plant It is also of the present invention to provide methods of producing vanillin, vanilly alcohol, vanillin glucoside and/or vanillyl alcohol glucoside, said methods comprising
a) Providing a plant comprising a heterologous nucleic acid encoding a vanillin synthase, wherein said vanillin synthase is an enzyme capable of catalyzing side chain cleavage of ferulic acid to form vanillin; and
b) cultivating said plant; and
c) Isolating vanillin, vanillyl alcohol, vanillyl alcohol glucoside and/or vanillin glucoside from the plant.

It is furthermore an aspect of the invention to provide methods of producing animal feed, said methods comprising
a) Providing a plant comprising a heterologous nucleic acid encoding vanillin synthase, wherein said vanillin synthase is an enzyme capable of catalyzing side chain cleavage of ferulic acid to form vanillin, e.g. VpVAN of SEQ ID NO:1 or a functional homologue thereof sharing at least 80% sequence identity therewith; and
b) cultivating said plant; and
c) processing the plant into animal feed.

It is also an aspect of the invention to provide methods of producing food product, said method comprising
a) Providing a plant comprising edible parts, wherein said plant comprises a heterologous nucleic acid encoding vanillin synthase, wherein said vanillin synthase is an enzyme capable of catalyzing side chain cleavage of ferulic acid to form vanillin, e.g. VpVAN of SEQ ID NO:1 or a functional homologue thereof sharing at least 80% sequence identity therewith; and
b) cultivating said plant; and
c) harvesting said edible parts;
thereby obtaining a food product with vanillin palate.

The figure shows formation of vanillyl alcohol glucoside. (EIC 339—Extracted ion chromatogram m/z Vanillin alcohol glucoside mw+22) in extracts expressing vanillin synthase or truncated vanillin synthase.

FIG. 7B shows biological activity of a chimeric vanillin synthase compared to wild type VpVAN after transient expression in *Nicotiana benthamiana* leaves. The *Nicotiana benthamiana* has been transformed with nucleic acids encoding:
a) Chimeric vanillin synthase (vp nb Δsp Δ137van)(see Example 8)
b) Wt VpVAN (SEQ ID NO:1)
c) Negative control (p19 infiltrated tobacco leaf)

The figure shows formation of most vanillyl alcohol glucoside in a) (EIC 339—Extracted ion chromatogram m/z Vanillin alcohol glucoside mw+22) in extracts expressing vanillin synthase or truncated vanillin synthase.

Figure 8:
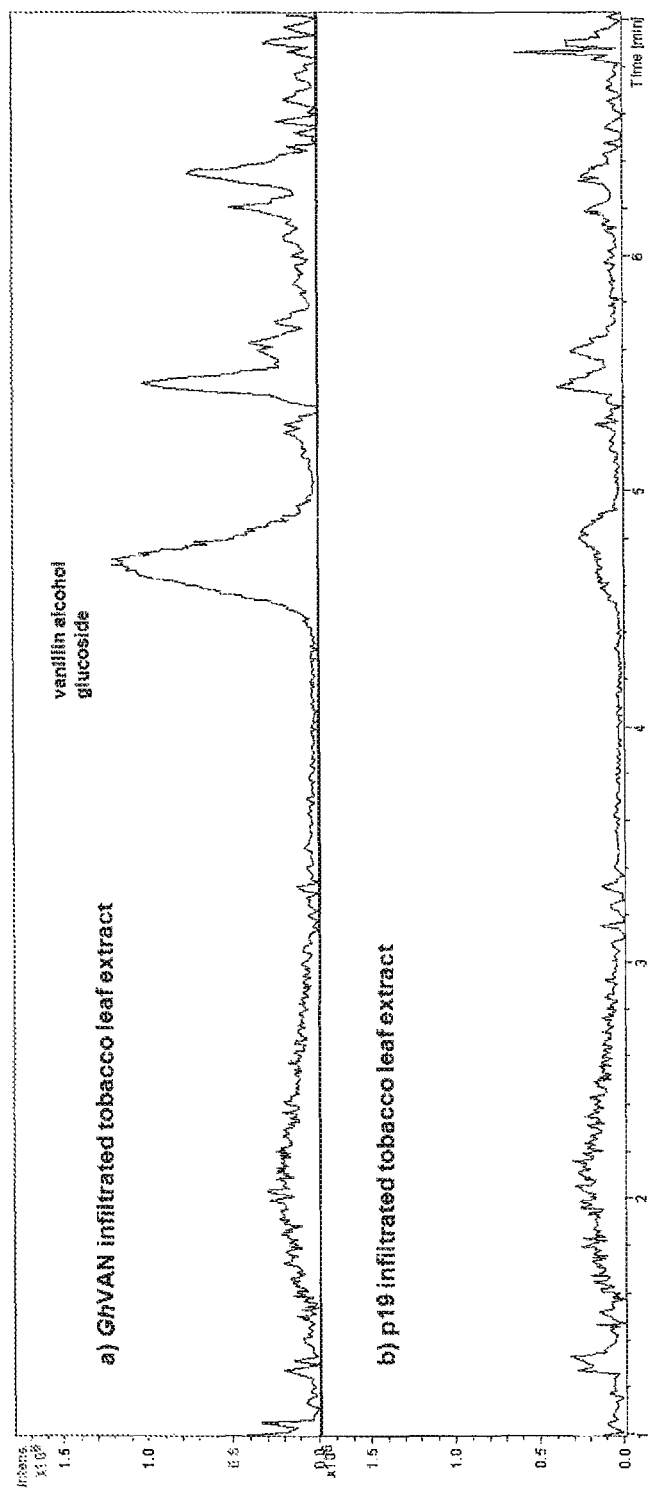

FIG. 8 shows biological activity of a vanillin synthase of *Glechoma hederacea* (GhVAN) after a transient expression in *Nicotiana benthamiana* leaves. The *Nicotiana benthamiana* has been transformed with nucleic acids encoding GhVAN (upper panel). Lower panel shows a negative control. The figure shows formation of vanillin alcohol glucoside.

Figure 9:
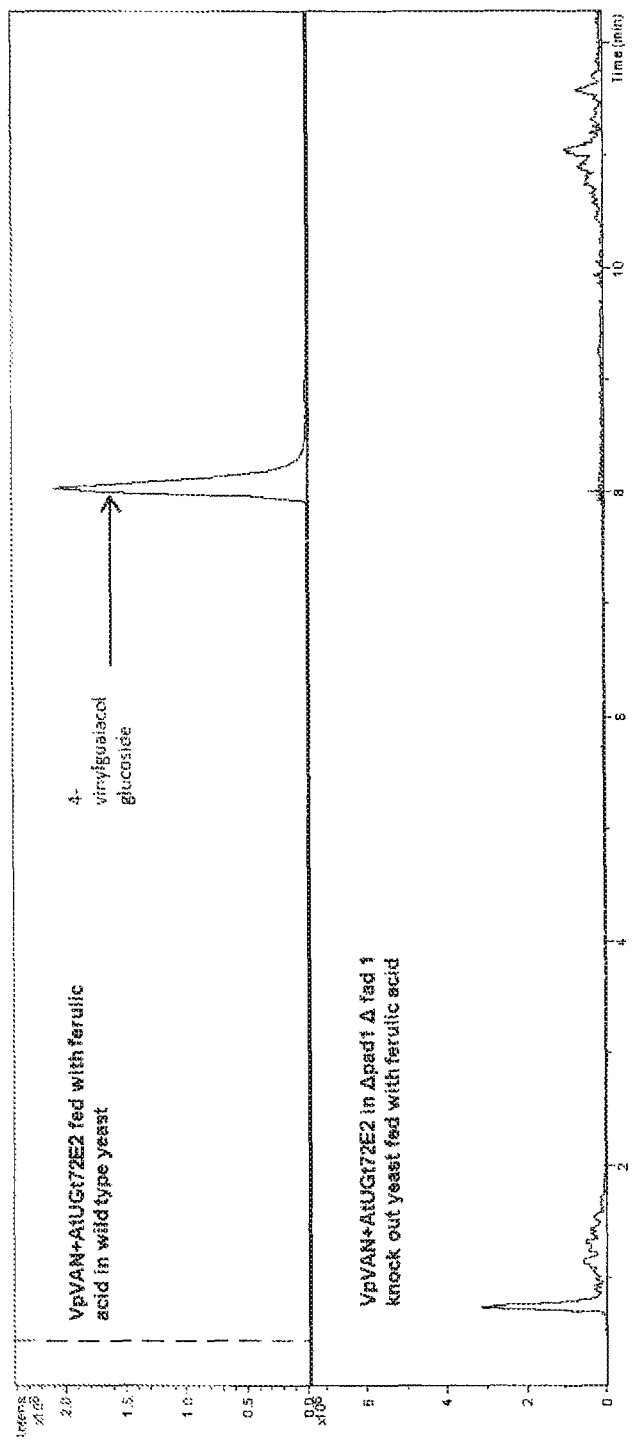

FIG. 9 shows 4-vinylguaiacol glucoside production in yeast expressing VpVAN (SEQ ID NO:1) and absence of this unwanted side product in yeast expressing VpVAN (SEQ ID NO:1) and lacking the pad1 and fad1 genes.

FIG. 10 shows an alignment between Cysteine protease of *Nicotiana benthamiana* (SEQ ID NO:22) and vanillin synthase of *Vanilla planifora* (VpVAN) (SEQ ID NO:1). The consensus sequence (SEQ ID NO:25) between the two sequences is given below. Non-conserved amino acids are marked by *.

FIG. 11 shows an alignment between Vanillin synthase of *Glechoma hederacea* (GhVAN) (SEQ ID NO:21) and vanillin synthase of *Vanilla planifora* (VpVAN) (SEQ ID NO:1). The consensus sequence (SEQ ID NO:26) between the two sequences is given below. Non-conserved amino acids are marked by *.

Figure 12:
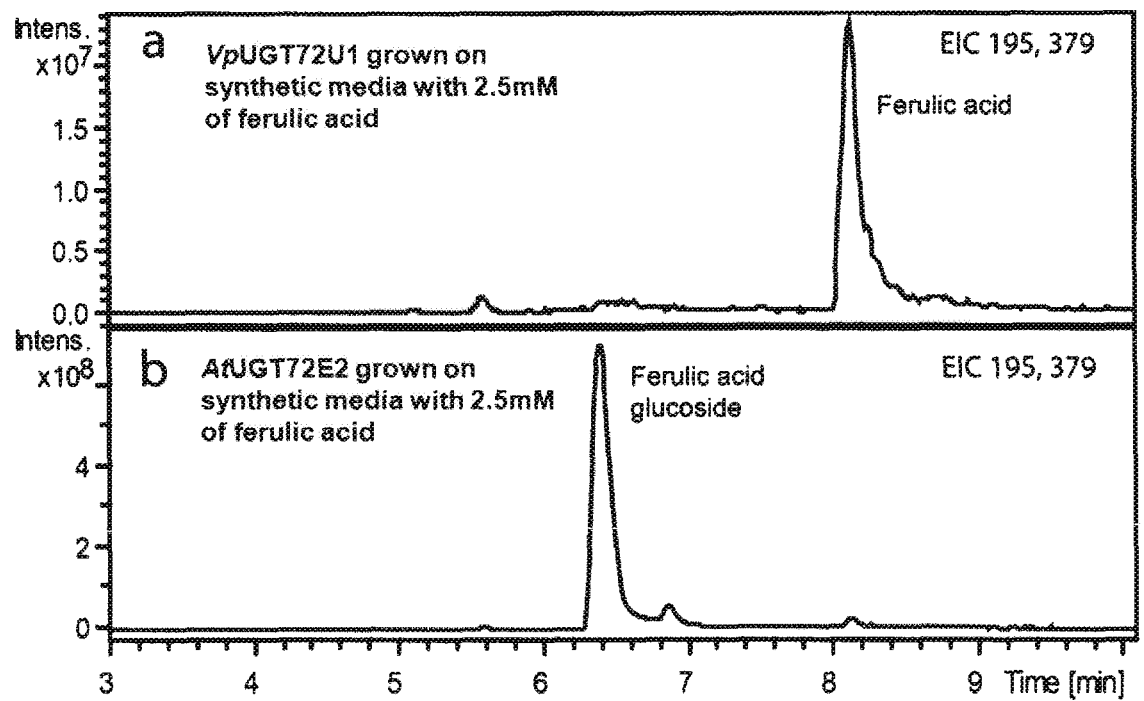

FIG. 12 shows that yeast cells expressing *Arabidopsis thaliana* UGT72E2 (SEQ ID NO:3) synthesizes ferulic acid glucoside when grown on synthetic media comprising 2.5 mM ferulic acid.

DETAILED DESCRIPTION OF INVENTION

Vanillin Synthase

The present invention relates to vanillin synthase and uses thereof. Thus, the invention in particular relates to methods of producing vanillin or vanillin glucoside using a host organism expressing vanillin synthase according to the invention. The host organism may be any of the microbial organisms described herein below in the section "Microbial organism" or the host organism may be any of the plants described herein below in the section "Plants". In general the host organism will contain a heterologous nucleic acid encoding vanillin synthase and optionally also one or more additional heterologous nucleic acids as described herein below.

The vanillin synthase according to the present invention is an enzyme capable of catalyzing side chain cleavage of ferulic acid to form vanillin. In particular, it is preferred that the vanillin synthase according to the present invention is an enzyme capable of catalyzing side chain cleavage of ferulic acid to form vanillin in vivo in a plant. It is also preferred that the vanillin synthase is an enzyme capable of catalyzing side chain cleavage of ferulic acid to form vanillin in vivo in microbial organisms.

The term vanillin as used herein refers to 3-methoxy-4-hydroxybenzaldehyde of the structure:

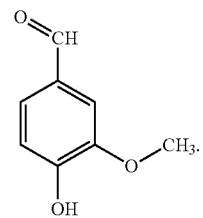 [SMILES: COc1cc(C=O)ccc1O]

The structure of ferulic acid is provided herein below in the section "ferulic acid".

The vanillin synthase to be used with the present invention may be vanillin synthase from any suitable origin, preferably the vanillin synthase is vanillin synthase of a plant, wherein said plant naturally produces vanillin, vanillyl alcohol, vanillin glycoside and/or vanillyl alcohol glycoside. Thus, in one embodiment the vanillin synthase is vanillin synthase of *Vanilla planifolia*.

Thus, a preferred vanillin synthase to be used with the invention is vanillin synthase of SEQ ID NO:1 or a functional homologue thereof sharing at least 70%, for example at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. Preferably, the vanillin synthase is vanillin synthase of SEQ ID NO:1. The sequence identity is preferably calculated as described herein below in the section "Sequence identity". A functional homologue of a vanillin synthase of a given sequence shares above-mentioned sequence identity and is capable of catalysing side chain cleavage of ferulic acid to form vanillin.

Additional useful vanillin synthases may be identified by any suitable method known to the skilled person, for example by a method comprising the steps of
  a) providing a plant, which produces vanillin, vanillyl alcohol, vanillin glycoside and/or vanillyl alcohol glycoside
  b) obtaining nucleic acids (e.g. DNA or cDNA) from said plant
  c) identifying a nucleic acid encoding a polypeptide having a sequence with at least 50%, such as at least 60%, for example at least 70% sequence identity to SEQ ID NO:1
  d) testing whether the polypeptide encoded by said nucleic acid is capable of catalysing side chain cleavage of ferulic acid to form vanillin.

The method may also comprise the steps of
  b) providing sequence information of nucleic acids from a plant, which produces vanillin, vanillyl alcohol, vanillin glycoside and/or vanillyl alcohol glycoside
  c) identifying a nucleic acid encoding a polypeptide having a sequence with at least 50%, such as at least 60%, for example at least 70% sequence identity to SEQ ID NO:1
  d) testing whether the polypeptide encoded by said nucleic acid is capable of catalysing side chain cleavage of ferulic acid to form vanillin.

If the polypeptide as tested in any of the steps d) described above is capable of catalysing side chain cleavage of ferulic acid to form vanillin, then said polypeptide is a vanillin synthase, which may be useful with the present invention.

Another vanillin synthase to be used with the invention is vanillin synthase of SEQ ID NO:21 or a functional homologue thereof sharing at least 70%, for example at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. Preferably, the vanillin synthase is vanillin synthase of SEQ ID NO:21. The sequence identity is preferably calculated as described herein below in the section "Sequence identity". A functional homologue of a vanillin synthase of a given sequence shares above-mentioned sequence identity and is capable of catalysing side chain cleavage of ferulic acid to form vanillin.

In addition to sharing above mentioned sequence identity, then it is also preferred that functional homologues retain as many of the amino acids conserved amongst different vanillin synthases. Thus, it is preferred that functional homologues of SEQ ID NO:1 comprises at least 90%, more preferably at least 95%, yet more preferably at least 98%, such as all of the amino acids of the consensus sequence of FIG. 11, for example at least 90%, more preferably at least 95%, yet more preferably at least 98%, such as all of the amino acids not marked by * in the alignment shown in FIG. 11. Similarly, it is preferred that functional homologues of SEQ ID NO:21 comprises at least 90%, more preferably at least 95%, yet more preferably at least 98%, such as all of the amino acids of the consensus sequence of FIG. 11, for example at least 90%, more preferably at least 95%, yet more preferably at least 98%, such as all of the amino acids not marked by * in the alignment shown in FIG. 11.

The vanillin synthase to be used with the present invention may also be vanillin synthase devoid of the signal peptide. This is in particular the case in embodiments of the invention where the nucleic acid sequence encoding vanillin synthase is introduced into microbial cells. Thus, in a preferred embodiment the vanillin synthase to be used with the present invention is vanillin synthase lacking all or at least part of the signal peptide, which directs the protein to the endoplasmatic reticulum of plants. Accordingly, the vanillin synthase may comprise at least or even consist of aa 22 to 356 of SEQ ID NO:1 or a functional homologue thereof sharing at least 80%, such as at least 85%, such as at least 90%, such as at least 95%, such as at least 98% sequence identity therewith. In one embodiment, the vanillin synthase to be used with the present invention is vanillin synthase of SEQ ID NO:17 or a functional homologue thereof sharing at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

The vanillin synthase to be used with the present invention may also be a truncated vanillin synthase, which is capable of catalyzing side chain cleavage of ferulic acid to form vanillin. Thus, the vanillin synthase may lack one or more N-terminal amino acids, for example the vanillin synthase maybe
  a) vanillin synthase of SEQ ID NO:1 lacking in the range of 1 to 150 of the most N-terminal amino acids
  b) vanillin synthase of SEQ ID NO:1 lacking in the range of 21 to 137 of the most N-terminal amino acids
  c) Vanillin synthase of SEQ ID NO:1 lacking in the range of 120 to 140 of the most N-terminal amino acids
  d) Vanillin synthase of SEQ ID NO:1 lacking in the range of 130 to 140 of the most N-terminal amino acids
  e) Vanillin synthase of SEQ ID NO:21 lacking in the range of 21 to 140 of the most N-terminal amino acids
  f) Vanillin synthase of SEQ ID NO:1 lacking the 21 most N-terminal amino acids
  g) Vanillin synthase of SEQ ID NO:1 lacking the 61 most N-terminal amino acids
  h) Vanillin synthase of SEQ ID NO:1 lacking the 137 most N-terminal amino acids
  i) Vanillin synthase of SEQ ID NO:21 lacking the 21 most N-terminal amino acids
  j) Vanilline synthase of SEQ ID NO:21 lacking the 140 most N-terminal amino acid
  k) a functional homologue of any of a) to j) sharing at least 70%, for example at least 80%, such as at least 85%, such as at least 90%, such as at least 95%, for example at least 98% sequence identity therewith, wherein said functional homologue is capable of catalysing side chain cleavage of ferulic acid to form vanillin.

It is also comprised within the invention that the truncated vanillin synthase may be
  a) vanillin synthase comprising or consisting of aa 22 to 356 of SEQ ID NO:1 b) vanillin synthase comprising or consisting of aa 138 to 356 of SEQ ID NO:1
c) vanillin synthase comprising or consisting of aa 22 to 359 of SEQ ID NO:21
d) vanillin synthase comprising or consisting of aa 141 to 359 of SEQ ID NO:21
e) a functional homologue of any of a) to d) sharing at least 70%, for example at least 80%, such as at least 85%, such as at least 90%, such as at least 95%, for example at least 98% sequence identity therewith, wherein said functional homologue is capable of catalysing side chain cleavage of ferulic acid to form vanillin.

In another embodiment of the invention the vanillin synthase is a chimeric protein containing sequences from a naturally occurring vanillin synthase as well as other sequences. In such embodiments of the invention the vanillin synthase may be a polypeptide of the following formula:

[Signal peptide]-X-[cleavage site]-[truncated vanillin synthase]

The signal peptide may be any signal peptide. The skilled person will be able to identify a signal peptide, for example using the SignalP 4.1. software, which is readily available from Center for Biological Sequence analysis at the Technical University of Denmark.

In particular, it is preferred that the signal peptide is a signal peptide endogenous to the host organism (i.e. the host organism containing a heterologous nucleic acid encoding said vanillin synthase). More preferably, the signal peptide is a signal peptide from a cysteine protease endogenous to the host organism. Even more preferably, the signal peptide is a signal peptide from a cysteine protease belonging to the Clan CA, more preferably to the Family C1, even more preferably to the Subfamily A, wherein said cysteine protease is endogenous to the host organism. Said clan, family and subfamily is as defined by MEROPS Database. For example the cysteine protease may be a cysteine protease belonging to the class of aleurain cysteine proteases. Aforementioned regarding the signal peptide being from a cysteine protease is in particular applicable in embodiments of the invention where the host organism is a plant.

The signal peptide may thus be identified by a method comprising the steps of
a) providing nucleic acids encoding polypeptides or sequence information of nucleic acids encoding polypeptides or sequence information of polypeptides of the host organism
b) identifying a polypeptide having a sequence identity with SEQ ID NO:1 of at least 50%, such as at least 60%, for example at least 70%, and which is a cysteine protease
c) identifying the signal peptide of said cysteine protease, for example using the SignalP 4.1. software
thereby identifying the signal peptide.

X may be any linker sequence linking the signal peptide and the cleavage site. In one embodiment said linker sequence X may be a sequence from a naturally occurring vanillin synthase. Thus, for example X may be aa 22 to 134 of SEQ ID NO:1 or a functional homologue thereof sharing at least 70%, for example at least 80%, such as at least 85%, such as at least 90%, such as at least 95%, for example at least 98% sequence identity therewith over the entire length.

The cleavage site may be any protease cleavage site. In particular, it is preferred that the cleavage site is endogenous to the host organism. More preferably, the cleavage site is a cleavage site from a cysteine protease endogenous to the host organism. Even more preferably, the cleavage site is a cleavage site from a cysteine protease belonging to the Clan CA, more preferably to the Family C1, even more preferably to the Subfamily A, wherein said cysteine protease is endogenous to the host organism. Said clan, family and subfamily is as defined by MEROPS Database. For example the cysteine protease may be a cysteine protease belonging to the class of aleurain cysteine proteases. Aforementioned regarding the cleavage site being from a cysteine protease is in particular applicable in embodiments of the invention where the host organism is a plant.

The cleavage site may be identified by a method comprising the steps of
a) providing nucleic acids encoding polypeptides or sequence information of nucleic acids encoding polypeptides or sequence information of polypeptides of the host organism
b) identifying a polypeptide having a sequence identity with SEQ ID NO:1 of at least 50%, such as at least 60%, for example at least 70%, and which is a cysteine protease
c) preparing an alignment between SEQ ID NO:1 and said polypeptide identified under b)
d) identifying the amino acids of said polypeptide corresponding to amino acids 135 to 141 of SEQ ID NO:1, wherein the amino acids corresponding to amino acids 135 to 141 of SEQ ID NO:1 are the cleavage site.

The truncated vanillin synthase may be any of the truncated vanillin synthases described herein above. In particular the truncated vanillin synthase may comprise or consists of aa 142 to 356 of SEQ ID NO:1 or a functional homologue thereof sharing at least 70%, for example at least 80%, such as at least 85%, such as at least 90%, such as at least 95%, for example at least 98% sequence identity therewith over the entire length.

The heterologous nucleic acid may be any heterologous nucleic acid encoding a vanillin synthase described in this section. For example the heterologous nucleic acid may be a nucleic acid comprising SEQ ID NO:2 or a nucleic acid capable of hybridizing to the complementary sequence of SEQ ID NO:2.

However, in preferred embodiments of the invention, the heterologous nucleic acid encoding vanillin synthase has been fully or partly codon optimized for the particular microbial organism comprising the heterologous nucleic acid. Several software packages are publicly available for this purpose for example "Optimizer", which is described in Puigbò et al., 2007, OPTIMIZER: A web server for optimizing the codon usage of DNA sequences, *Nucleic Acids Research*, 35:W126-W131 and Puigbò et al., 2008, HEG-DB: a database of predict highly expressed genes in prokaryotic complete genomes under translational selection, *Nucleic Acids Research*. 36:D524-7 or "JCat", which is described in Grote et al., 2005, JCat: a novel tool to adapt codon usage of a target gene to its potential expression host, Nucleic Acids Research, Volume 33, Issue suppl 2, Pp. W526-W531 or "INCA" as described in Supek F and Vlahovicek K: Comparison of codon usage measures and their applicability in prediction of microbial gene expressivity; *BMC Bioinformatics* (2005) 6:182.

Thus, in embodiments of the invention relating to use of microbial organisms, the heterologous nucleic acid encoding vanillin synthase may be codon optimised for the particular microbial organism used. Thus, the heterologous nucleic acid encoding vanillin synthase may be partly codon optimised for the particular microbial organism used, or the heterologous nucleic acid encoding vanillin synthase may be fully codon optimised for the particular microbial organism used. For example, in embodiments of the invention relating to use of yeast, such as *S. cerevisiae*, then the heterologous nucleic acid encoding vanillin synthase may be codon optimised for use in yeast, such as for use in *S. cerevisiae*, for example the heterologous nucleic acid encoding vanillin synthase may comprise or even consist of SEQ ID NO:18.

Methods

In one aspect, the present invention relates to methods for the production of vanillin. The methods involve use of vanillin synthase, which may be any of the vanillin synthases described herein above in the section "vanillin synthase". In general the methods involve use of a host organism expressing a vanillin synthase.

Thus, in one embodiment the invention relates to methods of producing vanillin, vanillyl alcohol and/or glucosides thereof, said method comprising the steps of a) Providing a microbial organism, wherein said microbial organism
  i. is capable of producing ferulic acid and/or a ferulic acid derivative; and
  ii. comprises a heterologous nucleic acid encoding vanillin synthase, wherein said vanillin synthase is an enzyme capable of catalyzing side chain cleavage of ferulic acid to form vanillin, e.g. (VpVAN) of SEQ ID NO:1 or a functional homologue thereof sharing at least 70%, such as at least 80% sequence identity therewith; and
b) cultivating said microbial organism in culture medium supporting growth of said microbial organism
c) Isolating vanillin, vanillyl alcohol, vanillyl alcohol glucoside and/or vanillin glucoside from the microbial organism and/or from the culture medium.

In this embodiment the microbial organism may be any of the microbial organisms described herein below in the section "microbial organism". Said microbial organism is capable of producing ferulic acid or a ferulic acid derivative (e.g. ferulic acid glucoside). Preferably, the microbial organism is capable of producing ferulic acid. This may be achieved in various ways. For example the microbial organism may contain nucleic acid sequences encoding one or more enzymes involved in synthesis of ferulic acid, such as any of the enzymes described herein below in the section "Enzymes involved in synthesis of ferulic acid". The nucleic acid encoding vanillin synthase may encode any of the vanillin synthases described herein above in the section "Vanillin synthase". It is preferred that the methods are methods of preparing vanillin.

In another embodiment the invention relates to methods of producing vanillin, vanillyl alcohol and/or glucosides thereof, said methods comprising the steps of a) providing a microbial organism, wherein said microbial organism comprises a heterologous nucleic acid encoding vanillin synthase, wherein said vanillin synthase is an enzyme capable of catalyzing side chain cleavage of ferulic acid to form vanillin, e.g. (VpVAN) of SEQ ID NO:1 or a functional homologue thereof sharing at least 70%, such as at least 80% sequence identity therewith; and
b) cultivating said microbial organism in the presence of ferulic acid or a ferulic acid derivative in culture medium supporting growth of said microbial organism
c) Isolating vanillin and/or vanillin glucoside from the microbial organism and/or from the culture medium.

In this embodiment the microbial organism may be any of the microbial organisms described herein below in the section "microbial organism". The nucleic acid encoding vanillin synthase may encode any of the vanillin synthases described herein above in the section "Vanillin synthase". The culture medium may comprise ferulic acid originating from any suitable source, and/or the culture medium may comprise a ferulic acid derivative, e.g. ferulic acid glucoside. In particular the ferulic acid may be provided in any of the ways described herein below in the section "Ferulic acid". Preferably, the method is a method of producing vanillin.

In yet another embodiment, the invention relates to methods of producing vanillin, said method comprising the steps of a) Providing a microbial organism, wherein said microbial organism
  i. is capable of producing ferulic acid and/or a ferulic acid derivative; and
  ii. comprises a heterologous nucleic acid encoding vanillin synthase, wherein said vanillin synthase is an enzyme capable of catalyzing side chain cleavage of ferulic acid to form vanillin, e.g. (VpVAN) of SEQ ID NO:1 or a functional homologue thereof sharing at least 70%, such as at least 80% sequence identity therewith; and
  iii. is capable of glucosylating vanillin; and
b) cultivating said microbial organism in culture medium supporting growth of said microbial organism
c) Isolating vanillin glucoside from the microbial organism and/or from the culture medium; and
d) Deglucosylating said vanillin glucoside.

In this embodiment, the microbial organism may be any of the microbial organisms described herein below in the section "microbial organism". Said microbial organism is capable of producing ferulic acid or a ferulic acid derivative (e.g. ferulic acid glucoside).

Preferably the microbial organism is capable of producing ferulic acid. This may be achieved in various ways. For example the microbial organism may contain nucleic acids encoding one or more enzymes involved in synthesis of ferulic acid, such as any of the enzymes described herein below in the section "Enzymes involved in synthesis of ferulic acid". Said microbial organism is also capable of glucosylating vanillin. This may be achieved in various ways. For example the microbial organism may contain a nucleic acid sequence encoding a glucosyl transferase, preferably the microbial organism contains a nucleic acid sequence encoding any of the glucosyl transferases described herein below in the section "Glycosyl transferases". The nucleic acid encoding vanillin synthase may encode any of the vanillin synthases described herein above in the section "Vanillin synthase". Deglucosylating said vanillin glucoside may be performed as described herein below.

In a further embodiment the invention relates to a method of producing vanillin, wherein the method comprises the steps of a) providing a microbial organism, wherein said microbial organism
  i. comprises a heterologous nucleic acid sequence encoding vanillin synthase, wherein said vanillin synthase is an enzyme capable of catalyzing side chain cleavage of ferulic acid to form vanillin, e.g. (VpVAN) of SEQ ID NO:1 or a functional homologue thereof sharing at least 80% sequence identity therewith; and
  iii. is capable of glucosylating vanillin; and b) cultivating said microbial organism in the presence of ferulic acid and/or ferulic acid derivative in culture medium supporting growth of said microbial organism c) Isolating vanillin glucoside from the microbial organism and/or from the culture medium; and d) Deglucosylating said vanillin glucoside.

In this embodiment, the microbial organism may be any of the microbial organisms described herein below in the section "microbial organism". The nucleic acid encoding vanillin synthase may encode any of the vanillin synthases described herein above in the section "Vanillin synthase". The culture medium may comprise ferulic acid and/or ferulic acid derivative (e.g. ferulic acid glucoside). Preferably the culture medium contains ferulic acid. Said ferulic acid may originate from any suitable source, in particular the ferulic acid may be provided in any of the ways described herein below in the section "Ferulic acid". Deglucosylating said vanillin glucoside may be performed as described herein below.

The microbial organism may be cultivated in any culture medium suitable for cultivating microbial organism. The skilled person will be able to select a suitable culture medium depending on the particular microbial organism. In particular, the growth conditions should be selected so that the vanillin synthase is expressed in said microbial organism. The microbial organism may be grown in a fed batch or continuous process. Typically, the microbial organism is grown in a fermentor at a defined temperature(s) for a desired period of time. Depending on the particular microbial organism used in the method, other heterologous nucleic acids encoding enzymes involved in synthesis of ferulic acid and/or glucoside transferases may also be present and expressed.

In some embodiments, vanillin or vanillin glucoside can be produced using whole cells that are fed ferulic acid and/or a ferulic acid derivative, which may be provided in any of the ways described herein below in the section "Ferulic acid". The ferulic acid be contained in the culture medium, it may be fed during cell growth or after cell growth. Preferably, the culture medium comprises ferulic acid. The microbial organism may be grown in suspension or immobilized. In embodiments of the invention where the microbial organism is bacteria or fungi, such as yeast, then preferably the microbial organism is grown in suspension.

In one embodiment of the invention it is preferred that the culture medium does not contain high levels of coumaric acid, for example the culture medium may contain at the most 1 mM, such as at the most 0.5 mM, for example at the most 0.01 mM, such as no detectable coumaric acid.

In one embodiment of the invention it is preferred that the vanillin is produced under conditions, which are not too reducing. According, in one embodiment it is preferred that the culture medium comprises less than 5 mM, preferably less than 3 mM DTT. In embodiments of the invention where vanillin is prepared in vitro it is preferred that ferulic acid and/or the ferulic acid derivative is incubated with vanillin synthase in the presence of at the most 5 mM, preferably at the most 3 mM DTT.

The method relates to production of vanillin or vanillin glucoside, said vanillin glucoside is preferably vanillin beta-D-glucoside. The amount of vanillin or vanillin glucoside produced can be from about 1 mg/l to about 1,500 mg/L, or higher. For example, about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L of vanillin or vanillin glucoside, or about 250 to about 5,000 mg/L, about 1,000 to about 15,000 mg/L, or about 2,000 to about 10,000 mg/L, about 2000 to about 50000 mg/L or even from about 2,000 to about 100000 mg/L, or even from about 5000 to 200,000 mg/L can be produced. In general, longer culture times will lead to greater amounts of product. Thus, the microbial organism can be cultured for from 1 day to 7 days, from 1 day to 5 days, from 3 days to 5 days, about 3 days, about 4 days, or about 5 days.

After the microbial organism has been grown in culture for the desired period of time, vanillin, vanillyl alcohol, vanillyl alcohol glucoside and/or vanillin glucoside can then be recovered from the culture using any useful techniques known in the art. For example, methods for isolating vanillin and/or vanillin glucoside may comprise the percolation technique or supercritical carbon dioxide extraction and reverse osmosis for concentration. Vanillin and/or vanillin glucoside may also be recovered by methods involving isolation and purification by extraction, vacuum distillation and multi-stage re-crystallization from aqueous solutions and ultrafiltration (e.g. as described by Boddeker, et al. (1997) J. Membrane Sci. 137:155-158; Borges da Silva, et al. (2009) Chem. Eng. Des. 87:1276-1292). Two-phase extraction processes, employing either sulphydryl compounds, such as dithiothreitol, dithioerythritol, glutathione, or L-cysteine (U.S. Pat. No. 5,128,253), or alkaline KOH solutions (WO 94/13614), may also be used in the recovery of vanillin and/or vanillin glucoside as well as for its separation from other aromatic substances. Vanillin adsorption and pervaporation from bioconverted media using polyether-polyamide copolymer membranes may also be employed for isolating vanillin and/or vanillin glucoside (e.g. as described by Boddeker, et al. (1997) supra; or Zucchi, et al. (1998) J. Microbiol. Biotechnol. 8: 719-'22). Macroporous adsorption resins with crosslinked-polystyrene framework may also been used to recover dissolved vanillin and/or vanillin glucoside from aqueous solutions (Zhang, et al. (2008) Eur. Food Res. Technol. 226:377-383). Ultrafiltration and membrane contactor (MC) techniques may also be useful to recover vanillin and/or vanillin glucoside (Zabkova, et al. (2007) J. Membr. Sci. 301:221-237; Scuibba, et al. (2009) Desalination 241:357-364). Alternatively, conventional techniques such as percolation or supercritical carbon dioxide extraction and reverse osmosis for concentration could be used.

If the recombinant host is a plant or plant cells, vanillin or vanillin glucoside can be extracted from the plant tissue using various techniques known in the art.

In some embodiments, the vanillin or vanillin glucoside is isolated and purified to homogeneity (e.g., at least 90%, 92%, 94%, 96%, or 98% pure). In other embodiments, the vanillin or vanillin glucoside is provided as an extract from a microbial organism. In this respect, vanillin or vanillin glucoside may be isolated, but not necessarily purified to homogeneity.

Extracts of isolated, and optionally purified, vanillin or vanillin glucoside for example find use in flavoring consumables such as food products, dietary supplements, nutraceuticals, pharmaceutical compositions, dental hygienic compositions, and cosmetic products.

In embodiments of the invention, wherein the microbial organism is capable of glucosylating vanillin, then the method may frequently also contain a step of deglucosylating said vanillin glucoside. This step may be performed prior to isolation of the vanillin glucoside or subsequently to isolation of vanillin glucoside.

This may be done by chemical hydrolysis according to known methods in the art or enzymatically by e.g. use of an enzyme with glucosidase activity. In particular a beta-glucosidase may be used. Numerous suitable beta-glycosidases are known to the skilled person. Deglucosylation can e.g. be achieved first by recovering vanillin glucoside for instance by extracting it in a suitable solvent, e.g. methanol, or by collecting it after excretion from the producing microbial organism or plant. Secondly, the glucosylated intermediate may be purified and exposed to a beta-glucosidase in vitro or to an adequate chemical hydrolysis.

The glucosidase may be provided in various forms, for example the glucosidase may be provided in form of a microbial organism expressing said glucosidase and preferably excreting said glucosidase. Such a microbial organism may be co-cultured together with the microbial organism comprising the vanillin synthase of the invention. The glucosidase may also be provided in the form of an extract of an organism expressing the glucosidase. Said extract may be a crude extract or a partly purified extract. The glucosidase may also be provided as the purified enzyme. In embodiments where the glucosidase is provided as an extract, a crude extract or as a purified enzyme, then the glucosidase may be added directly to the culture medium during cultivation of the microbial organism comprising the vanillin synthase. However, preferably it is added after cultivation. Thus it may be added directly to the culture medium after cultivation of the microbial organism comprising the vanillin synthase or it may be added to partly purified vanillin glucoside or even to purified vanillin glucoside. Thus, the isolated vanillin glucoside may be treated with said extract, said partly purified extract or said purified glucosidase.

Glucosylation of vanillin may also facilitate isolation: Hydrophobic impurities in the culture medium accumulating vanillin glucoside can be removed by two phase partitioning where vanillin glucoside will partition to the aqueous phase while hydrophobic impurities may partition to the organic phase. Following degycosylation, for example by beta-glucosidase treatment, the two phase partitioning process may be repeated to achieve removal of hydrophilic contaminants.

Thus, the purification may comprise the steps of:
a) Obtaining culture medium and/or extract of the microbial organism comprising vanillin glucoside after cultivation and/or extract of a plant comprising vanillin glucoside; and
b) Contacting and mixing said culture medium or extract with an organic phase
c) Separating the aqueous phase from the organic phase; and
d) Discarding the organic phase; and
e) Deglucosylating the vanillin glucoside, e.g. by glucosidase treatment, such as glucosidase treatment as described herein above, thereby obtaining a liquid comprising vanillin; and
f) Contacting and mixing said liquid comprising vanillin with an organic phase; and
g) Recovering the organic phase, which comprises vanillin; and
h) Optionally further purifying vanillin from said organic phase The organic phase may be any useful organic phase, e.g. the organic phase may be composed of hexane, diethylether, ethylacetate or chloroform.

In one embodiment the invention relates to methods of producing vanillin, vanillyl alcohol and/or glucosides thereof, said method comprising
a) Providing a plant comprising a heterologous nucleic acid encoding VpVAN of SEQ ID NO:1 or a functional homologue thereof sharing at least 80% sequence identity therewith; and
b) cultivating said plant; and
c) Isolating vanillin, vanillyl alcohol and/or glucosides thereof from the plant.

In this embodiment the plant may be any of the plants described herein below in the section "Plant". The nucleic acid encoding vanillin synthase may encode any of the vanillin synthases described herein above in the section "Vanillin synthase". In a preferred embodiment the method is a method for producing vanillin.

In another embodiment the invention relates to methods of producing vanillin glucosides, said method comprising
a) Providing a plant comprising a heterologous nucleic acid encoding VpVAN of SEQ ID NO:1 or a functional homologue thereof sharing at least 80% sequence identity therewith; and
b) cultivating said plant; and
c) Isolating vanillin glucosides from the plant,
d) Deglucosylating said vanillin glucoside.

The plant may be cultivated in any manner suitable for culturing the specific plant. The skilled person will be able to select suitable conditions for cultivating a particular plant.

The vanillin, vanillyl alcohol and/or vanillin glucoside may be isolated from any useful part of the plant, for example from the leaves, from the fruits, from the seeds, from the roots, or from the stems. Frequently, vanillin, vanillyl alcohol or vanillin glucoside will be isolated from leaves, seeds or fruits of the plant. For example in embodiments of the invention, where the plant is *Nicotiana tabacum*, then vanillin or vanillin glucoside may be isolated from the leaves. The isolation in general comprises a step of extraction, which may then optionally be followed by one or more purification steps, for example any of the purification steps described herein above in this section. Deglucosylation of vanillin glucoside may also be performed as described herein above in this section.

In one embodiment it is preferred that said plant producing at least 3 times, such as at least 4 times, for example at least 5 times, such as at least 10 times more vanillin compared to an identical plant, which does not comprise said heterologous nucleic acid encoding vanillin synthase.

Extracts comprising vanillin or isolated vanillin prepared as described by the present invention e.g. find use in flavouring consumables, such as food products, dietary supplements, nutraceuticals, pharmaceutical compositions, dental hygienic compositions and cosmetic products. Useful examples of such consumables are described in WO2013/022881 in the sections [0030] to [0046]. WO2013/022881 is incorporated by reference herein.

Microbial Organism

In one aspect the present invention relates to microbial organisms comprising a heterologous nucleic acid encoding vanillin synthase, which may be any of the vanillin synthases described herein above in the section "vanillin synthase" as well as use thereof in the production of vanillin and/or vanillin glucoside.

The microbial organism may in addition to the heterologous nucleic acid encoding vanillin synthase also comprise additional heterologous nucleic acids, for example heterologous nucleic acids encoding one or more enzymes involved in synthesis of ferulic acid (for example any of the enzymes involved in the synthesis of ferulic acid described herein below in the section "Enzymes involved in synthesis of ferulic acid") or a glucosyl transferase (for example any of the glucosyl transferases described herein below in the section "Glucosyl transferase").

It will be appreciated that the various genes and modules discussed herein can be present in two or more microbial organisms rather than a single microbial organism. Thus, for example one microbial organism may contain one or more heterologous nucleic acid encoding an enzyme involved in the synthesis of ferulic acid, rendering said microbial organism capable of producing ferulic acid, whereas another microbial organism may comprise the heterologous nucleic acid encoding vanillin synthase. When a plurality of microbial organisms is used, they can be grown in a mixed culture to produce vanillin and/or vanillin glucoside. In such cases the co-expression of suitable transporters may be advantageous to export intermediates into the growth medium and to facilitate uptake into the microbial organism producing vanillin or vanillin glucoside.

The microbial cell of the present invention can be any cell suitable for expression of heterologous nucleic acids. In one embodiment the microbial cell of the invention is a eukaryotic cell. In another embodiment the host cell is a prokaryotic cell.

In a preferred embodiment, the host cell is a fungal cell such as a yeast or filamentous fungus. In particular the host cell may be a yeast cell.

In a further embodiment the yeast cell is selected from the group consisting of *Saccharomyces cerevisiae, Schizosaccharomyces pombe, Yarrowia lipolytica, Candida glabrata, Ashbya gossypii, Cyberlindnera jadinii*, and *Candida albicans*.

In general, yeasts and fungi are excellent microbial cells to be used with the present invention. They offer a desired ease of genetic manipulation and rapid growth to high cell densities on inexpensive media. For instance yeasts grow on a wide range of carbon sources and are not restricted to glucose. Thus, the microbial organism to be used with the present invention may be selected from the group of yeasts described below:

*Arxula adeninivorans* (*Blastobotrys adeninivorans*) is a dimorphic yeast (it grows as a budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Candida boidinii* is a methylotrophic yeast (it can grow on methanol). Like other methylotrophic species such as *Hansenula polymorpha* and *Pichia pastoris*, it provides an excellent platform for the production of heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. Details on how to download the software implemented in Python and experimental testing of predictions are outlined in the following paper.

*Hansenula polymorpha* (*Pichia angusta*) is another methylotrophic yeast (see *Candida boidinii*). It can furthermore grow on a wide range of other substrates; it is thermotolerant and can assimilate nitrate (see also *Kluyveromyces lactis*). It has been applied to the production of hepatitis B vaccines, insulin and interferon alpha-2a for the treatment of hepatitis C, furthermore to a range of technical enzymes.

*Kluyveromyces lactis* is a yeast regularly applied to the production of kefir. It can grow on several sugars, most importantly on lactose which is present in milk and whey. It has successfully been applied among others to the production of chymosin (an enzyme that is usually present in the stomach of calves) for the production of cheese. Production takes place in fermenters on a 40,000 L scale.

*Pichia pastoris* is a methylotrophic yeast (see *Candida boidinii* and *Hansenula polymorpha*). It provides an efficient platform for the production of foreign proteins. Platform elements are available as a kit and it is worldwide used in academia for the production of proteins. Strains have been engineered that can produce complex human N-glycan (yeast glycans are similar but not identical to those found in humans).

*Saccharomyces cerevisiae* is the traditional baker's yeast known for its use in brewing and baking and for the production of alcohol. As protein factory it has successfully been applied to the production of technical enzymes and of pharmaceuticals like insulin and hepatitis B vaccines.

*Yarrowia lipolytica* is a dimorphic yeast (see *Arxula adeninivorans*) that can grow on a wide range of substrates. It has a high potential for industrial applications but there are no recombinant products commercially available yet.

In another embodiment the host cell is a microalgae such as *Chlorella* and *Prototheca*.

In another embodiment of the invention the host cell is a filamentous fungus, for example *Aspergillus*.

In further yet another embodiment the host cell is a plant cell. The host cell may be a cell of a higher plant, but the host cell may also be cells from organisms not belonging to higher plants for example cells from the moss *Physcomitrella patens*.

In another embodiment the host cell is a mammalian cell, such as a human, feline, porcine, simian, canine, murine, rat, mouse or rabbit cell.

The host cell may also be selected from the group consisting of CHO, CHO-K1, HE1193T, HEK293, COS, PC12, HiB5, RN33b, BHK cells.

As mentioned, the host cell can also be a prokaryotic cell such as a bacterial cell. If the cell is a prokaryotic cell the cell may be selected from, but not limited to *E. coli, Corynebacterium, Bacillus, Pseudomonas* and *Streptomyces* cells.

Plant

In some embodiments, the nucleic acids encoding the vanillin synthase of the invention are introduced into plants or plant cells to achieve production of vanillin or vanillin glucoside or vanillyl alcohol or vanillyl alcohol glucoside in said plant or plant cells. In particular, the nucleic acids may be introduced into plants other than *Vanilla planifolia* to obtain production of vanillin in these plants.

The plant may in addition to the heterologous nucleic acid encoding vanillin synthase also comprise additional heterologous nucleic acids, for example heterologous nucleic acids encoding one or more enzymes involved in synthesis of ferulic acid or a glucosyl transferase.

A plant or plant cell can be transformed by having a heterologous nucleic acid integrated into its genome, i.e., it can be stably transformed. Stably transformed cells typically retain the introduced nucleic acid with each cell division. A plant or plant cell can also be transiently transformed such that the recombinant gene is not integrated into its genome. Transiently transformed cells typically lose all or some portion of the introduced nucleic acid with each cell division such that the introduced nucleic acid cannot be detected in daughter cells after a certain number of cell divisions. Both transiently transformed and stably transformed transgenic plants and plant cells can be useful in the methods described herein.

Plant cells comprising a nucleic acid encoding a vanillin synthase used in methods described herein can constitute part or all of a whole plant. Such plants can be grown in a manner suitable for the species under consideration, either in a growth chamber, a greenhouse, or in a field. Plants may also be progeny of an initial plant comprising a nucleic acid encoding a vanillin synthase provided the progeny inherits the heterologous nucleic acid. Seeds produced by a transgenic plant can be grown and then selfed (or outcrossed and selfed) to obtain seeds homozygous for the nucleic acid construct.

The plants to be used with the invention can be grown in suspension culture, or tissue or organ culture. For the purposes of this invention, solid and/or liquid tissue culture techniques can be used. When using solid medium, plant cells can be placed directly onto the medium or can be placed onto a filter that is then placed in contact with the medium. When using liquid medium, transgenic plant cells can be placed onto a flotation device, e.g., a porous membrane that contacts the liquid medium.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, U.S. Pat. Nos. 5,538,880; 5,204,253; 6,329,571; and 6,013,863. If a cell or cultured tissue is used as the recipient tissue for transformation, plants can be regenerated from transformed cultures if desired, by techniques known to those skilled in the art. Heterologous nucleic acids encoding vanillin synthase may be introduced into cereal plants, such as barley as described by Hebelstrup et al., (2010) UCE: A uracil excision (USER (TM))-based toolbox for transformation of cereals. Plant Methods, 6:15 or by Holme et al. (2012) Cisgenic barley with improved phytase activity. Plant Biotechnol J 10, 237-247.

A population of plants can be screened and/or selected for those members of the population that carry the heterologous nucleic acid encoding vanillin synthase. For example, a population of progeny of a single transformation event can be screened for those plants having a desired level of expression of the vanillin synthase. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or nucleic acids. Methods for performing all of the referenced techniques are known. As an alternative, a population of plants comprising independent transformation events can be screened for those plants carrying all and/or expressing all the different heterologous nucleic acids. Selection and/or screening can be carried out over one or more generations, and/or in more than one geographic location. In some cases, the plants can be grown and selected under conditions which induce a desired phenotype or are otherwise necessary to produce a desired phenotype in the plant. In addition, selection and/or screening can be applied during a particular developmental stage in which the heterologous nucleic acid is expected to be expressed by the plant. Selection and/or screening can be carried out to choose those transgenic plants having a statistically significant difference in vanillin or vanillin beta-D-glucoside level relative to a control plant that lacks the heterologous nucleic acid encoding vanillin synthase.

Plants which include a plant cell according to the invention are also provided as are seeds produced by said plants.

The plant comprising a heterologous nucleic acid encoding vanillin synthase to be used with the present invention may for example be selected from: corn (*Zea. mays*), canola (*Brassica napus, Brassica rapa* ssp.), alfalfa (*Medicago sativa*), rice (*Oryza sativa*), rye (*Secale cerale*), sorghum (*Sorghum bicolor, Sorghum vulgare*), sunflower (*Helianthus annuas*), wheat (*Tritium aestivum* and other species), Triticale, Rye (*Secale*) soybean (*Glycine max*), tobacco (*Nicotiana tabacum*), potato (*Solanum tuberosum*), peanuts (*Arachis hypogaea*), cotton (*Gossypium hirsutum*), sweet potato (*Impomoea batatus*), cassava (*Manihot esculenta*), coffee (*Cofea* spp.), coconut (*Cocos nucifera*), pineapple (*Anana comosus*), citrus (*Citrus* spp.) cocoa (*Theobroma cacao*), tea (*Camellia senensis*), banana (*Musa* spp.), avacado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Primus amygdalus*), apple (*Malus* spp), Pear (*Pyrus* spp), plum and cherry tree (*Prunus* spp), Ribes (currant etc.), Vitis, Jerusalem artichoke (*Helianthemum* spp), non-cereal grasses (Grass family), sugar and fodder beets (*Beta vulgaris*), chicory, oats, barley, vegetables, and ornamentals.

In one embodiment of the invention the plant is a plant comprising edible parts. In particular, the plant may be a plant with a taste, where a combination with vanilla taste can be envisioned to be desirable. Thus, the plant may be a plant comprising an edible fruit, wherein it is desired that said fruit in addition to the natural taste of said fruit also contains a vanilla flavour. One non-limiting example of such a plant is tomato.

For example, plants of the present invention are crop plants (for example, cereals and pulses, maize, wheat, potatoes, tapioca, rice, sorghum, millet, cassava, barley, pea, sugar beets, sugar cane, soybean, oilseed rape, sunflower and other root, tuber or seed crops. Other important plants maybe fruit trees, crop trees, forest trees or plants grown for their use as spices or pharmaceutical products (*Mentha* spp, clove, *Artemesia* spp, *Thymus* spp, *Lavendula* spp, *Allium* spp., *Hypericum, Catharanthus* spp, *Vinca* spp, *Papaver* spp., *Digitalis* spp, *Rawolfia* spp., *Vanilla* spp., *Petrusilium* spp., *Eucalyptus*, tea tree, *Picea* spp, *Pinus* spp, *Abies* spp, *Juniperus* spp., Horticultural plants which may be used with the present invention may include lettuce, endive, and vegetable brassicas including cabbage, broccoli, and cauliflower, carrots, and carnations and geraniums.

The plant may also be selected from the group consisting of tobacco, cucurbits, carrot, strawberry, sunflower, tomato, pepper and Chrysanthemum.

The plant may also be a grain plants for example oil-seed plants or leguminous plants. Seeds of interest include grain seeds, such as corn, wheat, barley, sorghum, rye, etc. Oil-seed plants include cotton soybean, safflower, sunflower, Brassica, maize, alfalfa, palm, coconut, etc. Leguminous plants include beans and peas. Beans include guar, locust bean, fenugreek, soybean, garden beans, cowpea, mung bean, lima bean, fava been, lentils, chickpea.

In a further embodiment of the invention said plant is selected from the following group: maize, rice, wheat, sugar beet, sugar cane, tobacco, oil seed rape, potato and soybean. Thus, the plant may for example be rice.

The whole genome of *Arabidopsis thaliana* plant has been sequenced (Paquette, S. et al, Phytochemistry 62 (2003) 399-413). Consequently, very detailed knowledge is available for this plant and it may therefore be a useful plant to work with.

Accordingly, one plant, which may be used with the present invention is an *Arabidopsis* and in particular an *Arabidopsis thaliana*.

Interestingly, the present invention demonstrates that even plants quite distinct from *Vanilla planifolia* can be engineered to produce vanillin, vanillyl alcohol and/or vanillin glucoside. Thus, whereas *Vanilla planifolia* is a monocot, and more specifically an epiphytic climbing orchid, then the invention surprisingly demonstrates that even dicots are capable of producing vanillin, vanillyl alcohol and/or vanillin glucoside. Thus, in one embodiment of the invention, the host organism is a dicot. In a preferred embodiment of the invention, the plant is a plant of the order Solanales. In particular, the plant may be a plant of the genus *Nicotiana*, for example the plant may be *Nicotiana tobaccum*.

In one embodiment the invention relates to a plant comprising a heterologous nucleic acids encoding the vanillin synthase of the invention, wherein the plant is a plant used as animal feed. It may be advantageous for plants used as animal feed to comprise vanillin, because vanillin may induce appetite in animals and also may improve palability of feed prepared from the plants, thereby inducing increased feed uptake by animals. Furthermore, interestingly, plants comprising a heterologous nucleic acid encoding the vanillin synthase of the invention may also have reduced lignin content or lignin with a different composition offering favourable traits e.g. physical strength or biodegradability. Without being bound by theory it is speculated that expression of vanillin synthase according to the invention reduces the pool of ferulic acid available for biosynthesis of lignin, because at least part of the ferulic acid is converted to vanillin.

The plant used as animal feed may be any plant useful as animal feed. In general said plant may be a herbaceous plant, such as grass or legumes. Said grass may be any graminoids, such as "true grasses" of the Poaceae or Gramineae family, as well as the sedges of the Cyperaceae family or rushes of the Juncaceae family. Examples of useful true grasses include cereals, bamboo and the grasses of lawns (turf) and grassland, for example Switch grass.

In one preferred embodiment of the invention, the plant is a plant of a plant species with a high endogenous content of ferulic acid and/or a ferulic acid derivative. In particular, the plant may be of a plant species with a high endogenous content of ferulic acid and/or ferulic acid glucoside. In one embodiment of the invention, the plant is of a plant species accumulating high levels of free and/or accessible ferulic acid or ferulic acid glucoside. The primary cell wall of the commelinoid order of monocots and the Chenopodiaceae (e.g. sugar beet and spinach) contains substantial amounts of free phenylpropanoids in their non-lignified cell walls. A major fraction of these phenylpropanoids is ferulic acid. Thus, in one embodiment the plant may be a plant of the commelimoid order of monocots or a chenopodiaceae. In one embodiment the plant is a plant comprising at least 50 µg, for example at least 100 µg, such as at least 200 µg ferulic acid and/or ferulic acid derivative per g dry matter It may be preferred that the plant is not *Vanilla planifolia*. It may also be preferred that the plant is not Creeping Bentgrass.

Glucosyl Transferase

The microbial organism comprising a heterologous nucleic acid encoding a vanillin synthase may also be capable of glucosylating vanillin. Most microbial organisms, such as bacteria and fungi are not natively capable of glucosylating vanillin. Thus, the microbial organism may comprise at least one heterologous nucleic acid encoding a glucosyl transferase, preferably a glucosyl transferase able to efficiently catalyse glucosylation of vanillin.

Similar the plant comprising a heterologous nucleic acid encoding a vanillin synthase may also be capable of glucosylating vanillin. Said plant may comprise an endogenous glucosyl transferase activity capable of glucosylating vanillin. However, preferably the plant may comprise at least a heterologous nucleic acid encoding a glucosyl transferase, preferably a glucosyl transferase able to efficiently catalyse glucosylation of vanillin.

Glucosylation of vanillin is particularly useful. Vanillin-β-D-glucoside is the storage form of vanillin found in the vanilla pod. It is non-toxic to most organisms, including yeast, and has a higher solubility in water, as compared to vanillin. In contrast vanillin may be toxic to many hosts. In addition, the formation of vanillin-β-D-glucoside most likely pulls the biosynthesis further in the direction of vanillin production. In addition, glucosylation of vanillin may facilitate isolation.

The glucosyl transferase may be any glucosyl transferase capable of catalysing glucosylation of vanillin, i.e. capable of catalysing conjugation a glucose residue to vanillin. In particular, the glucosyl transferease may be a UDP-Glucose:Aglycon-Glucosyltransferase. Preferably the glucosyl transferase can catalyze the glucosylation of vanillin to produce vanillin beta-D-glucoside. Thus, the glucosyl transferase may be a Family 1 glucosyl transferease. Preferred glucosyl transferases according to the invention are enzymes classified under EC 2.4.1. Suitable glucosyl transferases include the UGT71C2, UGT72B1, UGT72E2, UGT84Δ2, UGT89B1, UGT85B1, and arbutin synthase polypeptides. Thus, the glucosyl transferase to be used with the present invention may for example be any of the glucosyl transferases having GenBank Accession Nos. AC0005496, NM_116337 or NM_126067. Thus, the recombinant host may comprise a heterologous nucleic acid encoding the UGT71C2, UGT72B1, UGT72E2, UGT84Δ2, UGT89B1, UGT85B1, or arbutin synthase or a functional homologue of any of the aforementioned sharing at least 80%, such as at least 85%, for example at least 90%, such as at least 95%, for example at least 98% sequence identity therewith. Other useful UGTs are described in WO 01/40491, for example on page 2-5 of WO 01/40491.

The *Arabidopsis thaliana* UGT72E2 is particularly useful. UGT72E2 exhibits high substrate specificity towards vanillin. In concordance with this observation, its expression in the vanillin producing yeast results in almost all vanillin being converted into vanillin-β-D-glucoside. The ability to turn vanillin into vanillin-β-D-glucoside in vivo is important, because microbial production of non-glucosylated vanillin beyond the 0.5-1 g/liter scale would be hampered by the toxicity of free vanillin. Glucosylation serves to circumvent the inhibitory effect.

Thus, the glucosyl transferase may be UGT72E2 of SEQ ID NO:3 or a functional homologue thereof sharing at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity". A functional homologue of UGT72E2 is also capable of catalysing glucosylation of vanillin to form vanillin-beta-D-glucoside. Glycosyltransferases catalysing the transfer of other sugars than glucose e.g. galactose, arabinose, rhamnose and xylose are also known and may also be introduced to obtain new sugar derivatives of vanillin.

Enzymes Involved in Synthesis of Ferulic Acid

The present invention relates to methods of producing vanillin from ferulic acid with the aid of vanillin synthase. The methods may employ use of a microbial organism or a plant, which produces ferulic acid, or ferulic acid may be added exogenously to the microbial organism or the plant.

Some microorganisms and many plants naturally produce and accumulate ferulic acid. However, other microbial organisms for example most bacteria or fungi do not naturally produce ferulic acid. Thus, in embodiments of the invention relating to bacteria or fungi not naturally expressing the genes encoding all the required enzymes for endogenous production of ferulic acid, the methods may comprise contacting said bacteria or fungi with ferulic acid, for example by adding ferulic acid to the growth medium. In other embodiments of the invention relating to bacteria or fungi not naturally producing ferulic acid, the said bacteria or fungi may be engineered to express one or more enzymes involved in the synthesis of ferulic acid. It is also comprised within the invention that one microbial organism engineered to express one or more enzymes involved in the synthesis of ferulic acid may be used together with the microbial organism comprising a heterologous nucleic acid encoding vanillin synthase, for example, they may be co-cultured.

Thus, in one embodiment, the invention relates to microbial organisms and methods of using said microbial organism, wherein the microbial organism comprises at least one heterologous nucleic acid encoding an enzyme involved in synthesis of ferulic acid.

The enzyme involved in synthesis of ferulic acid may for example be selected from the group consisting of phenylalanine ammonia-lyase, trans-cinnamate 4-monooxygenase, tyrosine ammonia-lyase, 4-coumaryl-3-hydroxylase, caffeate O-methyltransferase, phenylalanine ammonia-lyase, trans-cinnamate 4-monooxygenase, coumarate-CoA ligase, shikimate O-hydroxycinnamoyltransferase, 4-coumaryl-3-hydroxylase, caffeoyl-CoA O-methyltransferase, caffeate O-methyltransferase and flavone 3'-O-methyltransferase. Each of these enzymes are described in more detail herein below.

Different pathways to obtain ferulic acid are known. A number of pathways to obtain ferulic acid are described in FIG. 6 of Schoch et al., 2006, Environ Chem Lett, 4:127-136 (hereby incorporated by reference herein). Thus, the host organisms may comprise all the enzymes of one of the pathways to obtain ferulic acid shown in FIG. 6 of Schoch et al., 2006.

One pathway (herein designated ferulic acid pathway 1) for the biosynthesis of ferulic acid contains the following enzymes:

Step 1: Phenylalanine ammonia-lyase, which may be any of the phenylalanine ammonia lyases described herein below.

Step 2: trans-cinnamate 4-monooxygenase (cinnamate 4-hydroxylase), which may be any of the trans-cinnamate 4-monooxygenase described herein below.

Step 3: 4-coumaryl-3-hydroxylase, which may be any of the 4-coumaryl-3-hydroxylases described herein below.

Step 4: caffeate O-methyltransferase or flavone 3'-O-methyltransferase, which may be any of the caffeate O-methyltransferases or flavone 3'-O-methyltransferases described herein below.

The microbial organism of the invention, for example the yeast cell or the bacteria may comprise at least one heterologous nucleic acid encoding one enzyme of ferulic acid pathway 1, such as at least two heterologous nucleic acids each encoding a different enzyme of ferulic acid pathway 1, for example at least 3 nucleic acids each encoding a different enzyme of ferulic acid pathway 1. In particular the microbial organism, for example the yeast cell or the bacteria may contain 4 heterologous nucleic acids each encoding a different enzyme of ferulic acid pathway 1.

Another pathway (herein designated ferulic acid pathway 2) for the biosynthesis ferulic acid contains the following enzymes:

Step 1+2: tyrosine ammonia-lyase, which may be any of the tyrosine ammonia lyases described herein below.

Step 3: 4-coumaryl-3-hydroxylase, which may be any of the 4-coumaryl-3-hydroxylases described herein below.

Step 4: caffeate O-methyltransferase or flavone 3'-O-methyltransferase, which may be any of the caffeate O-methyltransferases or flavone 3'-O-methyltransferases described herein below.

The microbial organism of the invention, for example the yeast cell or the bacteria may comprise at least one heterologous nucleic acid encoding one enzyme of pathway 2, such as at least two heterologous nucleic acids each encoding a different enzyme of pathway 2. In particular the microbial organism, for example the yeast cell or the bacteria may contain 3 heterologous nucleic acids each encoding a different enzyme of ferulic acid pathway 2.

Yet another pathway (herein designated ferulic acid pathway 3) for the biosynthesis ferulic acid contains the following enzymes:

Step 1: phenylalanine ammonia-lyase, which may be any of the phenylalanine ammonia-lyases described herein below.

Step 2: trans-cinnamate 4-monooxygenase (cinnamate 4-hydroxylase), which may be any of the trans-cinnamate 4-monooxygenases described herein below.

Step 3: 4-coumarate-CoA ligase, which may be any of the 4-coumarate-CoA ligases described herein below.

Step 4: shikimate O-hydroxycinnamoyltransferase, which may be any of the shikimate O-hydroxycinnamoyltransferases described herein below.

Step 5: 4-coumaryl-3-hydroxylase, which may be any of the 4-coumaryl-3-hydroxylases described herein below.

Step 6: shikimate O-hydroxycinnamoyltransferase, which may be any of the shikimate O-hydroxycinnamoyltransferases described herein below.

Step 7: caffeoyl-CoA O-methyltransferase, which may be any of the caffeoyl-CoA O-methyltransferases described herein below.

The microbial organism of the invention, for example the yeast cell or the bacteria may comprise at least one heterologous nucleic acid encoding one enzyme of ferulic acid pathway 3, such as at least two heterologous nucleic acids each encoding a different enzyme of ferulic acid pathway 3, for example at least 3 nucleic acids each encoding a different enzyme of ferulic acid pathway 3, such as at least 4 heterologous nucleic acids each encoding a different enzyme of ferulic acid pathway 3, for example at least 5 nucleic acids each encoding a different enzyme of ferulic acid pathway 3, such as at least 6 heterologous nucleic acids each encoding a different enzyme of ferulic acid pathway 3. In particular the microbial organism, for example the yeast cell or the bacteria may contain 7 heterologous nucleic acids each encoding a different enzyme of ferulic acid pathway 3.

Even another pathway (herein designated ferulic acid pathway 4) for the biosynthesis ferulic acid contains the following enzymes:

Step 1+2: tyrosine ammonia-lyase, which may be any of the tyrosine ammonia-lyases described herein below.

Step 3: 4-coumarate-CoA ligase, which may be any of the 4-coumarate-CoA ligases described herein below.

Step 4: shikimate O-hydroxycinnamoyltransferase, which may be any of the shikimate O-hydroxycinnamoyltransferases described herein below.

Step 5: 4-coumaryl-3-hydroxylase, which may be any of the 4-coumaryl-3-hydroxylases described herein below.

Step 6: shikimate O-hydroxycinnamoyltransferase, which may be any of the shikimate O-hydroxycinnamoyltransferases described herein below.

Step 7: caffeoyl-CoA O-methyltransferase, which may be any of the caffeoyl-CoA O-methyltransferases described herein below.

Still another pathway (herein designated ferulic acid pathway 5) for the biosynthesis ferulic acid contains the following enzymes:

1) Vanillyl-Alcohol Oxidase (VAO), which May be any of the VAO Described Herein Below This pathway starts from eugenol. Thus, if the microbial organism does not synthesize eugenol, then it is preferred that the microbial organism is cultured in the presence of eugenol. In addition to VAO, the microbial organism preferably comprises an enzyme capable of catalysing conversion of coniferyl alcohol to form ferulic acid. Such an enzyme is endogenously present in may microbial organisms, for example in *S. cerevisiae*. Detail regarding ferulic acid pathway 5 is provided in Lambert et al., 2013, Flavor and Fragrance Journal, DOI 10.1002/ffj.3171).

The microbial organism of the invention, for example the yeast cell or the bacteria may comprise at least one heterologous nucleic acid encoding one enzyme of ferulic acid pathway 4, such as at least two heterologous nucleic acids each encoding a different enzyme of ferulic acid pathway 4, for example at least 3 nucleic acids each encoding a different enzyme of ferulic acid pathway 4, such as at least 4 heterologous nucleic acids each encoding a different enzyme of ferulic acid pathway 4, for example at least 5 nucleic acids each encoding a different enzyme of ferulic acid pathway 4. In particular the microbial organism, for example the yeast cell or the bacteria may contain 6 heterologous nucleic acids each encoding a different enzyme of ferulic acid pathway 4.

Phenylalanine Ammonia-Lyase

The phenylalanine ammonia-lyase to be used with the present invention may be any phenylalanine ammonia-lyase known to the skilled person. In particular the phenylalanine ammonia-lyase may be an enzyme classified under EC 4.3.1.24.

Thus the phenylalanine ammonia-lyase according to the present invention is preferably an enzyme capable of catalysing the following reaction:

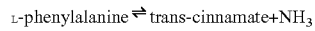

L-phenylalanine ⇌ trans-cinnamate+$NH_3$

The phenylalanine ammonia-lyase may be phenylalanine ammonia-lyase from a variety of sources, for example from plants. Examples of useful phenylalanine ammonia-lyases are described in Vannelli et al., 2006 and Shin et al 2012.

Thus, the phenylalanine ammonia-lyase may be phenylalanine ammonia-lyase of SEQ ID NO:4 or a functional homologue thereof sharing at least 70%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity".

A functional homologue of a phenylalanine ammonia-lyase is also capable of catalysing the following reaction:

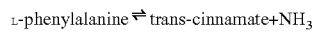

L-phenylalanine ⇌ trans-cinnamate+$NH_3$

Trans-Cinnamate 4-Monooxygenase

The trans-cinnamate 4-monooxygenase to be used with the present invention may be any trans-cinnamate 4-monooxygenase known to the skilled person. trans-Cinnamate 4-monooxygenase may also be designated cinnamate 4-hydroxylase. In particular, the trans-cinnamate 4-monooxygenase may be any enzyme classified under EC 1.14.13.11. Thus, trans-cinnamate 4-monooxygenase is preferably an enzyme capable of catalysing the following reaction:

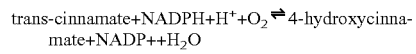

trans-cinnamate+NADPH+$H^+$+$O_2$ ⇌ 4-hydroxycinnamate+NADP++$H_2O$

The trans-cinnamate 4-monooxygenase may be trans-cinnamate 4-monooxygenase from a variety of sources, for example from plants. One example of a useful trans-cinnamate 4-monooxygenase is *Arabidopsis thaliana* CYP73A5 (GenBank accession number: U37235). Thus, trans-cinnamate 4-monooxygenase may be trans-cinnamate 4-monooxygenase of SEQ ID NO:5 or a functional homologue thereof sharing at least 70%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity".

A functional homologue of a trans-cinnamate 4-monooxygenase is also capable of catalysing the following reaction:

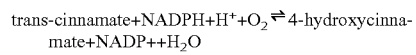

trans-cinnamate+NADPH+$H^+$+$O_2$ ⇌ 4-hydroxycinnamate+NADP++$H_2O$

Tyrosine Ammonia-Lyase

The tyrosine ammonia-lyase to be used with the present invention may be any tyrosine ammonia-lyase known to the skilled person. In particular, the tyrosine ammonia-lyase may be any enzyme classified under EC 4.3.1.23. Thus, tyrosine ammonia-lyase is preferably an enzyme capable of catalysing the following reaction:

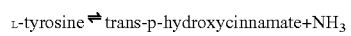

L-tyrosine ⇌ trans-p-hydroxycinnamate+$NH_3$

The tyrosine ammonia-lyase may be tyrosine ammonia-lyase from a variety of sources, for example from plants. Examples of useful tyrosine ammonia-lyase are described in Vannelli et al 2006 and Shin et al 2012. Also tyrosine ammonia-lyase from various slime molds may be used with the invention.

Thus, tyrosine ammonia-lyase may be tyrosine ammonia-lyase of SEQ ID NO:6 or a functional homologue thereof sharing at least 70%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity".

A functional homologue of a tyrosine ammonia-lyase is also capable of catalysing the following reaction:

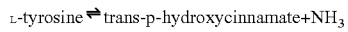

L-tyrosine ⇌ trans-p-hydroxycinnamate+NH$_3$ 4-coumaryl-3-hydroxylase

The 4-coumaryl-3-hydroxylase to be used with the present invention may be any 4-coumaryl-3-hydroxylase known to the skilled person. In particular, the 4-coumaryl-3-hydroxylase may be any enzyme classified under EC 1.14.-.-.

The 4-coumaryl-3-hydroxylase may be 4-coumaryl-3-hydroxylase from a variety of sources, for example from plants. Examples of useful 4-coumaryl-3-hydroxylase includes Red clover coumarate 3'-hydroxylase (CYP98A44), *Arabidopsis thaliana* p-coumarate 3-hydroxylase (CYP98A3)(SEQ ID NO:7), CYP98A8 p-coumarate 3-hydroxylase of *Arabidopsis thaliana* (SEQ ID NO:8) or CYP98A9 p-coumarate 3-hydroxylase of *Arabidopsis thaliana* (SEQ ID NO:9).

Thus, 4-coumaryl-3-hydroxylase may be 4-coumaryl-3-hydroxylase of SEQ ID NO:7, SEQ ID NO:8, SEQ ID NO:9 or a functional homologue of any of the aforementioned sharing at least 70%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity".

Caffeate O-Methyltransferase

The caffeate O-methyltransferase to be used with the present invention may be any caffeate O-methyltransferase known to the skilled person. In particular, the caffeate O-methyltransferase may be any enzyme classified under EC 2.1.1.68. Thus, caffeate O-methyltransferase is preferably an enzyme capable of catalysing the following reaction:

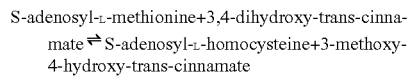

S-adenosyl-L-methionine+3,4-dihydroxy-trans-cinnamate ⇌ S-adenosyl-L-homocysteine+3-methoxy-4-hydroxy-trans-cinnamate Flavone 3'-O-methyltransferase The flavone 3'-O-methyltransferase to be used with the present invention may be any flavone 3'-O-methyltransferase known to the skilled person. In particular, the flavone 3'-O-methyltransferase may be any enzyme classified under EC 2.1.1.42. Thus, flavone 3'-O-methyltransferase is preferably an enzyme capable of catalysing the following reaction:

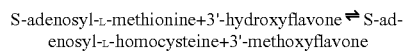

S-adenosyl-L-methionine+3'-hydroxyflavone ⇌ S-adenosyl-L-homocysteine+3'-methoxyflavone 4-coumarate-CoA ligase The 4-coumarate-CoA ligase to be used with the present invention may be any 4-coumarate-CoA ligase known to the skilled person. In particular, the 4-coumarate-CoA ligase may be any enzyme classified under EC 6.2.1.12. Thus, 4-coumarate-CoA ligase is preferably an enzyme capable of catalysing the following reaction:

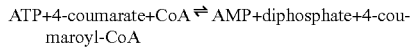

ATP+4-coumarate+CoA ⇌ AMP+diphosphate+4-coumaroyl-CoA

The 4-coumarate-CoA ligase may be 4-coumarate-CoA ligase from a variety of sources, for example from plants. Examples of useful 4-coumarate-CoA ligases include *Arabidopsis thaliana* 4-coumarate:CoA ligase 3 (SEQ ID NO:10) or 4-coumarate:coenzyme A ligase of *Nicotiana tabacum* (SEQ ID NO:11).

Thus, 4-coumarate-CoA ligase may be 4-coumarate-CoA ligase of SEQ ID NO:10, SEQ ID NO:11 or a functional homologue thereof sharing at least 70%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity".

A functional homologue of a 4-coumarate-CoA ligase is also capable of catalysing the following reaction:

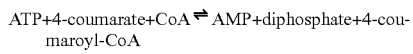

ATP+4-coumarate+CoA ⇌ AMP+diphosphate+4-coumaroyl-CoA

Shikimate O-Hydroxycinnamoyltransferase

The shikimate O-hydroxycinnamoyltransferase to be used with the present invention may be any shikimate O-hydroxycinnamoyltransferase known to the skilled person. In particular, the shikimate O-hydroxycinnamoyltransferase may be any enzyme classified under EC 2.3.1.133. Thus, shikimate O-hydroxycinnamoyltransferase is preferably an enzyme capable of catalysing the following reaction:

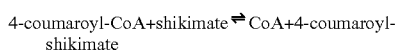

4-coumaroyl-CoA+shikimate ⇌ CoA+4-coumaroyl-shikimate

The shikimate O-hydroxycinnamoyltransferase may be shikimate O-hydroxycinnamoyltransferase from a variety of sources, for example from plants. Examples of useful shikimate O-hydroxycinnamoyltransferase are described include *Nicotiana tabacum* Shikimate O-hydroxycinnamoyltransferase (SEQ ID NO:12), *Coffea arabica* hydroxycinnamoyl transferase (SEQ ID NO:13) or *Populus trichocarpa* hydroxycinnamoyl CoA shikimate/quinate hydroxycinnamoyltransferase (SEQ ID NO:14).

Thus, shikimate O-hydroxycinnamoyltransferase may be shikimate O-hydroxycinnamoyltransferase of SEQ ID NO:12, SEQ ID NO:13, SEQ ID NO:14 or a functional homologue of any of the aforementioned sharing at least 70%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity".

A functional homologue of a shikimate O-hydroxycinnamoyltransferase is also capable of catalysing the following reaction:

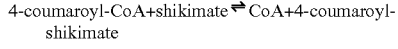

4-coumaroyl-CoA+shikimate ⇌ CoA+4-coumaroyl-shikimate

Caffeoyl-CoA O-Methyltransferase

The caffeoyl-CoA O-methyltransferase to be used with the present invention may be any caffeoyl-CoA O-methyltransferase known to the skilled person. In particular, the caffeoyl-CoA O-methyltransferase may be any enzyme classified under EC 2.1.1.104. Thus, caffeoyl-CoA O-methyltransferase is preferably an enzyme capable of catalysing the following reaction:

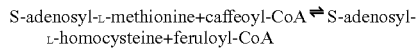
S-adenosyl-L-methionine+caffeoyl-CoA ⇌ S-adenosyl-L-homocysteine+feruloyl-CoA The caffeoyl-CoA O-methyltransferase may be caffeoyl-CoA O-methyltransferase from a variety of sources, for example from plants. Examples of useful caffeoyl-CoA O-methyltransferase includes *Arabidopsis thaliana* caffeoyl-CoA O-methyltransferase (SEQ ID NO:15) or caffeoyl-CoA O-methyltransferase of *Nicotiana tabacum* (SEQ ID NO: 16).

Thus, caffeoyl-CoA O-methyltransferase may be caffeoyl-CoA O-methyltransferase of SEQ ID NO:6 or a functional homologue thereof sharing at least 70%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity".

A functional homologue of a caffeoyl-CoA O-methyltransferase is also capable of catalysing the following reaction:

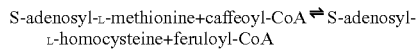
S-adenosyl-L-methionine+caffeoyl-CoA ⇌ S-adenosyl-L-homocysteine+feruloyl-CoA Vanillyl-Alcohol Oxidase The vanillyl-alcohol oxidase (VAO) to be used with the present invention may be any VAO known to the skilled person. In particular, the VAO may be any enzyme classified under EC 1.1.3.38. The VAO may be VAO from a variety of sources, for example from fungi. Examples of useful VAO includes *Penicillium simplicissimum* VAO.

Thus, VAO may be the VAO of the sequence with reference number CAA75722 of the NCBI database (as available on 5 Nov. 2013) or a functional homologue thereof sharing at least 70%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity".

Sequence Identity

A high level of sequence identity indicates likelihood that the first sequence is derived from the second sequence. Amino acid sequence identity requires identical amino acid sequences between two aligned sequences. Thus, a candidate sequence sharing 80% amino acid identity with a reference sequence, requires that, following alignment, 80% of the amino acids in the candidate sequence are identical to the corresponding amino acids in the reference sequence. Identity according to the present invention is determined by aid of computer analysis, such as, without limitations, the ClustalW computer alignment program (Higgins D., Thompson J., Gibson T., Thompson J. D., Higgins D. G., Gibson T. J., 1994. CLUSTAL W: improving the sensitivity of progressive multiple sequence alignment through sequence weighting, position-specific gap penalties and weight matrix choice. Nucleic Acids Res. 22:4673-4680), and the default parameters suggested therein. The ClustalW software is available from as a ClustalW WWW Service at the European Bioinformatics Institute. Using this program with its default settings, the mature (bioactive) part of a query and a reference polypeptide are aligned. The number of fully conserved residues are counted and divided by the length of the reference polypeptide.

The ClustalW algorithm may similarly be used to align nucleotide sequences. Sequence identities may be calculated in a similar way as indicated for amino acid sequences. In one important embodiment, the cell of the present invention comprises a nucleic acid sequence coding, as define herein.

Promoter Sequence

The present invention relates to microbial organisms and plants comprising a heterologous nucleic acid encoding vanillin synthase and optionally also one or more additional heterologous nucleic acid sequences encoding enzyme(s) involved in synthesis of ferulic acid and/or a glucosyl transferase. In order to ensure proper expression of said heterologous nucleic acids, said coding heterologous nucleic acids are in general operably linked to a promoter sequence directing expression in the microbial cell or the plant.

A promoter is a region of DNA that facilitates the transcription of a particular gene. Promoters are located near the genes they regulate, on the same strand and typically upstream (towards the 5' region of the sense strand). In order for the transcription to take place, the enzyme that synthesizes RNA, known as RNA polymerase, must attach to the DNA near a gene. Promoters contain specific DNA sequences and response elements which provide a secure initial binding site for RNA polymerase and for proteins called transcription factors that recruit RNA polymerase. These transcription factors have specific activator or repressor sequences of corresponding nucleotides that attach to specific promoters and regulate gene expressions.

The promoter sequence may in general be positioned immediately adjacent to the coding heterologous nucleic acid.

The promoter sequence according to the present invention in general comprises at least a core promoter, which is the minimal portion of the promoter required to properly initiate transcription. In addition the promoter sequence may comprise one or more of the following promoter elements:
Transcription Start Site (TSS)
A binding site for RNA polymerase
General transcription factor binding sites
Proximal promoter sequence upstream of the gene that tends to contain primary regulatory elements
Specific transcription factor binding sites
distal promoter sequence upstream of the gene that may contain additional regulatory elements, often with a weaker influence than the proximal promoter
Binding sites for repressor proteins
Reduced Expression of Phenyl Acrylate Decarboxylase In embodiments of the invention where the microbial organism or the plant expresses a high level of enzymes using ferulic acid as substrate, it may be advantageous to reduce the expression of such enzymes.

Certain microbial organisms, such as yeast expresses ferulic acid decarboxylase, which is capable of catalysing decarboxylation of ferulic acid to obtain 4-vinyl guaiacol. Accordingly, it is preferred that if the microbial organism expresses ferulic acid decarboxylase then the expression of said ferulic acid decarboxylase is reduced.

Reduced expression may be achieved using various conventional techniques known to the skilled person. For example, nucleic acids, e.g. antisense nucleic acids that inhibit expression of ferulic acid decarboxylase may be included in a recombinant construct that is transformed into the microbial organism. Alternatively, PCR based mutagenesis techniques can be used to generate mutants in the gene for ferulic acid decarboxylase or the entire ferulic acid carboxylase gene may be deleted using PCR based gene deletion strategy, for example adapted from the strategy described by Baudin et al., 1993. Briefly, PCR-generated DNA molecules consisting of a marker cassette with short flanking homology regions to the genomic ferulic acid decarboxylase gene are introduced into the microbial organism and integrated into the genome by homologous recombination. The genomic sequence of the ferulic acid decarboxylase gene from various organisms is available. For example the genomic sequence of the ferulic acid decarboxylase gene is available under the GenBank accession number BK006938.2.

Ferulic Acid

As used herein the term ferulic acid refers to a compound of the structure:

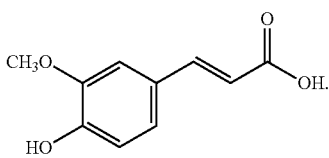

In certain embodiments of the invention, the methods for producing vanillin and/or vanillin glucoside involves contacting the producing microbial organism or plant with ferulic acid and/or a ferulic acid derivative. It is preferred that said microbial organism or plant is contacted with ferulic acid. In particular, this is relevant in embodiments of the invention where the microbial organism or the plant is not capable of producing ferulic acid. Most bacteria and fungi are not capable of producing ferulic acid. Thus it may be in particular relevant to contact the microbial organism with ferulic acid and/or a ferulic acid derivative in embodiments of the invention where the microbial organism is bacteria or fungi, for example yeast.

Preferably, said microbial organism is cultivated in the presence of ferulic acid, for example the culture medium may comprise ferulic acid. Thus, the culture medium may preferably comprise at least 1 mM, preferably at least 3 mM, for example at least 5 mM ferulic acid.

Alternative, said microbial organism is cultivated in the presence of ferulic acid derivative or a mixture of ferulic acid and ferulic acid derivative, for example the culture medium may comprise ferulic acid derivative and/or ferulic acid. Thus, the culture medium may preferably comprise at least 1 mM, preferably at least 3 mM, for example at least 5 mM ferulic acid and/or ferulic acid derivative.

In one embodiment, the invention relates to preparing vanillin in vitro by contacting ferulic acid and/or a ferulic acid derivative with vanillin synthase, which may be any of the vanillin synthases described herein above in the section "Vanillin synthase". Said vanillin synthase may be provided in a purified form or in an extract, for example an extract prepared from a microbial organism expressing vanillin synthase, such as any of the microbial organisms described herein above in the section "Microbial organism". Any useful concentration of ferulic acid and/or ferulic acid derivative may be used, for example the concentration of ferulic acid and/or ferulic acid derivative may be 1 mM, preferably at least 3 mM, for example at least 5 mM ferulic acid/ferulic acid derivative.

The ferulic acid may be provided in any useful form. For example molasses in general contains large amounts of ferulic acid and thus the culture medium may comprise or even consist of molasses. The molasses may for example be molasses of sugar beet or sugar cane.

The ferulic acid may also be provided by providing plants or plant part comprising ferulic acid or extract thereof.

For example ferulic acid may be provided in the form of asafetida, the dried latex from the giant fennel or as an extract thereof. The ferulic acid may also be provided as seeds of coffee, apple, artichoke, peanut, or orange or as extracts thereof. Ferulic acid may also be provided as a commelinid plant or part thereof. Said commelinid plant may for example be rice, wheat, oat, Chinese water chestnut or pineapple. The ferulic acid may also be provided in the form of Açai oil.

Ferulic acid may also be purified ferulic acid, which for example may be purified from any of the aforementioned sources, or ferulic acid may be prepared by organic chemistry procedures.

The ferulic acid may also be provided from a microbial organism capable of producing ferulic acid. Such as microbial organism may preferably contain one or more heterologous nucleic acids encoding enzymes involved in synthesis of ferulic acid, for example said microbial organism may comprise nucleic acids encoding the enzymes as described herein above in the section "Enzymes involved in synthesis of ferulic acid". The microbial organism capable of producing ferulic acid may be co-cultured together with the microbial organism comprising a heterologous nucleic acid encoding vanillin synthase. Alternatively, crude culture medium or partly purified or purified culture medium from cultivation of the microbial organism capable of producing ferulic acid may be added to the culture medium for growing the microbial organism comprising a heterologous nucleic acid encoding vanillin synthase.

The ferulic acid derivative may be any derivative of ferulic acid, which may serve as a substrate for vanillin synthase. Preferably, the ferulic acid derivative is a compound of the general formula

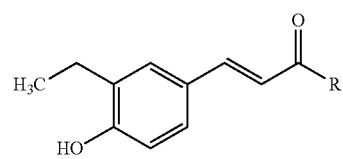

wherein R for example may be an alkyl, such as an $C_{1-6}$-alkyl, an alkoxy, such as $C_{1-6}$ alkoxy, a glycose ester, a glycoside, S-CoA, shikimate or quinate.

Said glycoside ester may be comprise any sugar, such as glucose. The glycoside is preferably glucoside.

Thus the ferulic acid derivative may for example be selected from the group consisting of Ferulic acid glucose ester, ferulic acid glucoside, Feruloyl-CoA, Ferulic acid shikimate and feruloyl-quinate.

Sequence listing

| | |
|---|---|
| SEQ ID NO: 1 | Protein sequence of vanillin synthase of *Vanilla planifolia* (VpVAN) |
| SEQ ID NO: 2 | Coding sequence of Vp VAN WT gene |
| SEQ ID NO: 3 | Protein sequence of UGT72E2 of *A. thaliana* |
| SEQ ID NO: 4 | phenylalanine ammonia-lyase |
| SEQ ID NO: 5 | *Arabidopsis thaliana* CYP73A5 (GenBank accession number: U37235) |
| SEQ ID NO: 6 | Tyrosine ammonia-lyase |
| SEQ ID NO: 7 | *Arabidopsis thaliana* p-coumarate 3-hydroxylase (CYP98A3) (GenBank accession number: AEC09893.1) |
| SEQ ID NO: 8 | CYP98A8 p-coumarate 3-hydroxylase of *Arabidopsis thaliana* (GenBank accession number: AEE35607.1) |
| SEQ ID NO: 9 | CYP98A9 p-coumarate 3-hydroxylase of *Arabidopsis thaliana* (Genbank accession number AEE35608.1.) |
| SEQ ID NO: 10 | *Arabidopsis thaliana* 4-coumarate:CoA ligase 3 (GenBank accession number AF106088_1) |
| SEQ ID NO: 11 | 4-coumarate:coenzyme A ligase of *Nicotiana tabacum* (GenBank accession number AAB18637) |
| SEQ ID NO: 12 | *Nicotiana tabacum* Shikimate O-hydroxycinnamoyltransferase (GenBank accession number Q8GSM7) |
| SEQ ID NO: 13 | *Coffea arabica* hydroxycinnamoyl transferase (GenBank accession number CAJ40778.1) |
| SEQ ID NO: 14 | *Populus trichocarpa* hydroxycinnamoyl CoA shikimate/quinate hydroxycinnamoyltransferase (GenBank accession number XP_002332068.1) |
| SEQ ID NO: 15 | *Arabidopsis thaliana* caffeoyl-CoA O-methyl-transferase (GenBank accession number Q9C5D7) |
| SEQ ID NO: 16 | caffeoyl-CoA O-methyltransferase of *Nicotiana tabacum* (GenBank accession number CAA91228) |
| SEQ ID NO: 17 | Protein sequence of VpVAN lacking signal peptide. |
| SEQ ID NO: 18 | Coding sequence for Vp VAN WT gene codon optimized for expression in yeast |
| SEQ ID NO: 19 | Forward primer |
| SEQ ID NO: 20 | Reverse primer |
| SEQ ID NO: 21 | Protein sequence of vanillin synthase of *Glechoma hederacea* (GhVAN) |
| SEQ ID NO: 22 | Cysteine protease of *Nicotiana benthamiana* |
| SEQ ID NO: 23 | DNA sequence encoding GhVAN |
| SEQ ID NO: 24 | DNA sequence encoding chimeric vanillin synthase |

EXAMPLES

Example 1

Vanillin Synthase (VpVAN)

Based on sequence information available from US2003/0070188, the coding sequence of 4-HBS was obtained (SEQ ID NO:2).

Figure 1:
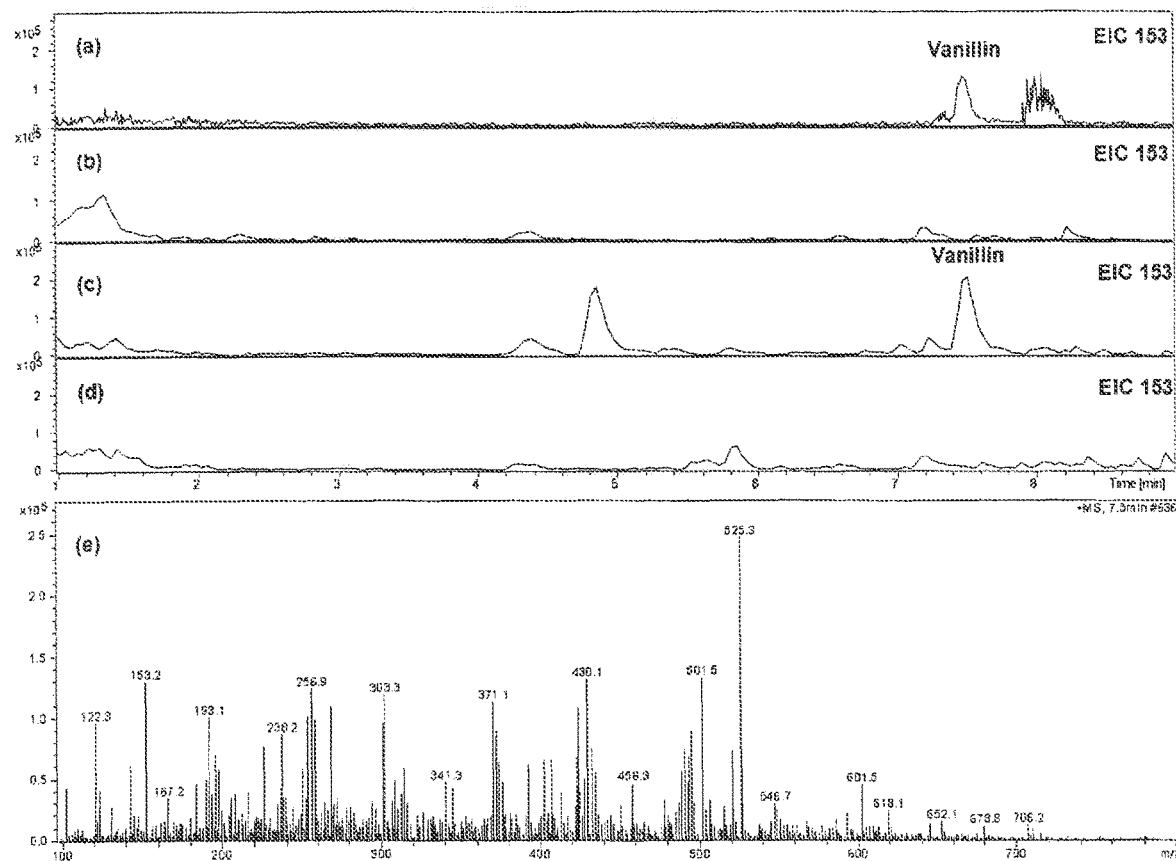
FIG. 1 shows a LC-MS chromatogram from in vitro feedings of VpVAN. The figure shows that the enzyme is able to catalyze carbon two cleavage of ferulic acid to vanillin. This reaction does not require CoASH, ATP and NAD+ as co-factors. Ion chromatograms of a protein solution with VpVAN fed with 5 mM of ferulic acid for 1 h in 2.5 mM DTT in 30° C. Furthermore, VAN is able to catalyze carbon two cleavage of ferulate CoA to vanillin in the presence of ATP, NAD$^+$. Extracted ion chromatogram of a protein solution with VAN fed with 5 mM of ferulate CoA for 1 h in 2.5 mM DTT, 0.1 mM ATP and 0.1 mM NAD+ in 30° C. (EIC 153: Extracted ion chromatogram m/z (vanillin mw+H$^+$)
(a) VpVAN fed with ferulic acid Negative control fed with ferulic acid
(b) VpVAN fed with ferulate CoA Negative control fed with ferulate CoA
(c) Vanillin fragmentation pattern at 7.5 min.

The TNT Quick Coupled Transcription/Translation PROMEGA kit for PCR-generated DNA was used to produce protein from an isolated 4-HBS PCR-generated gene (the expressed protein was labelled with S35 to check for successful in vitro translation. To investigate the substrate specificity of this enzyme 2.5 mM of p-coumaric acid, ferulic acid and caffeic acid were tested as putative substrates in a feeding experiment. After administrating protein solutions with putative substrates for 1 h and 24 h respectively, the resulting metabolic profile in the presence and absence of 4-HBS was analyzed by LC-MS. It could clearly be seen that 4-HBS catalyzed chain shortening of ferulic acid to vanillin but was not able to catalyze chain shortening of neither p-coumaric acid nor caffeic acid. FIG. 1(a) shows extracted ion chromatogram of the protein solution fed with 5 mM of ferulic acid for 1 h in 400 mM Tris/HCl, pH8, 20 mM $MgCl_2$, 2.5 mM of dithiothreitol (DTT) at 30 degree celcius. Vanillin peak is observed at 7.5 min which is not present in negative control where protein solution without 4-HBS was treated under the same conditions (see FIG. 1(b). FIG. 1(c) shows extracted ion chromatogram of the protein solution fed 5 mM of ferulate CoA for 1 h in 2.5 mM DTT, 0.1 mM ATP and 0.1 mM $NAD^+$ at 30° C. Also here a vanillin peak is observed, which is absent in the negative control (see FIG. 1(d). FIG. 1(e) shows the Vanillin fragmentation pattern at 7.5 min.

Accordingly we renamed 4-HBS to Vanillin Synthase, or VpVAN.

Example 2

Expression of VpVAN in Yeast to Make Vanillin Glucoside from Ferulic Acid

Figure 3:
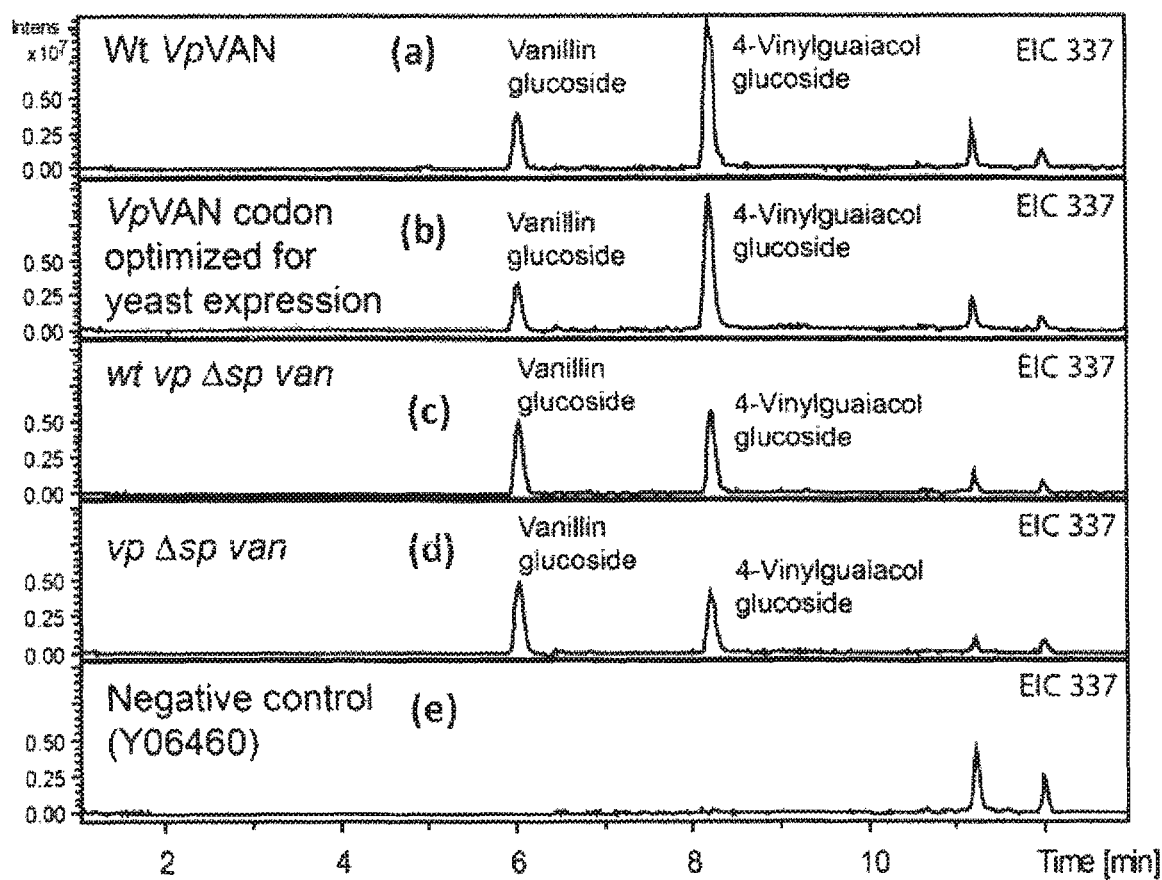
FIG. 3 shows the result of biosynthetic studies carried out with yeast harboring stably integrated Wt VpVAN, VpVAN codon optimized for yeast expression, truncated VpVAN devoid of the signal peptide (wt vp Δsp van) and with truncated VpVAN devoid of the signal peptide and codon optimized for yeast expression. (vp Δsp van). The yeast strains were incubated with different putative substrates for 72 h in synthetic media before metabolite profiles were determined by LC-MS. Formation of vanillin glucoside was observed with yeast fed with ferulic acid. (EIC 337—Extracted ion chromatogram m/z Vanillin glucoside mw+22).
(a) Wt VpVAN
(b) VpVAN codon optimized for yeast expression
(c) wt vp Δsp van—WtVpVAN devoid of the signal peptide
(d) vp Δsp van—VpVAN devoid of the signal peptide and codon optimized for yeast expression
(e) Negative control (Yeast strain Y06460)

This example describes biosynthesis in yeast of vanillin glucoside from ferulic acid by the heterologous expression of *V. planifolia* VpVAN. The substrate specificity of vanillin synthase was further confirmed by transient and stable expression in *S. cerevisiae* strain Fsb99. Yeast was transformed with a nucleic acid encoding VpVAN of SEQ ID NO:1 inserted into the Gal-induced yeast expression vector p416 TEF (said cells also referred to as VpVAN-transformed yeast herein). VpVAN-transformed yeast was grown in synthetic media containing galactose and 5 mM of putative substrates. Vanillin formation was observed following administration of ferulic acid while no metabolism of p-coumaric acid and caffeic acid was observed. In an independent approach, VpVAN of SEQ ID NO:1 was expressed in yeast together with *Arabidopsis thaliana* UGT72E2 (SEQ ID NO:3). *Arabidopsis thaliana* UGT72E2 catalyzes glucosylation of ferulic acid enabling testing of the ability of vanillin synthase to use ferulic acid glucoside as a substrate. FIG. 12 shows that yeast cells expressing *Arabidopsis thaliana* UGT72E2 (SEQ ID NO:3) synthesizes ferulic acid glucoside when grown on synthetic media comprising 2.5 mM ferulic acid (see FIG. 12). Biosynthetic studies were carried out with yeast harboring stably integrated VAN codon optimized for yeast expression or with truncated VAN devoid of the signal peptide (SEQ ID NO:17; herein also designated vp Δsp van) or with truncated VAN devoid of the signal peptide codon optimized for yeast expression (FIG. 3). The yeast strains were incubated with different putative substrates for 72 h before metabolite profiles were determined by LC-MS. Formation of vanillin glucoside was observed with ferulic acid as substrate and with both versions of VAN tested. Highest conversion was obtained using the truncated version of Δsp van. In no case was carbon chain shortening of caffeic acid or p-coumaric acid observed. The results are shown in FIG. 3. Administrating yeast with ferulic acid also resulted in production of aroma compound 4-vinylguaiacol glucoside. Thus it is possible to make vanillin glucoside in two steps in yeast by feeding with or production of ferulic acid.

Figure 2:
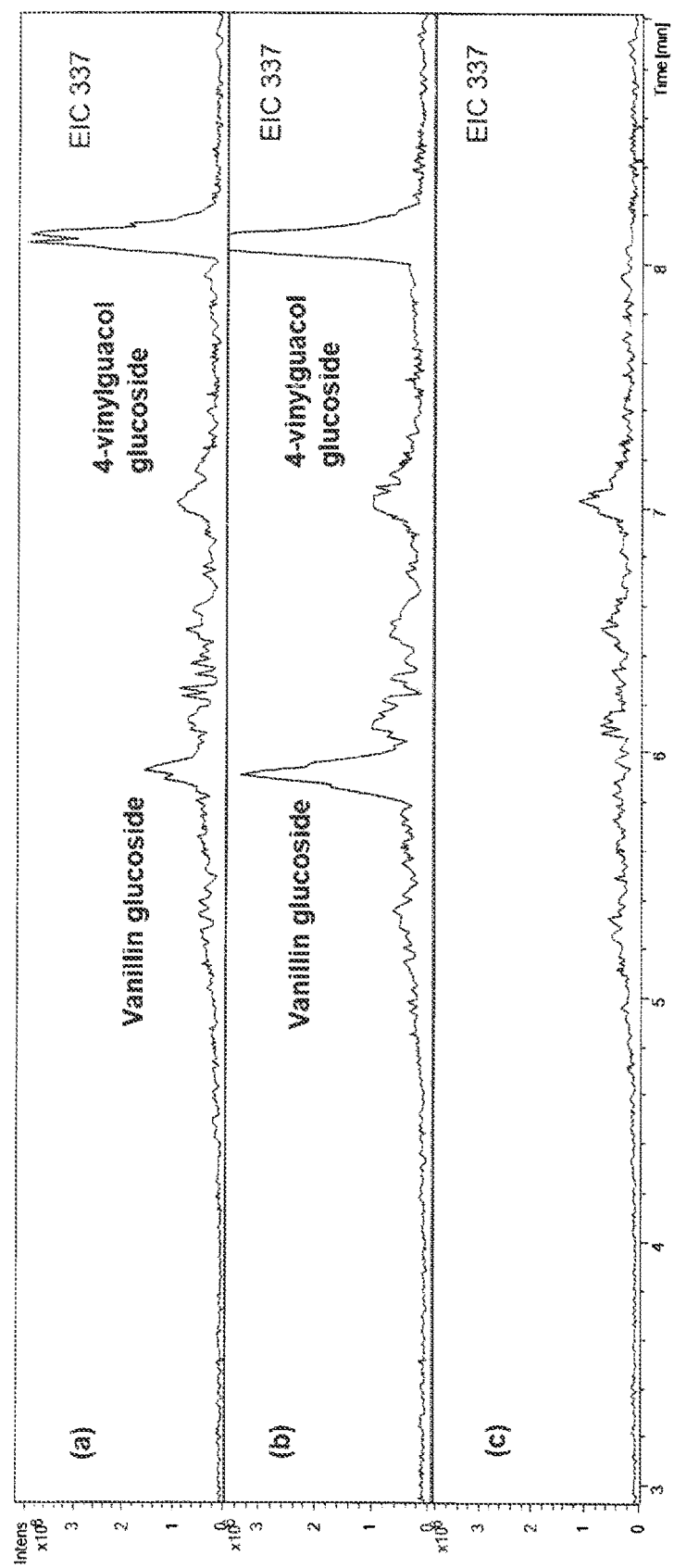
FIG. 2 shows formation of vanillin glucoside by yeast strains having VpVAN stably integrated into the yeast chromosome together with *Arabidopsis thaliana* UGT72E2. The yeast strains were grown in Delft medium supplemented with 8% molasses before metabolite profiles were determined by LC-MS. (EIC 317—Extracted ion chromatogram m/z Vanillin glucoside mw+22)
(a) Wt VpVAN
(b) VpVAN yeast codon optimized
(c) Negative control (yeast strain Y06460)

In the production of sugar from sugar beets, sugar cane or sorghum, molasses are obtained as viscous by-products. Molasses are known to contain hydroxycinnamic acids including ferulic acid. To examine whether this cheap waste product could be used as a starting material for vanillin glucoside production, yeasts harboring stably integrated VAN codon optimized for yeast (i.e. encoding VpVAN of SEQ ID NO:1) was grown on molasses. Vanillin glucoside formation was observed highlighting the potential of this enzyme for industrial natural vanillin glucoside production using inexpensive starting materials (FIG. 2).

Figure 4:
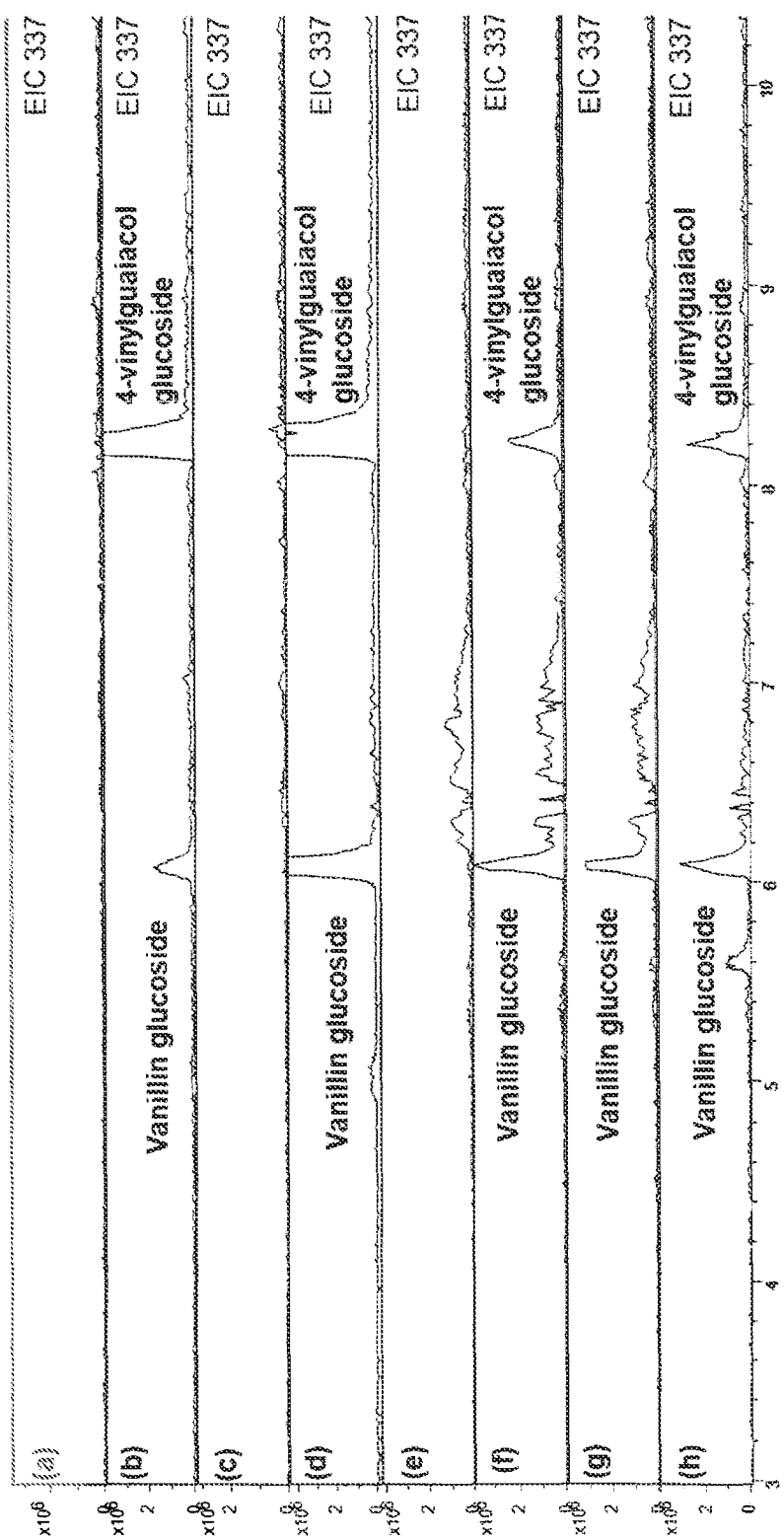
FIG. 4 shows Substrate specificity of VpVAN tested with ferulic acid and ferulic acid glucoside. LC-MS extracted ion chromatograms show that VpVAN is able to catalyze the chain cleavage of both ferulic acid and ferulic acid glucoside. (EIC 337—Extracted ion chromatogram m/z Vanillin glucoside mw+22).
(a) Negative control fed with ferulic acid
(b) VpVAN::VpUGT72U1 fed with ferulic acid
(c) VpVAN fed with ferulic acid
(d) VpVAN::AtUGT72E2 fed with ferulic acid
(e) Negative control fed with ferulic acid glucoside
(f) VpVAN::VpUGT72 fed with ferulic acid glucoside
(g) VpVAN fed with ferulic acid glucoside
(h) VpVAN::AtUGT72E2 fed with ferulic acid glucoside

The substrate specificity of VpVAN was furthermore tested with ferulic acid and ferulic acid glucoside. This experiment performed to detect formation of vanillin glucoside. VpUGT72U1 is able to glycosylate vanillin but not able to glycosylate ferulic acid while AtUGT72E2 is able to glycosylate both ferulic acid and vanillin. VpUGT72U1 included yeast constructs enable to test the VpVAN substrate specificity to ferulic acid and ferulic acid glucoside. LC-MS extracted ion chromatograms show that VpVAN is able to catalyze the chain cleavage of both ferulic acid and ferulic acid glucoside (see FIG. 4)

Example 3

Figure 5:
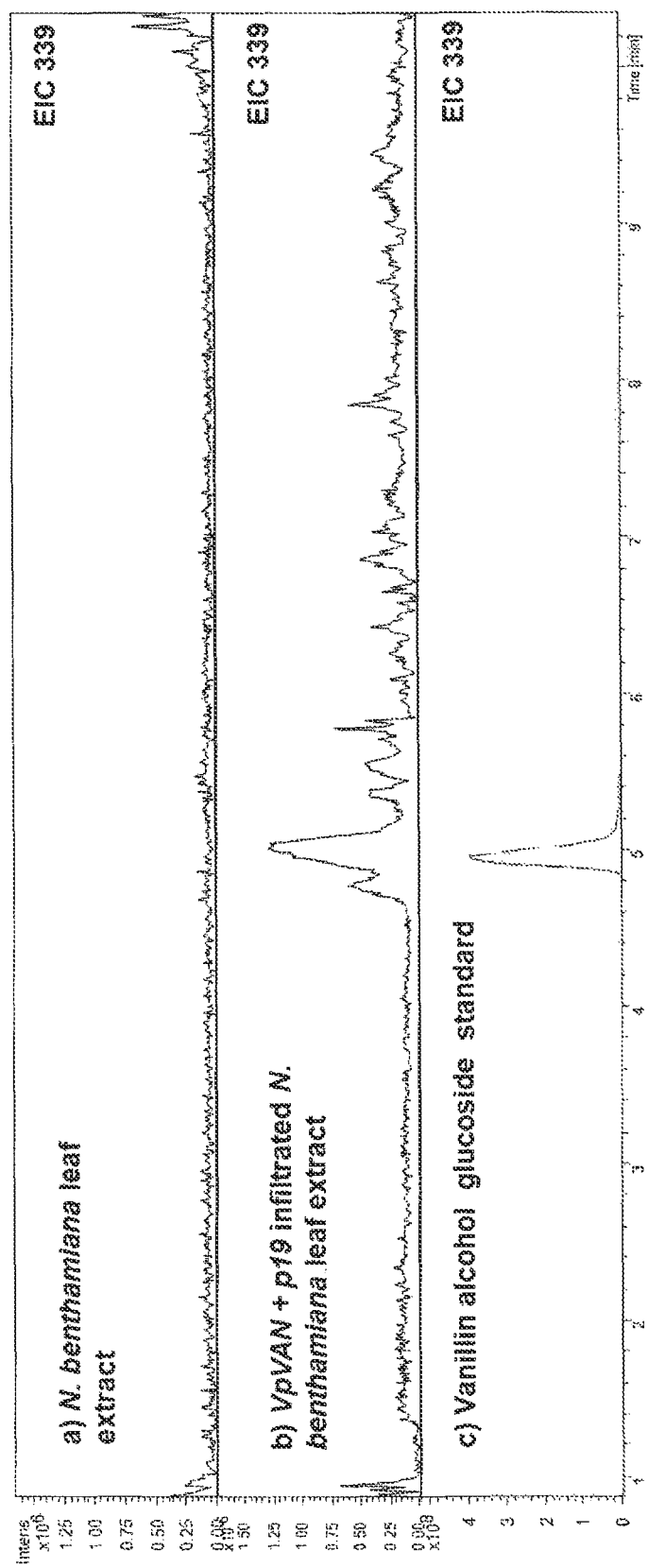
FIG. 5 shows biological activity of vanillin synthase after a transient expression in *Nicotiana benthamiana*. VpVAN was transferred to *Agrobacterium tumefaciens* and co-infiltrated with an *A. tumefaciens* strain harboring the p19 gene silencing suppressor in *N. benthamiana* leaves. Four days after inoculation, the infiltrated tobacco leaves were harvested and subjected to metabolite profiling by LC-MS. The profiling showed VpVAN dependent formation of vanillyl alcohol glucoside. (EIC 339—Extracted ion chromatogram m/z Vanillin alcohol glucoside mw+22).

Transient Expression of VpVAN in *Nicotiana benthamiana* to Make Vanillin from Inherent Ferulic Acid This example describes that it is possible to use VpVAN for production of vanillin in plants which do not normally produce vanillin. VpVAN activity in a plant different from *V. planifolia* was assessed by transient expression in *Nicotiana benthamiana* leaves. Gene expression constructs encoding VpVAN of SEQ ID NO:1 were transferred to *Agrobacterium tumefaciens* and co-infiltrated with an *A. tumefaciens* strain harbouring the p19 gene silencing suppressor into *N. benthamiana* leaves. Four days after inoculation, the infiltrated tobacco leaves were harvested and subjected to metabolite profiling by LC-MS. The results are shown in FIG. 5. The profiling showed formation of vanillyl alcohol glucoside only in tobacco leaves from plants transfected with gene expression constructs encoding VpVAN. Vanillyl alcohol is a known metabolite of vanillin in living cells, likely produced in order to reduce cellular toxicity of the aldehyde vanillin. These results thus show that vanillin can be produced from ferulic acid in other plants than *V. planifolia*.

Example 4

Stable Expression of VpVAN in Tobacco for Vanillin Glucoside Production

This example describes de novo formation of vanillin glucoside in stably transformed lines of Tobacco, *Nicotiana tabacum*. In order to ensure accumulation of vanillin glucoside rather than vanillyl alcohol glucoside in a plant it is preferable to co-express the VpVAN enzyme with an appropriate highly efficient vanillin glycosyltransferase enzyme. VpVAN (SEQ ID NO:1) is therefore stably co-expressed with *A. thaliana* UGT72E2 (SEQ ID NO:3) in a transformant line of *N. tabacum*. Firstly, a nucleic acid encoding UGT72E2 of SEQ ID NO:3 is cloned into the multiple cloning site of a plant transformation vector such as one from the pCAMBIA series, which enables expression of the genes in the plant under the control of the strong, constitutive cauliflower mosaic virus CaMV35S promoter. The vector harbors both a bacterial selection gene and a plant selection gene. The vector harboring the nucleic acid encoding UGT72E2 of SEQ ID NO:3 is transformed into *Agrobacterium tumefaciens* C58C1/pGV3850 by electroporation as described in Wen-Jun et al., 1983. The *A. tumefaciens* cells are grown on selective medium and positive transformants are grown over night. Bacteria from plate is suspended in 20 mL of Minimal A medium, density is adjusted to an OD600 of 0.9-1.0 and ca. 20 0.5 cm *N. tabacum* leaf squares (4-5 week old tissue culture grown plants) are transferred to bacterial solution (deep well Petri dish). Leaf squares are swirled in solution and left for 5 minutes, after which they are removed and blotted dry, then transferred with adaxial side onto solid RMOP, about 10 pieces per plate. The plates are incubated in dark at 28° C. for: 2-3 days *A. tumefaciens* 5 days, after which the leaf pieces are transferred onto solid RMOP-TCH, with abaxial surface in contact with media, then incubated for 2-3 weeks in the light at 28° C., with 16 hours daylight per day. The material is sub-cultured every 2 weeks or so until shoots appear, then plantlets are transferred to MST-TCH pots and incubated with 16 hours daylight for 1-2 weeks, and when roots form the plants are transferred to soil in the glasshouse. Plant material from the UGT72E2-expressing transgenic tobacco plants are used for the next transformation. Nucleic acid encoding VpVAN of SEQ ID NO:1 is cloned into a plant expression vector as described above, and the whole procedure is repeated, to finally obtain transgenic tobacco plants co-expressing UGT72E2 and VpVAN. Plant material from the final transgenic plants is harvested and lysed and vanillin glucoside content is determined in the leaf material from the transgenic plant. No vanillin glucoside is seen in wildtype tobacco plants.

Example 5

Increased Production of Vanillin

Administrating yeast with ferulic acid as described in Example 2 also resulted in production of aroma compound 4-vinylguaiacol in high concentrations due to yeast ferulate decarboxylase activity. *S. cerevisiae* ferulic acid decarboxylase (FADase) belongs to superfamily PAD and catalyzes the transformation of ferulic acid to 4-vinylguaiacol via non-oxidative decarboxylation.

In order to increase vanillin production the FADase gene is knocked out in VpVAN-transformed yeast using conventional technology. In particular, the FADase gene is knocked out in the yeast strains described herein above in Example 2.

The adjacent PAD1 and FDC1 genes of *S. cerevisiae* are disrupted by PCR amplifying *Klyveromyces lactis* LEU2 (leucine auxotrophic selection marker) using primers with 74-77 bp tails homologous to the front and back end of PAD1 and FDC1, respectively. The yeast strain is then transformed with the PCR product, resulting in transformants having no PAD1 and FDC1 activity and able to grow on plates not supplemented with leucine.

The following primers are used:

```
LEU2Δpad1Δfad1_F
                                         (SEQ ID NO: 19)
AACATAATGCTGCAAATATAGATTGATTTCAATCTACGGAGTCC AACGCATTGAGCAGCTTCAATTGAGTAGATatgtctaagaatat cgttgtcctaccgg LEU2Δpad1Δfad1_R
                                         (SEQ ID NO: 20)
CGTGGAGTATAAAAGTTCGGAAAATTTTATTTAAAATCTGATTA TATGGTTTTTCTTCCGTAGAAAGTCTATGGCAAttaagccaaga tttccttgacagccttggcgatagc
```

Production of 4-vinylguaiacol glucoside in yeast expressing both VpVAN (SEQ ID NO:1) and UGT72E2 (SEQ ID NO:3) but having disrupted the PAD1 and FDC1 genes (this yeast strain is also named VpVAN+AtUGt72E2 Δpad1 Δfad1 herein) was determined. Results are provided in FIG. 9. It is clear that VpVAN+AtUGt72E2 Δpad1 Δfad1 yeast strain does not produce 4-vinylguaiacol glucoside, whereas yeast expressing VpVAN (SEQ ID NO:1) and UGT72E2 (SEQ ID NO:3)(named VpVAN+AtUGt72E2) has high expression.

Example 6

Production of Vanillin in Yeast

In order to enable production of vanillin without addition of ferulic acid to the medium the VpVAN-transformed yeast is further transformed with nucleic acids encoding the enzymes involved in synthesis of ferulic acid.

Strain 1

S. cerevisiae transformed with a nucleic acid encoding VpVAN of SEQ ID NO:1 and a nucleic acid encoding *Arabidopsis thaliana* UGT72E2 of SEQ ID NO:3 prepared as described in Example 3 with the following nucleic acids each under control of a promoter directing expression in *S. cerevisiae*:
1. phenylalanine ammonia-lyase (Vannelli et al 2006, Shin et al 2012)
2. *Arabidopsis thaliana* CYP73A5 (GenBank accession number: U37235)
3. tyrosine ammonia-lyase (Vannelli et al 2006, Shin et al 2012)
4. 4-coumarate-CoA ligase *Arabidopsis thaliana* 4-coumarate:CoA ligase 3 (GenBank accession number AF106088_1)
5. *Nicotiana tabacum* Shikimate O-hydroxycinnamoyl-transferase (GenBank accession number Q8GSM7)
6. *Arabidopsis thaliana* p-coumarate 3-hydroxylase (CYP98A3) (GenBank accession number: AEC09893.1)
7. *Arabidopsis thaliana* caffeoyl-CoA O-methyltransferase (GenBank accession number Q9C5D7)

Strain 2

S. cerevisiae transformed with a nucleic acid encoding VpVAN of SEQ ID NO:1 and a nucleic acid encoding *Arabidopsis thaliana* UGT72E2 of SEQ ID NO:3 prepared as described in Example 3 with the following nucleic acids each under control of a promoter directing expression in *S. cerevisiae*:
1. phenylalanine ammonia-lyase (Vannelli et al 2006, Shin et al 2012)
2. *Arabidopsis thaliana* CYP73A5 (GenBank accession number: U37235)
3. 4-coumarate-CoA ligase *Arabidopsis thaliana* 4-coumarate:CoA ligase 3 (GenBank accession number AF106088_1)
4. *Nicotiana tabacum* Shikimate O-hydroxycinnamoyl-transferase (GenBank accession number Q8GSM7)
5. *Arabidopsis thaliana* p-coumarate 3-hydroxylase (CYP98A3) (GenBank accession number: AEC09893.1)
6. *Arabidopsis thaliana* p-coumarate 3-hydroxylase (CYP98A3)(SEQ ID NO:7), The transformed yeast cells are grown in synthetic media containing galactose and vanillin glucoside is isolated from the growth medium.

Example 7

The Catalytic Activity of Vanillin Synthase in the Presence and Absence of a Putative Pre-Peptide A general sequence identity search using GenBank showed that the VpVan sequence showed a high sequence identity to cysteine proteinases. Highest sequence identity (77%) was found to the *Elaeis guineensis* cysteine proteinase belonging to the aleurain class of cysteine proteinases (MEROPS—the peptidase database). Interestingly, alignments unequivocally demonstrated that the VpVan sequence contained the three key active site residues required for proteinase activity (Fan, J. et al. Expression of a senescence-associated cysteine protease gene related to peel pitting of navel orange (*Citrus sinensis* L. Osbeck. *Plant Cell Tiss Org* 98, 281-289 (2009)). To test whether the activity of the enzyme enhances in the absence of the pre peptide or if it changes the substrate specificity, we have truncated first 137aa from VpVan (vp Δ137 van) and first 61aa from VpVAN. The activity of the enzymes were tested in vitro using coupled transcription/translation (TNT) assay. Thus, Wt VpVAN encodes the polypeptide of SEQ ID NO:1, wt vp Δsp van encodes the polypeptide of SEQ ID NO:17, vp Δ137 van encodes aa 138 to 356 of SEQ ID NO:1 and vp Δ61 van encodes aa 62 to 356 of SEQ ID NO:1.

The TNT® Quick Coupled Transcription/Translation kit for PCR-generated DNA (Promega) was used to produce proteins of interest directly from PCR products. L-[$^{35}$S]-Methionine was included to permit monitoring of the radiolabeled proteins formed following separation by SDS-PAGE and visualized by incubating dried gels for 48 h on phosphorimager screens which were scanned with a STORM 860 molecular imager (Molecular Dynamics).

Proteins produced in coupled in vitro transcription/translation assays were analyzed for their enzyme catalytic abilities by incubation of aliquots (10 µl) with 0.5 mM to 5 mM of the following substrates: ferulic acid (Sigma), p-coumaric acid (Sigma), caffeic acid (Sigma), ferulic acid glucoside, p-coumaric acid glucoside, caffeic acid glucoside, caffeoyl-Coenzyme A (MicroCombiChem e.K.), p-coumaryl-Coenzyme A (MicroCombiChem e.K.), feruloyl-Coenzyme A (MicroCombiChem e.K.) or sinapyl-Coenzyme A (MicroCombiChem e.K.) in 400 mM Tris/HCl (pH 8), 20 mM $MgCl_2$ and 2.5 mM dithiothreitol (DTT) (total volume: 50 µl). Enzyme assays were carried out in the presence and absence of 2.5 mM dithiothreitol (DTT), 0.1 mM ATP and 0.1 mM $NAD^+$. Aliquots (10 µl) were withdrawn at specific time points and enzyme activity stopped by MeOH addition (25 µl, 25% (v/v)) and heating (45 C, 15 min). Samples were cooled on ice (30 min), centrifuged (10.000 rpm, 10 min) in microtiter filter plates (Merck Millipore) and the filtrate was finally analyzed by LC-MS.

Figure 6:
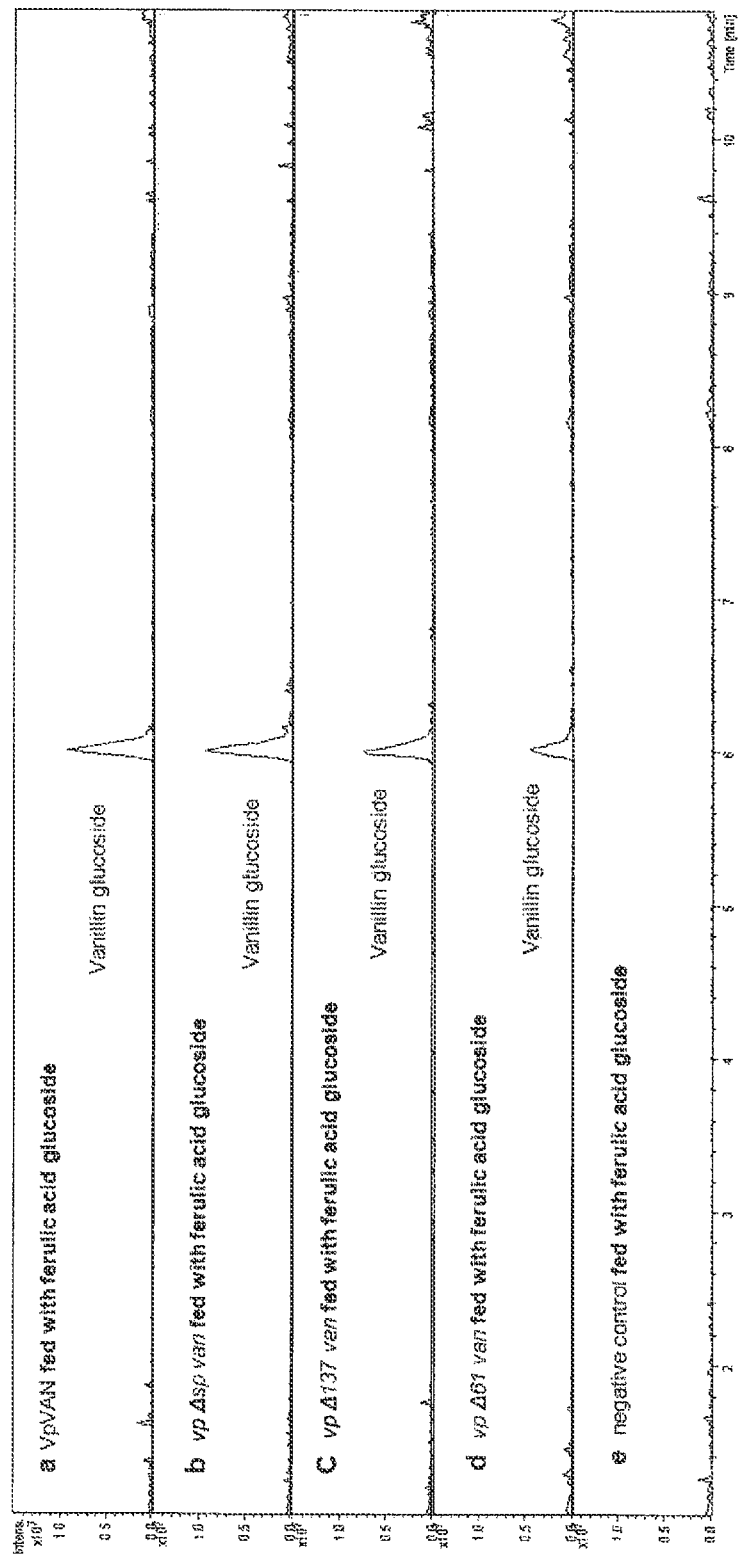
FIG. 6 shows a LC-MS chromatogram from in vitro coupled transcription and translation (TNT) assays. The figure shows generation of significant amounts of vanillin glucoside (peak at 6 min.) after in vitro incubation with ferulic acid glucoside.
(a) Wt VpVAN (SEQ ID NO:1)
(b) wt vp Δsp van (aa 22-356 of SEQ ID NO:1)
(c) vp Δ137 van (aa 138-356 of SEQ ID NO:1)
(d) vp Δ61 van (aa 62-356 of SEQ ID NO:1)
(e) Negative control FIG. 7A) shows biological activity of vanillin synthase after transient expression in *Nicotiana benthamiana* leaves. The *Nicotiana benthamiana* has been transformed with nucleic acids encoding:
a) Wt VpVAN (SEQ ID NO:1)
b) wt vp Δ137 van (aa 138-356 of SEQ ID NO:1)
c) wt vp Δ66 van (aa 138-356 of SEQ ID NO:1)
d) Negative control (p19 infiltrated tobacco leaf)

The results are shown in FIG. 6. The experiments show that processing of VpVan by removal of an N-terminal sequence is not necessary for activity towards ferulic acid glucoside (see FIG. 6).

Example 8

The Catalytic Activity of Vanillin Synthase in the Presence and Absence of a Putative Pre-Peptide In Vivo as Analyzed Following Transient Expression in Tobacco The biological activity observed following expression of VpVAN (including the ER-targeting signal peptide) was also assessed in vivo by transient expression in leaves of *N. benthamiana* in the absence of any exogenously added substrates. Gene constructs were transferred to *Agrobacterium tumefaciens* and co-infiltrated with an *A. tumefaciens* strain harbouring the p19 gene silencing suppressor. LC-MS profiling showed VpVAN-dependent formation of vanillyl alcohol glucoside. The vanillyl alcohol glucoside arises by reduction of vanillin by an alcohol dehydrogenase (E.C.1.1.1.1) and subsequent glucosylation of the primary alcohol group of vanillyl alcohol. For biotechnological production of vanillin glucoside in plants other than *Vanilla sp.* by introduction of vanillin synthase, then it is preferred that said host organism co-expresses a UGT that effectively glucosylates the free vanillin formed into the corresponding glucoside before its reduction into vanillyl alcohol.

Moreover, wt vp Δ137 van (encodes aa 138 to 356 of SEQ ID NO:1) and wt vp Δ66 van (encodes aa 67 to 356 of SEQ ID NO:1) were also included in this study to investigate the importance of secondary modifications of VAN.

The transient expression of VpVAN and the truncated versions thereof described above in leaves of *Nicotiana benthamiana* was obtained as follows. Overnight cultures of an *Agrobacterium tumefaciens* strain AGL1 containing the recombined pJAM1502 vector harboring the cDNA of interest (Wt VpVAN or wt vp Δ137 van or wt vp Δ61 van) and *A. tumefaciens* strain AGL1 carrying the recombined pJAM1502 vector harboring the gene silencing inhibitor protein 19 (p19) were harvested by centrifugation and resuspended ($OD_{600}$=2.0) in 10 mM MES pH 5.5, 10 mM $MgCl_2$ and 100 μM acetosyringone. After incubation (4 h, RT), the two *A. tumefaciens* strains were used to co-infiltrate leaves of 3-weeks-old *Nicotiana benthamiana* plants grown at 24.0 (day) and 17C (night). After 4 or 5 days, leaf discs (1 cm diameter) were stamped out from the infiltrated leaves and metabolites extracted in 60% (v/v) MeOH for LC-MS analysis. The results are shown in FIG. 7A).

Introduction of all three constructs was found to result in vanillyl alcohol glucoside production.

The VpVan sequence showed high sequence identity to proteins belonging to the family cysteine proteinases (see above). We identified a protein belonging to the family of cysteine proteinases in tobacco in which the amino acid sequence identity to VpVan is 71% (SEQ ID NO:22). An alignment was prepared (see FIG. 10). A construct was prepared where the VpVAN signal peptide (aa 1 to 21 of SEQ ID NO:1) was replaced the signal peptide of SEQ ID NO:22 identified using signalP 4.1 software (available from Center for Biological Sequence analysis, Technical University of Denmark). This signal peptide is aa 1 to 21 of SEQ ID NO:22. A cleavage site was identified at aa 135 to 141 of SEQ ID NO:1 with cleavage after position residue 137 (DGV/LPVT). The amino acids of SEQ ID NO:22 corresponding to aa 135 to 141 of SEQ ID NO:1 were identified to be aa 140 to 146 of SEQ ID NO:22 using the alignment of FIG. 10 and aa 135-141 of SEQ ID NO:1 were replaced with aa 140 to 146 of SEQ ID NO:22. Thus, the signal peptide and the protease cleavage site were replaced with signal peptide and a protease cleavage site from the tobacco cysteine protease. Thus the resulting polypeptide consists of [aa 1 to 21 of SEQ ID NO:22]-[aa 22 to 134 of SEQ ID NO:1-[aa 140 to 146 of SEQ ID NO:22]-[aa 142 to 356 of SE ID NO1]. The nucleic acid encoding this protein is termed vp nb Δsp Δ137van herein and is provided as SEQ ID NO:24. This gene construct was transferred to *A. tumefaciens* and infiltrated to tobacco essentially as described in this example above for wild type VpVAN and vanillin alcohol glucoside production was analysed by LC-MS profiling. The results are shown in FIG. 7B.

Example 9

The Catalytic Activity of GhVAN (Vanillin Synthase from *Glechoma hederacea*) Monitored In Vivo Following Transient Expression in Tobacco The VpVan sequence was found to show 71% amino acid sequence identity to GhVAN, a novel gene cloned from *Glechoma hederacea* (Ground ivy) belonging to the Lamiaceae family. The sequence of GhVAN is provided as SEQ ID NO:21). A study of volatile constituents released by *G. hederacea* showed that this plant release traces of vanillin (N Radulovic 2010).

Transient expression of GhVAN in tobacco performed essentially as descried in Example 8 demonstrated that expression of this gene results in accumulation of vanillin alcohol glucoside in tobacco i.e. the enzyme has similar functional property to VpVAN (see FIG. 8).

REFERENCES

Radulovic N, Dordevic N, Markovic M, Palic R. Volatile constituents of *Glechoma* hirsute Waldst. & Kit. and *G. hederacea* L. (Lamiaceae). Bulletin of the Chemical Society of Ethiopia 24: 67-76

Podstolski A, Havkin-Frenkel D, Malinowski J, Blount J W, Kourteva G and Dixon R A. Unusual 4-hydroxybenzaldehyde synthase activity from tissue cultures of the vanilla orchid *Vanilla* planifolia.

Phytochemistry 61 (2002) 611-620.

Shin S Y, Jung S M, Kim M D, Han N S, Seo J H. Production of resveratrol from tyrosine in metabolically engineered *Saccharomyces cerevisiae.*

Enzyme Microb Technol. 2012 Sep. 10; 51(4):211-6. Epub 2012 Jun. 28.

Vannelli T, Wei Qi W, Sweigard J, Gatenby A A, Sariaslani F S. Production of p-hydroxycinnamic acid from glucose in *Saccharomyces cerevisiae* and *Escherichia coli* by expression of heterologous genes from plants and fungi.

Metab Eng. 2007 March; 9(2):142-51. Epub 2006 Nov. 15.

Wen-Jun S., Forde B. G. (1983) Nucleic Acids Res. 17:8385.

The invention claimed is:

1. A method of producing vanillin, vanillyl alcohol, vanillin glucoside, and/or vanillyl alcohol glucoside, the method comprising the steps of:
   (a) providing a microbial organism that comprises a heterologous nucleic acid encoding a vanillin synthase, wherein the vanillin synthase is capable of catalyzing conversion of ferulic acid or a ferulic acid derivative to form vanillin, vanillyl alcohol, vanillin glucoside, and/or vanillyl alcohol glucoside;
   (b) cultivating the microbial organism in the presence of ferulic acid and/or a ferulic acid derivative in culture medium supporting growth of the microbial organism; and
   (c) isolating vanillin, vanillyl alcohol, vanillyl alcohol glucoside, and/or vanillin glucoside from the microbial organism and/or from the culture medium;
   wherein the vanillin synthase capable of catalyzing the conversion of ferulic acid or a ferulic acid derivative to form vanillin comprises the amino acid sequence of SEQ ID NO: 1 or a functional homolog thereof, wherein the functional homolog thereof comprises:
   (i) an amino acid sequence with at least 99% identity to SEQ ID NO: 1;
   (ii) an amino acid sequence with at least 99% identity to SEQ ID NO: 17;
   (iii) an amino acid sequence with at least 99% identity to amino acids 62 to 356 of SEQ ID NO: 1;
   (iv) an amino acid sequence with at least 98% identity to amino acids 138 to 356 of SEQ ID NO: 1;

(v) an amino acid sequence with at least 98% identity to SEQ ID NO: 21; or
(vi) an amino acid sequence with at least 93% identity to the sequence encoded by SEQ ID NO: 24.

2. The method of claim 1, wherein step (b) comprises cultivating the microbial organism in the presence of ferulic acid.

3. The method of claim 2, wherein the culture medium comprises at least 1 mM ferulic acid.

4. The method of claim 1, wherein step (b) comprises cultivating the microbial organism in the presence of a ferulic acid derivative.

5. The method of claim 4, wherein the ferulic acid derivative is ferulic acid glucose ester, ferulic acid glucoside, feruloyl-coA, ferulic acid shikimate, or feruloyl-quinate.

6. The method of claim 4, wherein the ferulic acid derivative is ferulic acid glucoside.

7. The method of claim 6, wherein the culture medium comprises at least 1 mM ferulic acid glucoside.

8. The method of claim 6, wherein step (c) comprises isolating vanillin glucoside.

9. The method of claim 1, further comprising deglucosylating the vanillin glucoside.

10. The method of claim 9, wherein deglucosylating vanillin glucoside comprises contacting the vanillin glucoside with a glucosidase.

11. The method of claim 10, wherein the glucosidase is a beta-glucosidase.

12. The method of claim 1, wherein the medium comprises molasses.

13. The method of claim 1, wherein the medium comprises eugenol.

14. The method of claim 1, wherein the microbial organism comprises reduced, disrupted, or eliminated ferulic acid decarboxylase (FADase) activity.

15. The method of claim 14, wherein an endogenous phenylacrylic acid decarboxylase (PAD1) or ferulic acid decarboxylase (FDC1) gene in the microbial organism is reduced, inactivated, disrupted, or deleted, in full or in part.

16. The method of claim 14, wherein the expression of an endogenous PAD1 or FDC1 gene, or the expression of a protein encoded by an endogenous PAD1 or FDC1 gene in the microbial organism is reduced, disrupted, or eliminated, in full or in part.

17. The method of claim 14, wherein the activity of a protein encoded by an endogenous PAD1 or FDC1 gene in the microbial organism is reduced, disrupted, or eliminated, in full or in part.

18. The method of claim 1, wherein the vanillin synthase capable of catalyzing conversion of ferulic acid or a ferulic acid derivative to form vanillin comprises the amino acid sequence of SEQ ID NO: 21.

19. The method of claim 1, wherein the vanillin synthase capable of catalyzing the conversion of ferulic acid or a ferulic acid derivative to form vanillin comprises-amino acids 138 to 356 of SEQ ID NO: 1.

20. The method of claim 19, wherein the vanillin synthase capable of catalyzing the conversion of ferulic acid or a ferulic acid derivative to form vanillin further comprises amino acids 62 to 137 of SEQ ID NO: 1.

21. The method of claim 20, wherein the vanillin synthase capable of catalyzing the conversion of ferulic acid or a ferulic acid derivative to form vanillin further comprises amino acids 22 to 61 of SEQ ID NO: 1.

22. The method of claim 1, wherein the vanillin synthase capable of catalyzing the conversion of ferulic acid or a ferulic acid derivative to form vanillin comprises the amino acid sequence of SEQ ID NO: 1.

23. The method of claim 1, wherein the vanillin synthase capable of catalyzing the conversion of ferulic acid or a ferulic acid derivative to form vanillin comprises the amino acid sequence encoded by SEQ ID NO: 24.

* * * * *

SEQUENCE LISTING

```
<160> NUMBER OF SEQ ID NOS: 26

<210> SEQ ID NO 1
<211> LENGTH: 356
<212> TYPE: PRT
<213> ORGANISM: Vanilla planifolia

<400> SEQUENCE: 1

Met Ala Ala Lys Leu Leu Phe Phe Leu Leu Phe Leu Val Ser Ala Leu
1               5                   10                  15

Ser Val Ala Leu Ala Gly Phe Glu Glu Asp Asn Pro Ile Arg Ser Val
            20                  25                  30

Thr Gln Arg Pro Asp Ser Ile Glu Pro Ala Ile Leu Gly Val Leu Gly
        35                  40                  45

Ser Cys Arg His Ala Phe His Phe Ala Arg Phe Ala Arg Arg Tyr Gly
    50                  55                  60
```

```
Lys Ser Tyr Gly Ser Glu Glu Ile Lys Lys Arg Phe Gly Ile Phe
 65                  70                  75                  80

Val Glu Asn Leu Ala Phe Ile Arg Ser Thr Asn Arg Lys Asp Leu Ser
                 85                  90                  95

Tyr Thr Leu Gly Ile Asn Gln Phe Ala Asp Leu Thr Trp Glu Glu Phe
            100                 105                 110

Arg Thr Asn Arg Leu Gly Ala Ala Gln Asn Cys Ser Ala Thr Ala His
        115                 120                 125

Gly Asn His Arg Phe Val Asp Gly Val Leu Pro Val Thr Arg Asp Trp
    130                 135                 140

Arg Glu Gln Gly Ile Val Ser Pro Val Lys Asp Gln Gly Ser Cys Gly
145                 150                 155                 160

Ser Cys Trp Thr Phe Ser Thr Thr Gly Ala Leu Glu Ala Ala Tyr Thr
                165                 170                 175

Gln Leu Thr Gly Lys Ser Thr Ser Leu Ser Glu Gln Gln Leu Val Asp
            180                 185                 190

Cys Ala Ser Ala Phe Asn Asn Phe Gly Cys Asn Gly Gly Leu Pro Ser
        195                 200                 205

Gln Ala Phe Glu Tyr Val Lys Tyr Asn Gly Gly Ile Asp Thr Glu Gln
    210                 215                 220

Thr Tyr Pro Tyr Leu Gly Val Asn Gly Ile Cys Asn Phe Lys Gln Glu
225                 230                 235                 240

Asn Val Gly Val Lys Val Ile Asp Ser Ile Asn Ile Thr Leu Gly Ala
                245                 250                 255

Glu Asp Glu Leu Lys His Ala Val Gly Leu Val Arg Pro Val Ser Val
            260                 265                 270

Ala Phe Glu Val Lys Gly Phe Asn Leu Tyr Lys Lys Gly Val Tyr
        275                 280                 285

Ser Ser Asp Thr Cys Gly Arg Asp Pro Met Asp Val Asn His Ala Val
    290                 295                 300

Leu Ala Val Gly Tyr Gly Val Glu Asp Gly Ile Pro Tyr Trp Leu Ile
305                 310                 315                 320

Lys Asn Ser Trp Gly Thr Asn Trp Gly Asp Asn Gly Tyr Phe Lys Met
                325                 330                 335

Glu Leu Gly Lys Asn Met Cys Gly Val Ala Thr Cys Ala Ser Tyr Pro
            340                 345                 350

Ile Val Ala Val
            355

<210> SEQ ID NO 2
<211> LENGTH: 1071
<212> TYPE: DNA
<213> ORGANISM: Vanilla planifolia

<400> SEQUENCE: 2
atggcagcta agctcctctt cttcctactc ttcctggtct ccgccctctc cgtcgcgctc      60
gccggtttcg aagaagacaa tccaatccgg tccgttacac aaaggcctga ctcgattgag     120
cctgccatcc tcggcgtcct tggcagttgc cgccacgcct ccacttcgc acggttcgcc      180 cgcaggtacg ggaagagcta cggatcggag gaggagatca agaagaggtt cgggatcttc     240
gtggagaatc tagcgtttat ccggtccact aatcggaagg atctgtcgta taccctagga     300
atcaaccaat cgccgaccct gacctgggag gaattccgga ccaatcgcct ggtgcggcg      360 cagaactgct cggcgactgc gcatggaaac caccggtttg tcgatggcgt gcttcctgta     420
```

```
acgagggatt ggagggagca agggatagtg agccctgtaa aggaccaagg aagctgtgga      480
tcttgctgga ctttcagtac tactggagca ctagaggctg catatacaca gctaactgga      540
aagagcacat cattatctga acagcaactt gtggactgtg cctcagcatt caataacttt      600
ggatgcaatg gaggtttgcc ttcccaagcc tttgaatacg ttaagtacaa tggaggcatc      660
gacacagaac agacttatcc ataccttggt gtcaatggta tctgcaactt caagcaggag      720
aatgttggtg tcaaggtcat tgattcgata aacatcaccc tgggtgctga ggatgagttg      780
aagcatgcag tgggcttggt gcgtccagtt agcgttgcat ttgaggttgt gaaaggtttc      840
aatctgtaca agaaaggtgt atacagcagt gacacctgtg aagagatcc  aatggatgtg      900
aaccacgcag ttcttgccgt cggttatgga gtcgaggacg ggattcctta ttggctcatc      960
aagaactcat ggggtacaaa ttggggtgac aatggctact ttaagatgga actcggcaag     1020
aacatgtgtg tgttgcaac  ttgcgcatct tatcccattg tggctgtgta g              1071
```

<210> SEQ ID NO 3
<211> LENGTH: 481
<212> TYPE: PRT
<213> ORGANISM: Arabidopsis thaliana

<400> SEQUENCE: 3

```
Met His Ile Thr Lys Pro His Ala Ala Met Phe Ser Ser Pro Gly Met
1               5                   10                  15

Gly His Val Ile Pro Val Ile Glu Leu Gly Lys Arg Leu Ser Ala Asn
                20                  25                  30

Asn Gly Phe His Val Thr Val Phe Val Leu Glu Thr Asp Ala Ala Ser
            35                  40                  45

Ala Gln Ser Lys Phe Leu Asn Ser Thr Gly Val Asp Ile Val Lys Leu
        50                  55                  60

Pro Ser Pro Asp Ile Tyr Gly Leu Val Asp Pro Asp His Val Val
65                  70                  75                  80

Thr Lys Ile Gly Val Ile Met Arg Ala Ala Val Pro Ala Leu Arg Ser
                85                  90                  95

Lys Ile Ala Ala Met His Gln Lys Pro Thr Ala Leu Ile Val Asp Leu
            100                 105                 110

Phe Gly Thr Asp Ala Leu Cys Leu Ala Lys Glu Phe Asn Met Leu Ser
        115                 120                 125

Tyr Val Phe Ile Pro Thr Asn Ala Arg Phe Leu Gly Val Ser Ile Tyr
    130                 135                 140

Tyr Pro Asn Leu Asp Lys Asp Ile Lys Glu Glu His Thr Val Gln Arg
145                 150                 155                 160

Asn Pro Leu Ala Ile Pro Gly Cys Glu Pro Val Arg Phe Glu Asp Thr
                165                 170                 175

Leu Asp Ala Tyr Leu Val Pro Asp Glu Pro Val Tyr Arg Asp Phe Val
            180                 185                 190

Arg His Gly Leu Ala Tyr Pro Lys Ala Asp Gly Ile Leu Val Asn Thr
        195                 200                 205

Trp Glu Glu Met Glu Pro Lys Ser Leu Lys Ser Leu Leu Asn Pro Lys
    210                 215                 220

Leu Leu Gly Arg Val Ala Arg Val Pro Val Tyr Pro Ile Gly Pro Leu
225                 230                 235                 240

Cys Arg Pro Ile Gln Ser Ser Glu Thr Asp His Pro Val Leu Asp Trp
                245                 250                 255
```

```
Leu Asn Glu Gln Pro Asn Glu Ser Val Leu Tyr Ile Ser Phe Gly Ser
            260                 265                 270

Gly Gly Cys Leu Ser Ala Lys Gln Leu Thr Glu Leu Ala Trp Gly Leu
        275                 280                 285

Glu Gln Ser Gln Gln Arg Phe Val Trp Val Arg Pro Pro Val Asp
    290                 295                 300

Gly Ser Cys Cys Ser Glu Tyr Val Ser Ala Asn Gly Gly Thr Glu
305                 310                 315                 320

Asp Asn Thr Pro Glu Tyr Leu Pro Glu Gly Phe Val Ser Arg Thr Ser
                325                 330                 335

Asp Arg Gly Phe Val Val Pro Ser Trp Ala Pro Gln Ala Glu Ile Leu
            340                 345                 350

Ser His Arg Ala Val Gly Gly Phe Leu Thr His Cys Gly Trp Ser Ser
        355                 360                 365

Thr Leu Glu Ser Val Val Gly Val Pro Met Ile Ala Trp Pro Leu
    370                 375                 380

Phe Ala Glu Gln Asn Met Asn Ala Ala Leu Leu Ser Asp Glu Leu Gly
385                 390                 395                 400

Ile Ala Val Arg Leu Asp Asp Pro Lys Glu Asp Ile Ser Arg Trp Lys
                405                 410                 415

Ile Glu Ala Leu Val Arg Lys Val Met Thr Glu Lys Glu Gly Glu Ala
            420                 425                 430

Met Arg Arg Lys Val Lys Lys Leu Arg Asp Ser Ala Glu Met Ser Leu
        435                 440                 445

Ser Ile Asp Gly Gly Leu Ala His Glu Ser Leu Cys Arg Val Thr
    450                 455                 460

Lys Glu Cys Gln Arg Phe Leu Glu Arg Val Val Asp Leu Ser Arg Gly
465                 470                 475                 480

Ala

<210> SEQ ID NO 4
<211> LENGTH: 716
<212> TYPE: PRT
<213> ORGANISM: Rhodosporidium toruloides

<400> SEQUENCE: 4

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140
```

-continued

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
            165                 170                 175

Thr Arg Gly His Ser Ala Val Arg Leu Val Val Leu Glu Ala Leu Thr
        180                 185                 190

Asn Phe Leu Asn His Gly Ile Thr Pro Ile Val Pro Leu Arg Gly Thr
    195                 200                 205

Ile Ser Ala Ser Gly Asp Leu Ser Pro Leu Ser Tyr Ile Ala Ala Ala
210                 215                 220

Ile Ser Gly His Pro Asp Ser Lys Val His Val His Glu Gly Lys
225                 230                 235                 240

Glu Lys Ile Leu Tyr Ala Arg Glu Ala Met Ala Leu Phe Asn Leu Glu
            245                 250                 255

Pro Val Val Leu Gly Pro Lys Glu Gly Leu Gly Leu Val Asn Gly Thr
        260                 265                 270

Ala Val Ser Ala Ser Met Ala Thr Leu Ala Leu His Asp Ala His Met
    275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
            325                 330                 335

Glu Gly Ser Arg Phe Ala Val His His Glu Glu Val Lys Val Lys
        340                 345                 350

Asp Asp Glu Gly Ile Leu Arg Gln Asp Arg Tyr Pro Leu Arg Thr Ser
    355                 360                 365

Pro Gln Trp Leu Gly Pro Leu Val Ser Asp Leu Ile His Ala His Ala
370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
            405                 410                 415

Ala Val Ala Asn Thr Met Glu Lys Thr Arg Leu Gly Leu Ala Gln Ile
        420                 425                 430

Gly Lys Leu Asn Phe Thr Gln Leu Thr Glu Met Leu Asn Ala Gly Met
    435                 440                 445

Asn Arg Gly Leu Pro Ser Cys Leu Ala Ala Glu Asp Pro Ser Leu Ser
450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
            485                 490                 495

Met Ala Asn Gln Ala Val Asn Ser Leu Ala Leu Ile Ser Ala Arg Arg
        500                 505                 510

Thr Thr Glu Ser Asn Asp Val Leu Ser Leu Leu Leu Ala Thr His Leu
    515                 520                 525

Tyr Cys Val Leu Gln Ala Ile Asp Leu Arg Ala Ile Glu Phe Glu Phe
530                 535                 540

Lys Lys Gln Phe Gly Pro Ala Ile Val Ser Leu Ile Asp Gln His Phe
545                 550                 555                 560

```
Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715

<210> SEQ ID NO 5
<211> LENGTH: 505
<212> TYPE: PRT
<213> ORGANISM: Arabidopsis thaliana

<400> SEQUENCE: 5

Met Asp Leu Leu Leu Glu Lys Ser Leu Ile Ala Val Phe Val Ala
1               5                   10                  15

Val Ile Leu Ala Thr Val Ile Ser Lys Leu Arg Gly Lys Lys Leu Lys
            20                  25                  30

Leu Pro Pro Gly Pro Ile Pro Ile Pro Ile Phe Gly Asn Trp Leu Gln
        35                  40                  45

Val Gly Asp Asp Leu Asn His Arg Asn Leu Val Asp Tyr Ala Lys Lys
    50                  55                  60

Phe Gly Asp Leu Phe Leu Leu Arg Met Gly Gln Arg Asn Leu Val Val
65                  70                  75                  80

Val Ser Ser Pro Asp Leu Thr Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Asn Arg Glu Gly Trp Glu Phe Glu Ala Ala Ser Val Val Glu Asp
145                 150                 155                 160

Val Lys Lys Asn Pro Asp Ser Ala Thr Lys Gly Ile Val Leu Arg Lys
                165                 170                 175

Arg Leu Gln Leu Met Met Tyr Asn Asn Met Phe Arg Ile Met Phe Asp
            180                 185                 190

Arg Arg Phe Glu Ser Glu Asp Ser Pro Leu Phe Leu Arg Leu Lys Ala
        195                 200                 205

Leu Asn Gly Glu Arg Ser Arg Leu Ala Gln Ser Phe Glu Tyr Asn Tyr
    210                 215                 220
```

```
Gly Asp Phe Ile Pro Ile Leu Arg Pro Phe Leu Arg Gly Tyr Leu Lys
225                 230                 235                 240

Ile Cys Gln Asp Val Lys Asp Arg Arg Ile Ala Leu Phe Lys Lys Tyr
            245                 250                 255

Phe Val Asp Glu Arg Lys Gln Ile Ala Ser Ser Lys Pro Thr Gly Ser
        260                 265                 270

Glu Gly Leu Lys Cys Ala Ile Asp His Ile Leu Glu Ala Glu Gln Lys
    275                 280                 285

Gly Glu Ile Asn Glu Asp Asn Val Leu Tyr Ile Val Glu Asn Ile Asn
290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Ser Lys Leu Arg Asn Glu Leu
            325                 330                 335

Asp Thr Val Leu Gly Pro Gly Val Gln Val Thr Glu Pro Asp Leu His
        340                 345                 350

Lys Leu Pro Tyr Leu Gln Ala Val Val Lys Glu Thr Leu Arg Leu Arg
    355                 360                 365

Met Ala Ile Pro Leu Leu Val Pro His Met Asn Leu His Asp Ala Lys
370                 375                 380

Leu Ala Gly Tyr Asp Ile Pro Ala Glu Ser Lys Ile Leu Val Asn Ala
385                 390                 395                 400

Trp Trp Leu Ala Asn Asn Pro Asn Ser Trp Lys Lys Pro Glu Glu Phe
            405                 410                 415

Arg Pro Glu Arg Phe Phe Glu Glu Ser His Val Gly Ala Asn Gly
        420                 425                 430

Asn Asp Phe Arg Tyr Val Pro Phe Gly Val Gly Arg Arg Ser Cys Pro
    435                 440                 445

Gly Ile Ile Leu Ala Leu Pro Ile Leu Gly Ile Thr Ile Gly Arg Met
450                 455                 460

Val Gln Asn Phe Glu Leu Leu Pro Pro Gly Gln Ser Lys Val Asp
465                 470                 475                 480

Thr Ser Glu Lys Gly Gly Gln Phe Ser Leu His Ile Leu Asn His Ser
            485                 490                 495

Ile Ile Val Met Lys Pro Arg Asn Cys
            500                 505

<210> SEQ ID NO 6
<211> LENGTH: 716
<212> TYPE: PRT
<213> ORGANISM: Rhodosporidium toruloides

<400> SEQUENCE: 6

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
            85                  90                  95
```

```
Ser Val Glu Phe Leu Arg Ser Gln Leu Ser Met Ser Val Tyr Gly Val
            100                 105                 110
Thr Thr Gly Phe Gly Gly Ser Ala Asp Thr Arg Thr Glu Asp Ala Ile
        115                 120                 125
Ser Leu Gln Lys Ala Leu Leu Glu His Gln Leu Cys Gly Val Leu Pro
    130                 135                 140
Ser Ser Phe Asp Ser Phe Arg Leu Gly Arg Gly Leu Glu Asn Ser Leu
145                 150                 155                 160
Pro Leu Glu Val Val Arg Gly Ala Met Thr Ile Arg Val Asn Ser Leu
                165                 170                 175
Thr Arg Gly His Ser Ala Val Arg Leu Val Leu Glu Ala Leu Thr
            180                 185                 190
Asn Phe Leu Asn His Gly Ile Thr Pro Ile Val Pro Leu Arg Gly Thr
        195                 200                 205
Ile Ser Ala Ser Gly Asp Leu Ser Pro Leu Ser Tyr Ile Ala Ala Ala
    210                 215                 220
Ile Ser Gly His Pro Asp Ser Lys Val His Val His Glu Gly Lys
225                 230                 235                 240
Glu Lys Ile Leu Tyr Ala Arg Glu Ala Met Ala Leu Phe Asn Leu Glu
                245                 250                 255
Pro Val Val Leu Gly Pro Lys Glu Gly Leu Gly Leu Val Asn Gly Thr
            260                 265                 270
Ala Val Ser Ala Ser Met Ala Thr Leu Ala Leu His Asp Ala His Met
        275                 280                 285
Leu Ser Leu Leu Ser Gln Ser Leu Thr Ala Met Thr Val Glu Ala Met
    290                 295                 300
Val Gly His Ala Gly Ser Phe His Pro Phe Leu His Asp Val Thr Arg
305                 310                 315                 320
Pro His Pro Thr Gln Ile Glu Val Ala Gly Asn Ile Arg Lys Leu Leu
                325                 330                 335
Glu Gly Ser Arg Phe Ala Val His His Glu Glu Val Lys Val Lys
            340                 345                 350
Asp Asp Glu Gly Ile Leu Arg Gln Asp Arg Tyr Pro Leu Arg Thr Ser
        355                 360                 365
Pro Gln Trp Leu Gly Pro Leu Val Ser Asp Leu Ile His Ala His Ala
    370                 375                 380
Val Leu Thr Ile Glu Ala Gly Gln Ser Thr Thr Asp Asn Pro Leu Ile
385                 390                 395                 400
Asp Val Glu Asn Lys Thr Ser His His Gly Gly Asn Phe Gln Ala Ala
                405                 410                 415
Ala Val Ala Asn Thr Met Glu Lys Thr Arg Leu Gly Leu Ala Gln Ile
            420                 425                 430
Gly Lys Leu Asn Phe Thr Gln Leu Thr Glu Met Leu Asn Ala Gly Met
        435                 440                 445
Asn Arg Gly Leu Pro Ser Cys Leu Ala Ala Glu Asp Pro Ser Leu Ser
    450                 455                 460
Tyr His Cys Lys Gly Leu Asp Ile Ala Ala Ala Tyr Thr Ser Glu
465                 470                 475                 480
Leu Gly His Leu Ala Asn Pro Val Thr Thr His Val Gln Pro Ala Glu
                485                 490                 495
Met Ala Asn Gln Ala Val Asn Ser Leu Ala Leu Ile Ser Ala Arg Arg
            500                 505                 510
```

```
Thr Thr Glu Ser Asn Asp Val Leu Ser Leu Leu Ala Thr His Leu
        515                 520                 525

Tyr Cys Val Leu Gln Ala Ile Asp Leu Arg Ala Ile Glu Phe Glu Phe
530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
                580                 585                 590

Leu Val Pro Arg Trp His Asp Ala Phe Ser Phe Ala Ala Gly Thr Val
            595                 600                 605

Val Glu Val Leu Ser Ser Thr Ser Leu Ser Leu Ala Ala Val Asn Ala
        610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
                660                 665                 670

Leu Gly Val Lys Ala Arg Arg Gly Asp Val Phe Leu Gly Lys Gln Glu
            675                 680                 685

Val Thr Ile Gly Ser Asn Val Ser Lys Ile Tyr Glu Ala Ile Lys Ser
        690                 695                 700

Gly Arg Ile Asn Asn Val Leu Leu Lys Met Leu Ala
705                 710                 715

<210> SEQ ID NO 7
<211> LENGTH: 508
<212> TYPE: PRT
<213> ORGANISM: Arabidopsis thaliana

<400> SEQUENCE: 7

Met Ser Trp Phe Leu Ile Ala Val Ala Thr Ile Ala Ala Val Val Ser
1               5                   10                  15

Tyr Lys Leu Ile Gln Arg Leu Arg Tyr Lys Phe Pro Pro Gly Pro Ser
                20                  25                  30

Pro Lys Pro Ile Val Gly Asn Leu Tyr Asp Ile Lys Pro Val Arg Phe
            35                  40                  45

Arg Cys Tyr Tyr Glu Trp Ala Gln Ser Tyr Gly Pro Ile Ile Ser Val
50                  55                  60

Trp Ile Gly Ser Ile Leu Asn Val Val Ser Ser Ala Glu Leu Ala
65                  70                  75                  80

Lys Glu Val Leu Lys Glu His Asp Gln Lys Leu Ala Asp Arg His Arg
                85                  90                  95

Asn Arg Ser Thr Glu Ala Phe Ser Arg Asn Gly Gln Asp Leu Ile Trp
            100                 105                 110

Ala Asp Tyr Gly Pro His Tyr Val Lys Val Arg Lys Val Cys Thr Leu
        115                 120                 125

Glu Leu Phe Thr Pro Lys Arg Leu Glu Ser Leu Arg Pro Ile Arg Glu
    130                 135                 140

Asp Glu Val Thr Ala Met Val Glu Ser Val Phe Arg Asp Cys Asn Leu
145                 150                 155                 160

Pro Glu Asn Arg Ala Lys Gly Leu Gln Leu Arg Lys Tyr Leu Gly Ala
                165                 170                 175
```

```
Val Ala Phe Asn Asn Ile Thr Arg Leu Ala Phe Gly Lys Arg Phe Met
            180                 185                 190

Asn Ala Glu Gly Val Val Asp Glu Gln Gly Leu Glu Phe Lys Ala Ile
        195                 200                 205

Val Ser Asn Gly Leu Lys Leu Gly Ala Ser Leu Ser Ile Ala Glu His
    210                 215                 220

Ile Pro Trp Leu Arg Trp Met Phe Pro Ala Asp Glu Lys Ala Phe Ala
225                 230                 235                 240

Glu His Gly Ala Arg Arg Asp Arg Leu Thr Arg Ala Ile Met Glu Glu
                245                 250                 255

His Thr Leu Ala Arg Gln Lys Ser Ser Gly Ala Lys Gln His Phe Val
            260                 265                 270

Asp Ala Leu Leu Thr Leu Lys Asp Gln Tyr Asp Leu Ser Glu Asp Thr
        275                 280                 285

Ile Ile Gly Leu Leu Trp Asp Met Ile Thr Ala Gly Met Asp Thr Thr
    290                 295                 300

Ala Ile Thr Ala Glu Trp Ala Met Ala Glu Met Ile Lys Asn Pro Arg
305                 310                 315                 320

Val Gln Gln Lys Val Gln Glu Glu Phe Asp Arg Val Val Gly Leu Asp
                325                 330                 335

Arg Ile Leu Thr Glu Ala Asp Phe Ser Arg Leu Pro Tyr Leu Gln Cys
            340                 345                 350

Val Val Lys Glu Ser Phe Arg Leu His Pro Pro Thr Pro Leu Met Leu
        355                 360                 365

Pro His Arg Ser Asn Ala Asp Val Lys Ile Gly Gly Tyr Asp Ile Pro
    370                 375                 380

Lys Gly Ser Asn Val His Val Asn Val Trp Ala Val Ala Arg Asp Pro
385                 390                 395                 400

Ala Val Trp Lys Asn Pro Phe Glu Phe Arg Pro Glu Arg Phe Leu Glu
                405                 410                 415

Glu Asp Val Asp Met Lys Gly His Asp Phe Arg Leu Leu Pro Phe Gly
            420                 425                 430

Ala Gly Arg Arg Val Cys Pro Gly Ala Gln Leu Gly Ile Asn Leu Val
        435                 440                 445

Thr Ser Met Met Ser His Leu Leu His His Phe Val Trp Thr Pro Pro
    450                 455                 460

Gln Gly Thr Lys Pro Glu Glu Ile Asp Met Ser Glu Asn Pro Gly Leu
465                 470                 475                 480

Val Thr Tyr Met Arg Thr Pro Val Gln Ala Val Ala Thr Pro Arg Leu
                485                 490                 495

Pro Ser Asp Leu Tyr Lys Arg Val Pro Tyr Asp Met
            500                 505
```

<210> SEQ ID NO 8
<211> LENGTH: 497
<212> TYPE: PRT
<213> ORGANISM: Arabidopsis thaliana

<400> SEQUENCE: 8

```
Met Ile Ile Tyr Leu Ile Ser Leu Leu Pro Ile Ile Val Ala Thr Leu
1               5                   10                  15

Met Leu Tyr Gln Arg Trp Trp Arg Ser Asn Ile Pro Pro Gly Pro Lys
            20                  25                  30

Pro Lys Phe Leu Leu Gly Asn Leu His Gln Met Lys Pro Leu Trp Thr
        35                  40                  45
```

```
His Ser Phe Ser Glu Trp Ser Glu Thr Tyr Gly Pro Ile Ile Ser Val
 50                  55                  60

Trp Ile Gly Ser Gln Leu Thr Val Val Ser Ser Asp Leu Ala
 65                  70                  75                  80

Arg Gln Val Leu Arg Asp Lys Asp His Gln Leu Ser Asn Arg His Arg
                     85                  90                  95

Ile Ala Arg Met Thr Gln Thr Gly Thr Asp Leu Val Trp Ser Asp Tyr
                100                 105                 110

Ser Pro His Tyr Val Lys Leu Arg Lys Leu Cys Thr Leu Glu Leu Phe
                115                 120                 125

Ser Leu Lys Ser Ile Glu Asn Phe Arg Ser Leu Arg Glu Met Glu Ala
130                 135                 140

Arg Ser Met Val Val Ser Ile Leu Lys Asp Leu Met Ser Asn Ser Gly
145                 150                 155                 160

Asp Asp Gln Glu Arg Lys Pro Val Ile Val Arg Lys Tyr Leu Ala Ala
                165                 170                 175

Val Val Leu Asn Thr Ile Ser Arg Leu Met Ile Gly Lys Glu Phe Gly
                180                 185                 190

Ser Glu Glu Gly Lys Glu Phe Lys Ala Ile Val Glu Lys Glu His Leu
                195                 200                 205

Leu Ser Gly Ser Gly Thr Ile Leu Asp His Val Trp Trp Leu Lys Trp
210                 215                 220

Val Ser Ser Trp Phe Phe Ser Asp Lys Glu Phe Leu Ala His Lys Asp
225                 230                 235                 240

Arg Arg Thr Lys Trp Phe Arg Gly Ala Ile Met Val Glu Glu Asp Ile
                245                 250                 255

Glu Ile Glu Asp His Arg Gly Phe Val Arg Lys Leu Leu Val Leu Lys
                260                 265                 270

Glu Gln Lys Glu Leu Ser Glu Glu Thr Val Gly Gly Leu Val Trp Asn
                275                 280                 285

Met Leu Thr Ala Gly Ala Asp Thr Thr Ala Val Val Ile Glu Trp Ala
290                 295                 300

Met Ala Glu Met Ile Lys Cys Pro Thr Val Gln Glu Lys Ala Gln Gln
305                 310                 315                 320

Glu Leu Asp Ser Val Val Gly Ser Glu Arg Leu Met Thr Glu Ser Asp
                325                 330                 335

Ile Pro Ile Leu Pro Tyr Leu Gln Cys Val Val Lys Glu Ala Leu Arg
                340                 345                 350

Leu His Pro Ser Thr Pro Leu Met Leu Pro His Lys Ala Ser Glu Thr
                355                 360                 365

Val Trp Val Gly Gly Tyr Lys Val Pro Lys Gly Ala Thr Val Tyr Val
                370                 375                 380

Asn Val Gln Ala Ile Gly Arg Asp Pro Ala Asn Trp Ile Asn Pro Tyr
385                 390                 395                 400

Glu Phe Arg Pro Glu Arg Phe Leu Gln Glu Glu Thr Asp Val Lys Gly
                405                 410                 415

Arg Asp Phe Arg Val Leu Pro Phe Gly Ser Gly Arg Arg Met Cys Pro
                420                 425                 430

Ala Ala Gln Leu Ser Met Asn Leu Met Thr Leu Val Met Gly Asn Leu
                435                 440                 445

Leu His Cys Phe Ser Trp Ser Ser Pro Val Pro Gly Glu Arg Ile Asp
450                 455                 460
```

```
Met Ser Glu Asn Pro Gly Leu Leu Cys Asn Met Arg Thr Pro Leu Gln
465                 470                 475                 480

Ala Leu Ala Leu Pro Arg Ala Ala Arg Ala Ile Pro Leu Pro Leu
            485                 490                 495

Asp

<210> SEQ ID NO 9
<211> LENGTH: 487
<212> TYPE: PRT
<213> ORGANISM: Arabidopsis thaliana

<400> SEQUENCE: 9

Met Asp Leu Leu Leu Ile Ser Leu Thr Thr Ile Ile Ile Ala Ala Tyr
1               5                   10                  15

Met Gln Asn Leu Arg Arg Arg Gly Ser Asn Ile Pro Gly Pro Pro
            20                  25                  30

Thr Arg Phe Leu Val Gly Asn Leu His Gln Leu Lys Pro Leu Trp Thr
            35                  40                  45

Gln Ser Phe Ser Glu Trp Ser Gln Thr Tyr Gly Pro Ile Ile Ser Val
    50                  55                  60

Trp Leu Gly Ser Gln Leu Ala Val Val Val Ser Ser Asp Leu Ala
65                  70                  75                  80

Lys Gln Val Leu Arg Asp Lys Asp Tyr Gln Leu Cys Asn Arg His Arg
                85                  90                  95

Thr Ala Arg Met Thr Gln Asn Gly Ser Asp Leu Ile Trp Ser Asp Tyr
                100                 105                 110

Gly Ala His Tyr Val Lys Met Arg Lys Leu Cys Thr Leu Glu Leu Phe
            115                 120                 125

Ser Leu Lys Ser Ile Glu Cys Phe Arg Ser Met Arg Glu Met Glu Val
130                 135                 140

Ser Ser Met Val Lys Ser Ile Phe Asn Asp Phe Met Ser Asp Asp Gln
145                 150                 155                 160

Lys Pro Val Val Leu Arg Asn Tyr Leu Asp Ser Val Ala Leu Asn Ile
                165                 170                 175

Val Ser Arg Leu Val Ile Gly Lys Thr Phe Glu Pro Lys Asp Gly Arg
            180                 185                 190

Glu Phe Arg Ser Ile Val Glu Arg Glu Thr Arg Leu Pro Gly Ala Thr
        195                 200                 205

Lys Met Leu Asp Tyr Thr Val Trp Leu Lys Arg Leu Ser Ser Trp Phe
210                 215                 220

Thr Ser Asp Lys Ala Phe Met Lys His Met Ala Arg Lys Arg Asn Trp
225                 230                 235                 240

Phe Lys Arg Ala Val Met Asp Glu Val Tyr Gly Gly Arg Asp Gln Lys
                245                 250                 255

Cys Phe Val Gln Ser Leu Leu Gly Leu Lys Glu Lys Asp Glu Leu Thr
            260                 265                 270

Glu Glu Thr Val Met Gly Leu Val Trp Asn Met Leu Thr Ala Gly Ala
        275                 280                 285

Asp Thr Thr Ala Ile Thr Ile Glu Trp Ala Met Ala Glu Met Ile Arg
290                 295                 300

Cys Pro Thr Val Lys Glu Lys Val Gln Asp Glu Leu Asp Ser Val Val
305                 310                 315                 320

Gly Ser Gly Arg Leu Met Ser Asp Ala Asp Ile Pro Lys Leu Pro Phe
                325                 330                 335
```

```
Leu Gln Cys Val Leu Lys Glu Ala Leu Arg Leu His Pro Pro Thr Pro
                340                 345                 350

Leu Met Leu Pro His Lys Ala Ser Glu Ser Val Gln Val Gly Gly Tyr
            355                 360                 365

Lys Val Pro Lys Gly Ala Thr Val Tyr Val Asn Val Gln Ala Ile Ala
        370                 375                 380

Arg Asp Pro Ala Asn Trp Ser Asn Pro Asp Glu Phe Arg Pro Glu Arg
385                 390                 395                 400

Phe Leu Val Glu Glu Thr Asp Val Lys Gly Gln Asp Phe Arg Val Leu
                405                 410                 415

Pro Phe Gly Ser Gly Arg Arg Val Cys Pro Ala Ala Gln Leu Ser Leu
            420                 425                 430

Asn Met Met Thr Leu Ala Leu Gly Ser Leu Leu His Cys Phe Ser Trp
        435                 440                 445

Thr Ser Ser Thr Pro Arg Glu His Ile Asp Met Thr Glu Lys Pro Gly
    450                 455                 460

Leu Val Cys Tyr Met Lys Ala Pro Leu Gln Ala Leu Ala Ser Ser Arg
465                 470                 475                 480

Leu Pro Gln Glu Leu Tyr Leu
                485

<210> SEQ ID NO 10
<211> LENGTH: 561
<212> TYPE: PRT
<213> ORGANISM: Arabidopsis thaliana

<400> SEQUENCE: 10

Met Ile Thr Ala Ala Leu His Glu Pro Gln Ile His Lys Pro Thr Asp
1               5                   10                  15

Thr Ser Val Val Ser Asp Val Leu Pro His Ser Pro Pro Thr Pro
            20                  25                  30

Arg Ile Phe Arg Ser Lys Leu Pro Asp Ile Asp Ile Pro Asn His Leu
        35                  40                  45

Pro Leu His Thr Tyr Cys Phe Glu Lys Leu Ser Ser Val Ser Asp Lys
    50                  55                  60

Pro Cys Leu Ile Val Gly Ser Thr Gly Lys Ser Tyr Thr Tyr Gly Glu
65                  70                  75                  80

Thr His Leu Ile Cys Arg Arg Val Ala Ser Gly Leu Tyr Lys Leu Gly
                85                  90                  95

Ile Arg Lys Gly Asp Val Ile Met Ile Leu Leu Gln Asn Ser Ala Glu
            100                 105                 110

Phe Val Phe Ser Phe Met Gly Ala Ser Met Ile Gly Ala Val Ser Thr
        115                 120                 125

Thr Ala Asn Pro Phe Tyr Thr Ser Gln Glu Leu Tyr Lys Gln Leu Lys
    130                 135                 140

Ser Ser Gly Ala Lys Leu Ile Ile Thr His Ser Gln Tyr Val Asp Lys
145                 150                 155                 160

Leu Lys Asn Leu Gly Glu Asn Leu Thr Leu Ile Thr Thr Asp Glu Pro
                165                 170                 175

Thr Pro Glu Asn Cys Leu Pro Phe Ser Thr Leu Ile Thr Asp Asp Glu
            180                 185                 190

Thr Asn Pro Phe Gln Glu Thr Val Asp Ile Gly Gly Asp Asp Ala Ala
        195                 200                 205

Ala Leu Pro Phe Ser Ser Gly Thr Thr Gly Leu Pro Lys Gly Val Val
    210                 215                 220
```

```
Leu Thr His Lys Ser Leu Ile Thr Ser Val Ala Gln Gln Val Asp Gly
225                 230                 235                 240

Asp Asn Pro Asn Leu Tyr Leu Lys Ser Asn Asp Val Ile Leu Cys Val
            245                 250                 255

Leu Pro Leu Phe His Ile Tyr Ser Leu Asn Ser Val Leu Leu Asn Ser
        260                 265                 270

Leu Arg Ser Gly Ala Thr Val Leu Leu Met His Lys Phe Glu Ile Gly
    275                 280                 285

Ala Leu Leu Asp Leu Ile Gln Arg His Arg Val Thr Ile Ala Ala Leu
290                 295                 300

Val Pro Pro Leu Val Ile Ala Leu Ala Lys Asn Pro Thr Val Asn Ser
305                 310                 315                 320

Tyr Asp Leu Ser Ser Val Arg Phe Val Leu Ser Gly Ala Ala Pro Leu
                325                 330                 335

Gly Lys Glu Leu Gln Asp Ser Leu Arg Arg Arg Leu Pro Gln Ala Ile
            340                 345                 350

Leu Gly Gln Gly Tyr Gly Met Thr Glu Ala Gly Pro Val Leu Ser Met
        355                 360                 365

Ser Leu Gly Phe Ala Lys Glu Pro Ile Pro Thr Lys Ser Gly Ser Cys
    370                 375                 380

Gly Thr Val Val Arg Asn Ala Glu Leu Lys Val Val His Leu Glu Thr
385                 390                 395                 400

Arg Leu Ser Leu Gly Tyr Asn Gln Pro Gly Glu Ile Cys Ile Arg Gly
                405                 410                 415

Gln Gln Ile Met Lys Glu Tyr Leu Asn Asp Pro Glu Ala Thr Ser Ala
            420                 425                 430

Thr Ile Asp Glu Glu Gly Trp Leu His Thr Gly Asp Ile Gly Tyr Val
        435                 440                 445

Asp Glu Asp Asp Glu Ile Phe Ile Val Asp Arg Leu Lys Glu Val Ile
    450                 455                 460

Lys Phe Lys Gly Phe Gln Val Pro Pro Ala Glu Leu Glu Ser Leu Leu
465                 470                 475                 480

Ile Asn His His Ser Ile Ala Asp Ala Ala Val Val Pro Gln Asn Asp
                485                 490                 495

Glu Val Ala Gly Glu Val Pro Val Ala Phe Val Val Arg Ser Asn Gly
            500                 505                 510

Asn Asp Ile Thr Glu Glu Asp Val Lys Glu Tyr Val Ala Lys Gln Val
        515                 520                 525

Val Phe Tyr Lys Arg Leu His Lys Val Phe Phe Val Ala Ser Ile Pro
    530                 535                 540

Lys Ser Pro Ser Gly Lys Ile Leu Arg Lys Asp Leu Lys Ala Lys Leu
545                 550                 555                 560

Cys

<210> SEQ ID NO 11
<211> LENGTH: 547
<212> TYPE: PRT
<213> ORGANISM: Nicotiana tabacum

<400> SEQUENCE: 11

Met Pro Met Glu Thr Thr Glu Thr Lys Gln Ser Gly Asp Leu Ile
1               5                   10                  15

Phe Arg Ser Lys Leu Pro Asp Ile Tyr Ile Pro Lys His Leu Pro Leu
            20                  25                  30
```

```
His Ser Tyr Cys Phe Glu Asn Ile Ser Glu Phe Ser Ser Arg Pro Cys
         35                  40                  45

Leu Ile Asn Gly Ala Asn Asp Gln Ile Tyr Thr Tyr Ala Glu Val Glu
 50                  55                  60

Leu Thr Cys Arg Lys Val Ala Val Gly Leu Asn Lys Leu Gly Ile Gln
 65                  70                  75                  80

Gln Lys Asp Thr Ile Met Ile Leu Leu Pro Asn Ser Pro Glu Phe Val
                 85                  90                  95

Phe Ala Phe Met Gly Ala Ser Tyr Leu Gly Ala Ile Ser Thr Met Ala
            100                 105                 110

Asn Pro Leu Phe Thr Pro Ala Glu Val Val Lys Gln Ala Lys Ala Ser
            115                 120                 125

Ser Ala Lys Ile Ile Ile Thr Gln Ser Cys Phe Val Gly Lys Val Lys
130                 135                 140

Asp Tyr Ala Ser Glu Asn Asp Val Lys Val Ile Cys Ile Asp Ser Ala
145                 150                 155                 160

Pro Glu Gly Cys Leu His Phe Ser Glu Leu Thr Gln Ser Asp Glu His
                165                 170                 175

Glu Ile Pro Glu Val Lys Ile Gln Pro Asp Asp Val Val Ala Leu Pro
            180                 185                 190

Tyr Ser Ser Gly Thr Thr Gly Leu Pro Lys Gly Val Met Leu Thr His
            195                 200                 205

Lys Gly Leu Val Thr Ser Val Ala Gln Gln Val Asp Gly Glu Asn Ala
210                 215                 220

Asn Leu Tyr Met His Ser Glu Asp Val Leu Met Cys Val Leu Pro Leu
225                 230                 235                 240

Phe His Ile Tyr Ser Leu Asn Ser Ile Leu Leu Cys Gly Leu Arg Val
                245                 250                 255

Gly Ala Ala Ile Leu Ile Met Gln Lys Phe Asp Ile Ala Pro Phe Leu
            260                 265                 270

Glu Leu Ile Gln Lys Tyr Lys Val Ser Ile Gly Pro Phe Val Pro Pro
            275                 280                 285

Ile Val Leu Ala Ile Ala Lys Ser Pro Ile Val Asp Ser Tyr Asp Leu
            290                 295                 300

Ser Ser Val Arg Thr Val Met Ser Gly Ala Ala Pro Leu Gly Lys Glu
305                 310                 315                 320

Leu Glu Asp Ala Val Arg Thr Lys Phe Pro Asn Ala Lys Leu Gly Gln
                325                 330                 335

Gly Tyr Gly Met Thr Glu Ala Gly Pro Val Leu Ala Met Cys Leu Ala
            340                 345                 350

Phe Ala Lys Glu Pro Phe Asp Ile Lys Ser Gly Ala Cys Gly Thr Val
            355                 360                 365

Val Arg Asn Ala Glu Met Lys Ile Val Asp Pro Asp Thr Gly Cys Ser
370                 375                 380

Leu Pro Arg Asn Gln Pro Gly Glu Ile Cys Ile Arg Gly Asp Gln Ile
385                 390                 395                 400

Met Lys Gly Tyr Leu Asn Asp Pro Glu Ala Thr Thr Arg Thr Ile Asp
                405                 410                 415

Lys Glu Gly Trp Leu His Thr Gly Asp Ile Gly Phe Ile Asp Glu Asp
            420                 425                 430

Asp Glu Leu Phe Ile Val Asp Arg Leu Lys Glu Leu Ile Lys Tyr Lys
            435                 440                 445
```

```
Gly Phe Gln Val Ala Pro Ala Glu Ile Glu Ala Leu Leu Asn His
450                 455                 460

Pro Asn Ile Ser Asp Ala Ala Val Val Pro Met Lys Asp Gln Ala
465                 470                 475                 480

Gly Glu Val Pro Val Ala Phe Val Val Arg Ser Asn Gly Ser Ala Ile
                485                 490                 495

Thr Glu Asp Glu Val Lys Asp Phe Ile Ser Lys Gln Val Ile Phe Tyr
                500                 505                 510

Lys Arg Val Lys Arg Val Phe Phe Val Glu Thr Val Pro Lys Ser Pro
                515                 520                 525

Ser Gly Lys Ile Leu Arg Lys Asp Leu Arg Ala Arg Leu Ala Ala Gly
                530                 535                 540

Val Pro Asn
545

<210> SEQ ID NO 12
<211> LENGTH: 435
<212> TYPE: PRT
<213> ORGANISM: Nicotiana tabacum

<400> SEQUENCE: 12

Met Lys Ile Glu Val Lys Glu Ser Thr Met Val Lys Pro Ala Ala Glu
1               5                   10                  15

Thr Pro Gln Gln Arg Leu Trp Asn Ser Asn Val Asp Leu Val Val Pro
                20                  25                  30

Asn Phe His Thr Pro Ser Val Tyr Phe Tyr Arg Pro Thr Gly Ser Pro
                35                  40                  45

Asn Phe Phe Asp Gly Lys Val Leu Lys Glu Ala Leu Ser Lys Ala Leu
50                  55                  60

Val Pro Phe Tyr Pro Met Ala Gly Arg Leu Cys Arg Asp Glu Asp Gly
65                  70                  75                  80

Arg Ile Glu Ile Asp Cys Lys Gly Gln Gly Val Leu Phe Val Glu Ala
                85                  90                  95

Glu Ser Asp Gly Val Val Asp Asp Phe Gly Asp Phe Ala Pro Thr Leu
                100                 105                 110

Glu Leu Arg Gln Leu Ile Pro Ala Val Asp Tyr Ser Gln Gly Ile Gln
                115                 120                 125

Ser Tyr Ala Leu Leu Val Leu Gln Ile Thr His Phe Lys Cys Gly Gly
                130                 135                 140

Val Ser Leu Gly Val Gly Met Gln His His Ala Ala Asp Gly Ala Ser
145                 150                 155                 160

Gly Leu His Phe Ile Asn Thr Trp Ser Asp Met Ala Arg Gly Leu Asp
                165                 170                 175

Leu Thr Ile Pro Pro Phe Ile Asp Arg Thr Leu Leu Arg Ala Arg Asp
                180                 185                 190

Pro Pro Gln Pro Gln Phe Pro His Val Glu Tyr Gln Pro Pro Pro Thr
                195                 200                 205

Leu Lys Val Thr Pro Glu Asn Thr Pro Ile Ser Glu Ala Val Pro Glu
                210                 215                 220

Thr Ser Val Ser Ile Phe Lys Leu Thr Arg Asp Gln Ile Asn Thr Leu
225                 230                 235                 240

Lys Ala Lys Ser Lys Glu Asp Gly Asn Thr Val Asn Tyr Ser Ser Tyr
                245                 250                 255

Glu Met Leu Ala Gly His Val Trp Arg Ser Thr Cys Met Ala Arg Gly
                260                 265                 270
```

```
Leu Ala His Asp Gln Glu Thr Lys Leu Tyr Ile Ala Thr Asp Gly Arg
            275                 280                 285

Ser Arg Leu Arg Pro Ser Leu Pro Pro Gly Tyr Phe Gly Asn Val Ile
        290                 295                 300

Phe Thr Thr Thr Pro Ile Ala Val Ala Gly Asp Ile Gln Ser Lys Pro
305                 310                 315                 320

Ile Trp Tyr Ala Ala Ser Lys Leu His Asp Ala Leu Ala Arg Met Asp
                325                 330                 335

Asn Asp Tyr Leu Arg Ser Ala Leu Asp Tyr Leu Glu Leu Gln Pro Asp
            340                 345                 350

Leu Lys Ala Leu Val Arg Gly Ala His Thr Phe Lys Cys Pro Asn Leu
        355                 360                 365

Gly Ile Thr Ser Trp Ser Arg Leu Pro Ile His Asp Ala Asp Phe Gly
370                 375                 380

Trp Gly Arg Pro Ile Phe Met Gly Pro Gly Gly Ile Ala Tyr Glu Gly
385                 390                 395                 400

Leu Ser Phe Ile Leu Pro Ser Pro Thr Asn Asp Gly Ser Gln Ser Val
                405                 410                 415

Ala Ile Ser Leu Gln Ala Glu His Met Lys Leu Phe Glu Lys Phe Leu
            420                 425                 430

Tyr Asp Phe
        435

<210> SEQ ID NO 13
<211> LENGTH: 434
<212> TYPE: PRT
<213> ORGANISM: Coffea arabica

<400> SEQUENCE: 13

Met Lys Ile Glu Val Lys Glu Ser Thr Met Val Arg Pro Ala Gln Glu
1               5                   10                  15

Thr Pro Arg Arg Asn Leu Trp Asn Ser Asn Val Asp Leu Val Val Pro
            20                  25                  30

Asn Phe His Thr Pro Ser Val Tyr Phe Tyr Arg Pro Thr Gly Ser Ser
        35                  40                  45

Asn Phe Phe Asp Ala Lys Val Leu Lys Asp Ala Leu Ser Arg Ala Leu
50                  55                  60

Val Pro Phe Tyr Pro Met Ala Gly Arg Leu Lys Arg Asp Glu Asp Gly
65                  70                  75                  80

Arg Ile Glu Ile Glu Cys Asn Gly Glu Gly Val Leu Phe Val Glu Ala
                85                  90                  95

Glu Ser Asp Gly Val Val Asp Asp Phe Gly Asp Phe Ala Pro Thr Leu
            100                 105                 110

Glu Leu Arg Arg Leu Ile Pro Ala Val Asp Tyr Ser Gln Gly Ile Ser
        115                 120                 125

Ser Tyr Ala Leu Leu Val Leu Gln Val Thr Tyr Phe Lys Cys Gly Gly
130                 135                 140

Val Ser Leu Gly Val Gly Met Gln His Ala Ala Asp Gly Phe Ser
145                 150                 155                 160

Gly Leu His Phe Ile Asn Ser Trp Ser Asp Met Ala Arg Gly Leu Asp
                165                 170                 175

Val Thr Leu Pro Pro Phe Ile Asp Arg Thr Leu Leu Arg Ala Arg Asp
            180                 185                 190
```

Pro Pro Gln Pro Gln Phe Gln His Ile Glu Tyr Gln Pro Pro Thr
            195                 200                 205

Leu Lys Val Ser Pro Gln Thr Ala Lys Ser Asp Ser Val Pro Glu Thr
210                 215                 220

Ala Val Ser Ile Phe Lys Leu Thr Arg Glu Gln Ile Ser Ala Leu Lys
225                 230                 235                 240

Ala Lys Pro Lys Glu Asp Gly Asn Thr Ile Ser Tyr Ser Ser Tyr Glu
            245                 250                 255

Met Leu Ala Gly His Val Trp Arg Cys Ala Cys Lys Ala Arg Gly Leu
            260                 265                 270

Glu Val Asp Gln Gly Thr Lys Leu Tyr Ile Ala Thr Asp Gly Arg Ala
            275                 280                 285

Arg Leu Arg Pro Ser Leu Pro Pro Gly Tyr Phe Gly Asn Val Ile Phe
290                 295                 300

Thr Ala Thr Pro Ile Ala Ile Ala Gly Asp Leu Glu Phe Lys Pro Val
305                 310                 315                 320

Trp Tyr Ala Ala Ser Lys Ile His Asp Ala Leu Ala Arg Met Asp Asn
            325                 330                 335

Asp Tyr Leu Arg Ser Ala Leu Asp Tyr Leu Glu Leu Gln Pro Asp Leu
            340                 345                 350

Lys Ala Leu Val Arg Gly Ala His Thr Phe Lys Cys Pro Asn Leu Gly
            355                 360                 365

Ile Thr Ser Trp Val Arg Leu Pro Ile His Asp Ala Asp Phe Gly Trp
            370                 375                 380

Gly Arg Pro Ile Phe Met Gly Pro Gly Gly Ile Ala Tyr Glu Gly Leu
385                 390                 395                 400

Ser Phe Ile Leu Pro Ser Pro Thr Asn Asp Gly Ser Met Ser Val Ala
            405                 410                 415

Ile Ser Leu Gln Gly Glu His Met Lys Leu Phe Gln Ser Phe Leu Tyr
            420                 425                 430

Asp Ile

<210> SEQ ID NO 14
<211> LENGTH: 431
<212> TYPE: PRT
<213> ORGANISM: Populus trichocarpa

<400> SEQUENCE: 14

Met Ile Ile Asn Val Lys Glu Ser Thr Met Val Gln Pro Ala Glu Glu
1               5                   10                  15

Thr Pro Arg Arg Gly Leu Trp Asn Ser Asn Val Asp Leu Val Val Pro
            20                  25                  30

Arg Phe His Thr Pro Ser Val Tyr Phe Tyr Arg Pro Thr Gly Ala Pro
            35                  40                  45

Asn Phe Phe Asp Ala Lys Val Leu Lys Gly Ala Leu Ser Lys Ala Leu
        50                  55                  60

Val Pro Phe Tyr Pro Met Ala Gly Arg Leu Arg Arg Asp Glu Asp Gly
65                  70                  75                  80

Arg Ile Glu Ile Asn Cys Asn Ala Glu Gly Val Leu Phe Val Glu Ala
            85                  90                  95

Glu Thr Thr Ser Val Ile Asp Asp Phe Ala Asp Phe Ala Pro Thr Leu
            100                 105                 110

Glu Leu Lys Gln Leu Ile Pro Thr Val Asp Tyr Ser Gly Gly Ile Ser
            115                 120                 125

```
Thr Tyr Pro Leu Leu Val Leu Gln Val Thr Tyr Phe Lys Cys Gly Gly
    130                 135                 140

Val Ser Leu Gly Val Gly Met Gln His His Ala Ala Asp Gly Phe Ser
145                 150                 155                 160

Gly Leu His Phe Val Asn Thr Trp Ser Asp Met Ala Arg Gly Leu Asp
                165                 170                 175

Leu Thr Ile Pro Pro Phe Ile Asp Arg Thr Leu Leu Arg Ala Arg Asp
            180                 185                 190

Pro Pro Gln Pro Val Phe His His Val Glu Tyr Gln Pro Pro Ser
        195                 200                 205

Met Lys Thr Val Leu Glu Thr Ser Lys Pro Glu Ser Thr Ala Val Ser
    210                 215                 220

Ile Phe Lys Leu Ser Arg Asp Gln Leu Ser Thr Leu Lys Ala Lys Ala
225                 230                 235                 240

Lys Glu Asp Gly Asn Asn Ile Ser Tyr Ser Ser Tyr Glu Met Leu Ala
                245                 250                 255

Ala His Val Trp Arg Ser Thr Cys Lys Ala Arg Glu Leu Pro Asp Asp
            260                 265                 270

Gln Glu Thr Lys Leu Tyr Ile Ala Thr Asp Gly Arg Ser Arg Trp Gln
        275                 280                 285

Pro Gln Leu Pro Pro Gly Tyr Phe Gly Asn Val Ile Phe Thr Ala Thr
    290                 295                 300

Pro Ile Ala Val Ala Gly Glu Met Gln Ser Lys Pro Thr Trp Tyr Ala
305                 310                 315                 320

Ala Gly Lys Ile His Asp Ala Leu Val Arg Met Asp Asn Asp Tyr Leu
                325                 330                 335

Lys Ser Ala Leu Asp Tyr Leu Glu Leu Gln Pro Asp Leu Ser Ala Leu
            340                 345                 350

Val Arg Gly Ala His Ser Phe Arg Cys Pro Asn Leu Gly Ile Thr Ser
        355                 360                 365

Trp Val Arg Leu Pro Ile His Asp Ala Asp Phe Gly Trp Gly Arg Pro
    370                 375                 380

Ile Phe Met Gly Pro Gly Gly Ile Ala Tyr Glu Gly Leu Ser Phe Ile
385                 390                 395                 400

Leu Pro Ser Pro Thr Asn Asp Gly Ser Met Ser Val Ala Ile Ser Leu
                405                 410                 415

Gln Ala Gln His Met Lys Leu Phe Glu Lys Phe Ile Tyr Asp Ile
            420                 425                 430

<210> SEQ ID NO 15
<211> LENGTH: 232
<212> TYPE: PRT
<213> ORGANISM: Arabidopsis thaliana

<400> SEQUENCE: 15

Met Ala Lys Asp Glu Ala Lys Gly Leu Leu Lys Ser Glu Glu Leu Tyr
1               5                   10                  15

Lys Tyr Ile Leu Glu Thr Ser Val Tyr Pro Arg Glu Pro Glu Val Leu
            20                  25                  30

Arg Glu Leu Arg Asn Ile Thr His Asn His Pro Gln Ala Gly Met Ala
        35                  40                  45

Thr Ala Pro Asp Ala Gly Gln Leu Met Gly Met Leu Leu Asn Leu Val
    50                  55                  60

Asn Ala Arg Lys Thr Ile Glu Val Gly Val Phe Thr Gly Tyr Ser Leu
65                  70                  75                  80
```

```
Leu Leu Thr Ala Leu Thr Leu Pro Glu Asp Gly Lys Val Ile Ala Ile
                85                  90                  95

Asp Met Asn Arg Asp Ser Tyr Glu Ile Gly Leu Pro Val Ile Lys Lys
            100                 105                 110

Ala Gly Val Glu His Lys Ile Asp Phe Lys Glu Ser Glu Ala Leu Pro
        115                 120                 125

Ala Leu Asp Glu Leu Leu Asn Asn Lys Val Asn Glu Gly Gly Phe Asp
    130                 135                 140

Phe Ala Phe Val Asp Ala Asp Lys Leu Asn Tyr Trp Asn Tyr His Glu
145                 150                 155                 160

Arg Leu Ile Arg Leu Ile Lys Val Gly Ile Ile Val Tyr Asp Asn
                165                 170                 175

Thr Leu Trp Gly Gly Ser Val Ala Glu Pro Asp Ser Ser Thr Pro Glu
                180                 185                 190

Trp Arg Ile Glu Val Lys Lys Ala Thr Leu Glu Leu Asn Lys Lys Leu
            195                 200                 205

Ser Ala Asp Gln Arg Val Gln Ile Ser Gln Ala Ala Leu Gly Asp Gly
    210                 215                 220

Ile Thr Ile Cys Arg Arg Leu Tyr
225                 230

<210> SEQ ID NO 16
<211> LENGTH: 247
<212> TYPE: PRT
<213> ORGANISM: Nicotiana tabacum

<400> SEQUENCE: 16

Met Ala Glu Asn Gly Ala Ala Gln Glu Asn Gln Val Thr Lys His Gln
1               5                   10                  15

Glu Val Gly His Lys Ser Leu Leu Gln Ser Asp Ala Leu Tyr Gln Tyr
            20                  25                  30

Ile Leu Glu Thr Ser Val Tyr Pro Arg Glu Pro Glu Pro Met Lys Glu
        35                  40                  45

Leu Arg Glu Leu Thr Ala Lys His Pro Trp Asn Leu Met Thr Thr Ser
    50                  55                  60

Ala Asp Glu Gly Gln Phe Leu Ser Met Leu Leu Lys Leu Ile Ile Ala
65                  70                  75                  80

Lys Asn Thr Met Glu Ile Gly Val Tyr Thr Gly Tyr Ser Leu Leu Ala
                85                  90                  95

Thr Ala Leu Ala Leu Pro Asp Asp Gly Lys Ile Leu Ala Met Asp Ile
            100                 105                 110

Asn Lys Glu Asn Tyr Glu Leu Gly Leu Pro Val Ile Gln Lys Ala Gly
        115                 120                 125

Val Ala His Lys Ile Asp Phe Arg Glu Gly Pro Ala Leu Pro Val Leu
    130                 135                 140

Asp Leu Met Ile Glu Asp Lys Asn Asn His Gly Thr Tyr Asp Phe Ile
145                 150                 155                 160

Phe Val Asp Ala Asp Lys Asp Asn Tyr Ile Asn Tyr His Lys Arg Ile
                165                 170                 175

Ile Glu Leu Val Lys Val Gly Gly Val Ile Gly Tyr Asp Asn Thr Leu
            180                 185                 190

Trp Asn Gly Ser Val Val Ala Pro Pro Asp Ala Pro Met Arg Lys Tyr
        195                 200                 205

Val Arg Tyr Tyr Arg Asp Phe Val Leu Glu Leu Asn Lys Ala Leu Ala
    210                 215                 220
```

Ala Asp Pro Arg Ile Glu Ile Cys Met Leu Pro Val Gly Asp Gly Ile
225                 230                 235                 240

Thr Leu Cys Arg Arg Ile Ser
            245

<210> SEQ ID NO 17
<211> LENGTH: 336
<212> TYPE: PRT
<213> ORGANISM: Vanilla planifolia

<400> SEQUENCE: 17

Met Gly Phe Glu Glu Asp Asn Pro Ile Arg Ser Val Thr Gln Arg Pro
1               5                   10                  15

Asp Ser Ile Glu Pro Ala Ile Leu Gly Val Leu Gly Ser Cys Arg His
            20                  25                  30

Ala Phe His Phe Ala Arg Phe Ala Arg Arg Tyr Gly Lys Ser Tyr Gly
        35                  40                  45

Ser Glu Glu Ile Lys Lys Arg Phe Gly Ile Phe Val Glu Asn Leu
50                  55                  60

Ala Phe Ile Arg Ser Thr Asn Arg Lys Asp Leu Ser Tyr Thr Leu Gly
65                  70                  75                  80

Ile Asn Gln Phe Ala Asp Leu Thr Trp Glu Glu Phe Arg Thr Asn Arg
                85                  90                  95

Leu Gly Ala Ala Gln Asn Cys Ser Ala Thr Ala His Gly Asn His Arg
            100                 105                 110

Phe Val Asp Gly Val Leu Pro Val Thr Arg Asp Trp Arg Glu Gln Gly
        115                 120                 125

Ile Val Ser Pro Val Lys Asp Gln Gly Ser Cys Gly Ser Cys Trp Thr
130                 135                 140

Phe Ser Thr Thr Gly Ala Leu Glu Ala Ala Tyr Thr Gln Leu Thr Gly
145                 150                 155                 160

Lys Ser Thr Ser Leu Ser Glu Gln Gln Leu Val Asp Cys Ala Ser Ala
                165                 170                 175

Phe Asn Asn Phe Gly Cys Asn Gly Gly Leu Pro Ser Gln Ala Phe Glu
            180                 185                 190

Tyr Val Lys Tyr Asn Gly Gly Ile Asp Thr Glu Gln Thr Tyr Pro Tyr
        195                 200                 205

Leu Gly Val Asn Gly Ile Cys Asn Phe Lys Gln Glu Asn Val Gly Val
210                 215                 220

Lys Val Ile Asp Ser Ile Asn Ile Thr Leu Gly Ala Glu Asp Glu Leu
225                 230                 235                 240

Lys His Ala Val Gly Leu Val Arg Pro Val Ser Val Ala Phe Glu Val
                245                 250                 255

Val Lys Gly Phe Asn Leu Tyr Lys Lys Gly Val Tyr Ser Ser Asp Thr
            260                 265                 270

Cys Gly Arg Asp Pro Met Asp Val Asn His Ala Val Leu Ala Val Gly
        275                 280                 285

Tyr Gly Val Glu Asp Gly Ile Pro Tyr Trp Leu Ile Lys Asn Ser Trp
290                 295                 300

Gly Thr Asn Trp Gly Asp Asn Gly Tyr Phe Lys Met Glu Leu Gly Lys
305                 310                 315                 320

Asn Met Cys Gly Val Ala Thr Cys Ala Ser Tyr Pro Ile Val Ala Val
                325                 330                 335

<210> SEQ ID NO 18
<211> LENGTH: 1071
<212> TYPE: DNA
<213> ORGANISM: Artificial sequence
<220> FEATURE:
<223> OTHER INFORMATION: Codon optimised sequence encoding VpVAN

<400> SEQUENCE: 18

```
atggctgcta aattgctttt cttccttttg tttctggtgt ctgcactatc ggtcgcttta      60
gctggttttg aggaagataa ccctataagg agtgttactc aaagaccaga cagcatagaa     120
ccagctatat tgggagttct aggttcttgc agacatgcgt tcacttcgc cagatttgct      180
agaagatatg gtaaatcgta tggtagtgaa gaagagatca agaaacgttt gggatatatt     240
gtggaaaatt tggccttcat caggtctact aacagaaagg acctgagcta cacattgggg     300
attaatcagt tgccgacttt gacttgggag gaatttagaa ccaatcgtct aggtgcagca     360
caaaattgct ctgcgactgc acatggaaac acagatttg tggatggagt gttacctgtt      420
actagagatt ggagagaaca gggtatcgtt tctcccgtca aagatcaagg ttcatgtggc     480
tcatgttgga cgttctctac aacaggagcc ttagaagctg cctataccca attgacaggg     540
aaatccacaa gtctaagcga caacaactg gttgattgtg cttccgcatt taacaacttt      600
ggctgtaatg gtggtttacc aagtcaagct tttgaatatg tcaagtataa tggaggtatt     660
gatacagaac aaacgtatcc gtatttaggc gtaaacggca tttgcaattt caaacaggaa     720
aatgttgggg ttaaagtgat tgactccatt aacatcacgt gggtgcaga ggacgagtta      780
aaacatgctg tgggtttagt taggcctgtt tcagttgcct tcgaagtagt caaaggtttc     840
aacctttaca gaaaggcgt ttactcttcc gacacttgtg gaagagatcc aatggatgtt      900
aatcatgcag tcttggcagt aggttacggt gtagaagatg gcattcccta ttggcttatt     960
aagaattcat ggggtaccaa ttgggcgat aacggttact tcaagatgga gttaggaaag     1020
aatatgtgcg gagtagctac ctgtgcctca tacccaattg tagcggtcta a             1071
```

<210> SEQ ID NO 19
<211> LENGTH: 102
<212> TYPE: DNA
<213> ORGANISM: artificial sequence
<220> FEATURE:
<223> OTHER INFORMATION: Forward primer

<400> SEQUENCE: 19

```
aacataatgc tgcaaatata gattgatttc aatctacgga gtccaacgca ttgagcagct      60
tcaattgagt agatatgtct aagaatatcg ttgtcctacc gg                        102
```

<210> SEQ ID NO 20
<211> LENGTH: 113
<212> TYPE: DNA
<213> ORGANISM: artificial sequence
<220> FEATURE:
<223> OTHER INFORMATION: Reverse primer

<400> SEQUENCE: 20

```
cgtggagtat aaaagttcgg aaaattttat ttaaaatctg attatatggt ttttcttccg      60
tagaaagtct atggcaatta agccaagatt tccttgacag ccttggcgat agc            113
```

<210> SEQ ID NO 21
<211> LENGTH: 358
<212> TYPE: PRT
<213> ORGANISM: Glechoma hederacea

<400> SEQUENCE: 21

```
Met Ala Arg Leu Leu Leu Leu Val Gly Val Leu Ile Ala Cys Ala
1               5                   10                  15

Ala Gly Ala Arg Ala Gly Ser Glu Phe Leu Ala Glu Asp Asn Pro Ile
            20                  25                  30

Arg Gln Val Val Asp Gly Met His Glu Leu Glu Ser Ser Ile Leu Lys
            35                  40                  45

Ala Val Gly Asn Ser Arg Arg Ala Phe Ser Phe Ala Arg Phe Ala His
        50                  55                  60

Arg Tyr Gly Lys Ser Tyr Glu Ser Ser Glu Glu Ile Gln Lys Arg Phe
65                  70                  75                  80

Gln Val Tyr Ser Glu Asn Leu Arg Met Ile Arg Ser His Asn Lys Lys
                85                  90                  95

Gly Leu Ser Tyr Ser Met Gly Val Asn Glu Phe Ser Asp Leu Thr Trp
            100                 105                 110

Asp Glu Phe Lys Lys His Arg Leu Gly Ala Ala Gln Asn Cys Ser Ala
            115                 120                 125

Thr Arg Arg Gly Asn His Lys Leu Thr Ser Ala Ile Leu Pro Asp Ser
130                 135                 140

Lys Asp Trp Arg Glu Ser Gly Ile Val Ser Pro Val Lys Ser Gln Gly
145                 150                 155                 160

Ser Cys Gly Ser Cys Trp Thr Phe Ser Ser Thr Gly Ala Leu Glu Ala
            165                 170                 175

Ala Tyr Ala Gln Ala Phe Gly Lys Gly Ile Ser Leu Ser Glu Gln Gln
            180                 185                 190

Leu Val Asp Cys Ala Gly Ala Phe Asn Asn Phe Gly Cys Asn Gly Gly
            195                 200                 205

Leu Pro Ser Gln Ala Phe Glu Tyr Ile Lys Tyr Asn Gly Gly Leu Met
            210                 215                 220

Thr Glu Glu Ala Tyr Pro Tyr Thr Gly His Asp Gly Glu Cys Lys Tyr
225                 230                 235                 240

Ser Ser Glu Asn Ala Ala Val Gln Val Leu Asp Ser Val Asn Ile Thr
                245                 250                 255

Leu Gly Ala Glu Asp Glu Leu Lys His Ala Val Ala Leu Val Arg Pro
            260                 265                 270

Val Ser Val Ala Phe Glu Val Val Asp Gly Phe Arg Ser Tyr Asn Gly
            275                 280                 285

Gly Val Tyr Thr Ser Thr Thr Cys Gly Ser Asp Pro Met Asp Val Asn
            290                 295                 300

His Ala Val Leu Ala Val Gly Tyr Gly Val Glu Gly Val Pro Tyr
305                 310                 315                 320

Trp Leu Ile Lys Asn Ser Trp Gly Ala Asp Trp Gly Asp Gln Gly Tyr
            325                 330                 335

Phe Lys Met Glu Met Gly Lys Asn Met Cys Gly Val Ala Thr Cys Ala
            340                 345                 350

Ser Tyr Pro Val Val Ala
            355
```

<210> SEQ ID NO 22
<211> LENGTH: 360
<212> TYPE: PRT
<213> ORGANISM: Nicotiana benthamiana

<400> SEQUENCE: 22

```
Met Ser Arg Phe Ser Leu Leu Ala Leu Val Ala Gly Gly Leu
1               5                   10                  15

Phe Ala Ser Ala Leu Ala Gly Pro Ala Thr Phe Ala Asp Glu Asn Pro
            20                  25                  30

Ile Arg Gln Val Val Ser Asp Gly Leu His Glu Leu Glu Asn Ala Ile
                35                  40                  45

Leu Gln Val Val Gly Lys Thr Arg His Ala Leu Ser Phe Ala Arg Phe
    50                  55                  60

Ala His Arg Tyr Gly Lys Arg Tyr Glu Ser Val Glu Glu Ile Lys Gln
65                  70                  75                  80

Arg Phe Glu Val Phe Leu Asp Asn Leu Lys Met Ile Arg Ser His Asn
                85                  90                  95

Lys Lys Gly Leu Ser Tyr Lys Leu Gly Val Asn Glu Phe Thr Asp Leu
            100                 105                 110

Thr Trp Asp Glu Phe Arg Arg Asp Arg Leu Gly Ala Ala Gln Asn Cys
                115                 120                 125

Ser Ala Thr Thr Lys Gly Asn Leu Lys Val Thr Asn Val Val Leu Pro
130                 135                 140

Glu Thr Lys Asp Trp Arg Glu Ala Gly Ile Val Ser Pro Val Lys Asn
145                 150                 155                 160

Gln Gly Lys Cys Gly Ser Cys Trp Thr Phe Ser Thr Thr Gly Ala Leu
                165                 170                 175

Glu Ala Ala Tyr Ser Gln Ala Phe Gly Lys Gly Ile Ser Leu Ser Glu
            180                 185                 190

Gln Gln Leu Val Asp Cys Ala Gly Ala Phe Asn Asn Phe Gly Cys Asn
        195                 200                 205

Gly Gly Leu Pro Ser Gln Ala Phe Glu Tyr Ile Lys Ser Asn Gly Gly
210                 215                 220

Leu Asp Thr Glu Glu Ala Tyr Pro Tyr Thr Gly Lys Asn Gly Leu Cys
225                 230                 235                 240

Lys Phe Ser Ser Glu Asn Val Gly Val Lys Val Ile Asp Ser Val Asn
                245                 250                 255

Ile Thr Leu Gly Ala Glu Asp Glu Leu Lys Tyr Ala Val Ala Leu Val
            260                 265                 270

Arg Pro Val Ser Ile Ala Phe Glu Val Ile Lys Gly Lys Gln Tyr
        275                 280                 285

Lys Ser Gly Val Tyr Thr Ser Thr Glu Cys Gly Asn Thr Pro Met Asp
290                 295                 300

Val Asn His Ala Val Leu Ala Val Gly Tyr Gly Val Glu Asn Gly Val
305                 310                 315                 320

Pro Tyr Trp Leu Ile Lys Asn Ser Trp Gly Ala Asp Trp Gly Asp Asn
                325                 330                 335

Gly Tyr Phe Lys Met Glu Met Gly Lys Asn Met Cys Gly Ile Ala Thr
            340                 345                 350

Cys Ala Ser Tyr Pro Val Val Ala
            355                 360
```

<210> SEQ ID NO 23
<211> LENGTH: 1077
<212> TYPE: DNA
<213> ORGANISM: Glechoma hederacea

<400> SEQUENCE: 23

```
atggctcgcc ttctgctgct cctcgtcgga gttctgatcg cctgcgccgc cggcgcaaga      60
gccggatcgg agttcctcgc cgaggataat ccgatcaggc aagtcgtcga cggtatgcac     120
gaactcgagt cgtctattct caaagcagtc ggcaactcgc gccgcgcctt ctccttcgct     180
cgctttgctc atagatacgg gaagagctac gagagttcgg aggagataca aagagggttc     240
caagtttact ctgagaattt gaggatgatc cgatcgcata caagaaagg actatcctat      300
tccatgggcg ttaacgagtt ctctgatctg acatgggacg agttcaaaaa gcatagattg     360
ggagctgctc aaaattgctc cgctacaaga aggggcaatc ataagctcac cagtgctatc     420
cttccggact cgaaagactg agggaaagt ggcattgtta gcccagtgaa aagtcaaggt      480
agctgtggat cttgctggac attcagttca actggagcac tggaggcagc ttatgcacaa     540
gcattcggaa agggtatttc tctgtctgag cagcagctcg ttgattgtgc tggagctttc     600
aacaactttg gctgcaatgg tggattgccc tctcaagcct tcgaatacat caaatataac     660
ggtggtctta tgactgagga ggcatatcca tatactggtc atgatggaga atgcaagtat     720
tcctctgaaa atgctgccgt ccaagtactt gactctgtca atatcaccct gggtgctgaa     780
gatgaactta agcacgcagt tgcattggtt cggccagtaa gtgtggcatt tgaggttgtt     840
gatggattcc gatcatacaa tggtggagtt tacactagca ctacttgtgg cagcgatcca     900
atggatgtaa accatgctgt tcttgctgtt ggttacggag ttgaaggtgg cgtgccgtac     960
tggctaatca agaattcatg gggagctgac tgggggggacc aaggctactt caaaatggag    1020
atgggcaaga acatgtgtgg tgttgcaaca tgtgcatcat accctgtagt tgcttaa       1077
```

<210> SEQ ID NO 24
<211> LENGTH: 1071
<212> TYPE: DNA
<213> ORGANISM: Artificial sequence
<220> FEATURE:
<223> OTHER INFORMATION: DNA encoding chimeric vanillin synthase

<400> SEQUENCE: 24

```
atgtctcgtt tctcactcct attggctctc gtcgtcgccg gtggccttt cgcctccgca      60
ctcggtttcg aagaagacaa tccaatccgg tccgttacac aaaggcctga ctcgattgag     120
cctgccatcc tcggcgtcct tggcagttgc cgccacgcct tccacttcgc acggttcgcc     180
cgcaggtacg ggaagagcta cggatcggag gaggagatca agagaggtt cgggatcttc      240
gtggagaatc tagcgtttat ccggtccact aatcggaagg atctgtcgta tacccctagga   300
atcaaccaat cgccgacct gacctgggag gaattccgga ccaatcgcct tggtgcggcg     360
cagaactgct cggcgactgc gcatggaaac caccggtttg tcaacgttgt tctgccggag    420
acgagggatt ggagggagca aggatagtg agccctgtaa aggaccaagg aagctgtgga     480
tcttgctgga ctttcagtac tactggagca ctagaggctg catatacaca gctaactgga     540
aagagcacat cattatctga acagcaactt gtggactgtg cctcagcatt caataacttt    600
ggatgcaatg gaggtttgcc ttcccaagcc tttgaatacg ttaagtacaa tggaggcatc    660
gacacagaac agacttatcc ataccttggt gtcaatggta tctgcaactt caagcaggag    720
aatgttggtg tcaaggtcat tgattcgata acatcaccc tgggtgctga ggatgagttg      780
aagcatgcag tggcttggt gcgtccagtt agcgttgcat ttgaggttgt gaaaggtttc     840
aatctgtaca agaaaggtgt atacagcagt gacacctgtg gaagagatcc aatgatgtg     900
aaccacgcag ttcttgccgt cggttatgga gtcgaggacg ggattcctta ttggctcatc    960
```

```
aagaactcat ggggtacaaa ttggggtgac aatggctact ttaagatgga actcggcaag   1020
aacatgtgtg gtgttgcaac ttgcgcatct tatcccattg tggctgtgta g            1071
```

<210> SEQ ID NO 25
<211> LENGTH: 362
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(15)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(40)
<223> OTHER INFORMATION: Xaa can be any naturally occurring amino acid
<220> FEATURE:
<221> NAME/KEY: misc_feature
<222> LOCATION: (42)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (59)..(60)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid

```
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (83)..(84)
<223> OTHER INFORMATION: Xaa can be any naturally occurring amino acid
<220> FEATURE:
<221> NAME/KEY: misc_feature
<222> LOCATION: (86)..(87)
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (119)..(120)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid
<220> FEATURE:
<221> NAME/KEY: misc_feature
<222> LOCATION: (136)..(141)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
```

```
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (183)..(184)
<223> OTHER INFORMATION: Xaa can be any naturally occurring amino acid
<220> FEATURE:
<221> NAME/KEY: misc_feature
<222> LOCATION: (187)..(188)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (229)..(230)
<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid
<220> FEATURE:
<221> NAME/KEY: misc_feature
<222> LOCATION: (243)..(244)
<223> OTHER INFORMATION: Xaa can be any naturally occurring amino acid
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (270)..(270)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
```

-continued

```
<220> FEATURE:
<221> NAME/KEY: misc_feature
<222> LOCATION: (286)..(287)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid
<220> FEATURE:
<221> NAME/KEY: misc_feature
<222> LOCATION: (296)..(297)
<223> OTHER INFORMATION: Xaa can be any naturally occurring amino acid
<220> FEATURE:
<221> NAME/KEY: misc_feature
<222> LOCATION: (300)..(301)
<223> OTHER INFORMATION: Xaa can be any naturally occurring amino acid
<220> FEATURE:
<221> NAME/KEY: misc_feature
<222> LOCATION: (318)..(318)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (331)..(332)
<223> OTHER INFORMATION: Xaa can be any naturally occurring amino acid
<220> FEATURE:
<221> NAME/KEY: misc_feature
<222> LOCATION: (343)..(343)
<223> OTHER INFORMATION: Xaa can be any naturally occurring amino acid
<220> FEATURE:
<221> NAME/KEY: misc_feature
<222> LOCATION: (350)..(350)
<223> OTHER INFORMATION: Xaa can be any naturally occurring amino acid
<220> FEATURE:
<221> NAME/KEY: misc_feature
<222> LOCATION: (358)..(358)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid

<400> SEQUENCE: 25

Met Xaa Xaa Xaa Xaa Leu Xaa Xaa Leu Xaa Xaa Xaa Xaa Xaa Leu
1               5                   10                  15

Phe Xaa Xaa Ala Leu Ala Gly Pro Ala Thr Phe Xaa Xaa Xaa Asn Pro
            20                  25                  30

Ile Arg Xaa Val Xaa Xaa Xaa Xaa Leu Xaa Xaa Xaa Glu Xaa Ala Ile
        35                  40                  45

Leu Xaa Val Xaa Gly Xaa Xaa Arg His Ala Xaa Xaa Phe Ala Arg Phe
    50                  55                  60

Ala Xaa Arg Tyr Gly Lys Xaa Tyr Xaa Ser Xaa Glu Glu Ile Lys Xaa
65              70                  75                  80

Arg Phe Xaa Xaa Phe Xaa Xaa Asn Leu Xaa Xaa Ile Arg Ser Xaa Asn
                85                  90                  95

Xaa Lys Xaa Leu Ser Tyr Xaa Leu Gly Xaa Asn Xaa Phe Xaa Asp Leu
            100                 105                 110

Thr Trp Xaa Glu Phe Arg Xaa Xaa Arg Leu Gly Ala Ala Gln Asn Cys
        115                 120                 125

Ser Ala Thr Xaa Xaa Gly Asn Xaa Xaa Xaa Xaa Xaa Xaa Val Leu Pro
130                 135                 140
```

```
Xaa Thr Xaa Asp Trp Arg Glu Xaa Gly Ile Val Ser Pro Val Lys Xaa
145                 150                 155                 160

Gln Gly Xaa Cys Gly Ser Cys Trp Thr Phe Ser Thr Thr Gly Ala Leu
            165                 170                 175

Glu Ala Ala Tyr Xaa Gln Xaa Xaa Gly Lys Xaa Xaa Ser Leu Ser Glu
            180                 185                 190

Gln Gln Leu Val Asp Cys Ala Xaa Ala Phe Asn Asn Phe Gly Cys Asn
        195                 200                 205

Gly Gly Leu Pro Ser Gln Ala Phe Glu Tyr Xaa Lys Xaa Asn Gly Gly
    210                 215                 220

Xaa Asp Thr Glu Xaa Xaa Tyr Pro Tyr Xaa Gly Xaa Asn Gly Xaa Cys
225                 230                 235                 240

Xaa Phe Xaa Xaa Glu Asn Val Gly Val Lys Val Ile Asp Ser Xaa Asn
            245                 250                 255

Ile Thr Leu Gly Ala Glu Asp Glu Leu Lys Xaa Ala Val Xaa Leu Val
            260                 265                 270

Arg Pro Val Ser Xaa Ala Phe Glu Val Xaa Lys Gly Phe Xaa Xaa Tyr
            275                 280                 285

Lys Xaa Gly Val Tyr Xaa Ser Xaa Xaa Cys Gly Xaa Xaa Pro Met Asp
290                 295                 300

Val Asn His Ala Val Leu Ala Val Gly Tyr Gly Val Glu Xaa Gly Xaa
305                 310                 315                 320

Pro Tyr Trp Leu Ile Lys Asn Ser Trp Gly Xaa Xaa Trp Gly Asp Asn
            325                 330                 335

Gly Tyr Phe Lys Met Glu Xaa Gly Lys Asn Met Cys Gly Xaa Ala Thr
            340                 345                 350

Cys Ala Ser Tyr Pro Xaa Val Ala Val Xaa
            355                 360

<210> SEQ ID NO 26
<211> LENGTH: 360
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(42)
<223> OTHER INFORMATION: Xaa can be any naturally occurring amino acid
```

```
<220> FEATURE:
<221> NAME/KEY: misc_feature
<222> LOCATION: (44)..(45)
<223> OTHER INFORMATION: Xaa can be any naturally occurring amino acid
<220> FEATURE:
<221> NAME/KEY: misc_feature
<222> LOCATION: (48)..(50)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (81)..(84)
<223> OTHER INFORMATION: Xaa can be any naturally occurring amino acid
<220> FEATURE:
<221> NAME/KEY: misc_feature
<222> LOCATION: (88)..(89)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (101)..(102)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
```

```
<220> FEATURE:
<221> NAME/KEY: misc_feature
<222> LOCATION: (116)..(118)
<223> OTHER INFORMATION: Xaa can be any naturally occurring amino acid
<220> FEATURE:
<221> NAME/KEY: misc_feature
<222> LOCATION: (130)..(131)
<223> OTHER INFORMATION: Xaa can be any naturally occurring amino acid
<220> FEATURE:
<221> NAME/KEY: misc_feature
<222> LOCATION: (135)..(140)
<223> OTHER INFORMATION: Xaa can be any naturally occurring amino acid
<220> FEATURE:
<221> NAME/KEY: misc_feature
<222> LOCATION: (143)..(145)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (181)..(182)
<223> OTHER INFORMATION: Xaa can be any naturally occurring amino acid
<220> FEATURE:
<221> NAME/KEY: misc_feature
<222> LOCATION: (185)..(186)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (223)..(224)
<223> OTHER INFORMATION: Xaa can be any naturally occurring amino acid
<220> FEATURE:
<221> NAME/KEY: misc_feature
<222> LOCATION: (227)..(228)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (234)..(235)
<223> OTHER INFORMATION: Xaa can be any naturally occurring amino acid
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (239)..(242)
<223> OTHER INFORMATION: Xaa can be any naturally occurring amino acid
<220> FEATURE:
<221> NAME/KEY: misc_feature
<222> LOCATION: (245)..(246)
<223> OTHER INFORMATION: Xaa can be any naturally occurring amino acid
```

```
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (284)..(285)
<223> OTHER INFORMATION: Xaa can be any naturally occurring amino acid
<220> FEATURE:
<221> NAME/KEY: misc_feature
<222> LOCATION: (287)..(288)
<223> OTHER INFORMATION: Xaa can be any naturally occurring amino acid
<220> FEATURE:
<221> NAME/KEY: misc_feature
<222> LOCATION: (292)..(292)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid
<220> FEATURE:
<221> NAME/KEY: misc_feature
<222> LOCATION: (298)..(298)
<223> OTHER INFORMATION: Xaa can be any naturally occurring amino acid
<220> FEATURE:
<221> NAME/KEY: misc_feature
<222> LOCATION: (316)..(316)
<223> OTHER INFORMATION: Xaa can be any naturally occurring amino acid
<220> FEATURE:
<221> NAME/KEY: misc_feature
<222> LOCATION: (318)..(318)
<223> OTHER INFORMATION: Xaa can be any naturally occurring amino acid
<220> FEATURE:
<221> NAME/KEY: misc_feature
<222> LOCATION: (329)..(330)
<223> OTHER INFORMATION: Xaa can be any naturally occurring amino acid
<220> FEATURE:
<221> NAME/KEY: misc_feature
<222> LOCATION: (334)..(334)
<223> OTHER INFORMATION: Xaa can be any naturally occurring amino acid
<220> FEATURE:
<221> NAME/KEY: misc_feature
<222> LOCATION: (341)..(341)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid
<220> FEATURE:
<221> NAME/KEY: misc_feature
<222> LOCATION: (360)..(360)
<223> OTHER INFORMATION: Xaa can be any naturally occurring amino acid

<400> SEQUENCE: 26

Met Ala Xaa Xaa Leu Leu Xaa Xaa Xaa Xaa Leu Xaa Xaa Xaa Xaa
1               5                   10                  15

Xaa Xaa Ala Xaa Ala Gly Xaa Glu Phe Leu Ala Glu Asp Asn Pro Ile
            20                  25                  30

Arg Xaa Val Xaa Xaa Xaa Xaa Xaa Xaa Xaa Glu Xaa Xaa Ile Leu Xaa
        35                  40                  45
```

-continued

```
Xaa Xaa Gly Xaa Xaa Arg Xaa Ala Phe Xaa Phe Ala Arg Phe Ala Xaa
     50                  55                  60

Arg Tyr Gly Lys Ser Tyr Xaa Ser Xaa Glu Glu Ile Xaa Lys Arg Phe
 65              70                  75                      80

Xaa Xaa Xaa Xaa Glu Asn Leu Xaa Xaa Ile Arg Ser Xaa Asn Xaa Lys
             85                  90              95

Xaa Leu Ser Tyr Xaa Xaa Gly Xaa Asn Xaa Phe Xaa Asp Leu Thr Trp
             100             105             110

Xaa Glu Phe Xaa Xaa Xaa Arg Leu Gly Ala Ala Gln Asn Cys Ser Ala
         115             120             125

Thr Xaa Xaa Gly Asn His Xaa Xaa Xaa Xaa Xaa Xaa Leu Pro Xaa Xaa
     130             135             140

Xaa Asp Trp Arg Glu Xaa Gly Ile Val Ser Pro Val Lys Xaa Gln Gly
145             150             155                     160

Ser Cys Gly Ser Cys Trp Thr Phe Ser Xaa Thr Gly Ala Leu Glu Ala
             165             170             175

Ala Tyr Xaa Gln Xaa Xaa Gly Lys Xaa Xaa Ser Leu Ser Glu Gln Gln
         180             185             190

Leu Val Asp Cys Ala Xaa Ala Phe Asn Asn Phe Gly Cys Asn Gly Gly
         195             200             205

Leu Pro Ser Gln Ala Phe Glu Tyr Xaa Lys Tyr Asn Gly Gly Xaa Xaa
     210             215             220

Thr Glu Xaa Xaa Tyr Pro Tyr Xaa Gly Xaa Xaa Gly Xaa Cys Xaa Xaa
225             230             235                     240

Xaa Xaa Glu Asn Xaa Xaa Val Xaa Val Xaa Asp Ser Xaa Asn Ile Thr
             245             250             255

Leu Gly Ala Glu Asp Glu Leu Lys His Ala Val Xaa Leu Val Arg Pro
             260             265             270

Val Ser Val Ala Phe Glu Val Val Xaa Gly Phe Xaa Xaa Tyr Xaa Xaa
         275             280             285

Gly Val Tyr Xaa Ser Xaa Thr Cys Gly Xaa Asp Pro Met Asp Val Asn
         290             295             300

His Ala Val Leu Ala Val Gly Tyr Gly Val Glu Xaa Gly Xaa Pro Tyr
305             310             315                     320

Trp Leu Ile Lys Asn Ser Trp Gly Xaa Xaa Trp Gly Asp Xaa Gly Tyr
             325             330             335

Phe Lys Met Glu Xaa Gly Lys Asn Met Cys Gly Val Ala Thr Cys Ala
             340             345             350

Ser Tyr Pro Xaa Val Ala Val Xaa
             355             360
```